(12) United States Patent
Boy et al.

(10) Patent No.: US 7,273,866 B2
(45) Date of Patent: Sep. 25, 2007

(54) 2-ARYL THIAZOLE DERIVATIVES AS KCNQ MODULATORS

(75) Inventors: Kenneth M. Boy, Durham, CT (US); Yong-Jin Wu, Madison, CT (US); Jason M. Guernon, Hamden, CT (US)

(73) Assignee: Bristol-Myers Squibb Company, Princeton, NJ (US)

(*) Notice: Subject to any disclaimer, the term of this patent is extended or adjusted under 35 U.S.C. 154(b) by 249 days.

(21) Appl. No.: 10/731,854

(22) Filed: Dec. 9, 2003

(65) Prior Publication Data

US 2004/0147401 A1    Jul. 29, 2004

Related U.S. Application Data

(60) Provisional application No. 60/435,970, filed on Dec. 20, 2002.

(51) Int. Cl.
- A61K 31/5375 (2006.01)
- A61K 31/427 (2006.01)
- A61K 31/426 (2006.01)
- C07D 413/12 (2006.01)
- C07D 413/14 (2006.01)

(52) U.S. Cl. .................. 514/237.2; 514/342; 514/365; 546/124; 546/270.4; 548/200

(58) Field of Classification Search ............... 544/124; 514/237.2, 342, 365; 546/270.4; 548/200
See application file for complete search history.

(56) References Cited

U.S. PATENT DOCUMENTS

| | | |
|---|---|---|
| 3,689,481 A | 9/1972 | Scheuermann et al. |
| 3,794,636 A | 2/1974 | Girgis |
| 3,872,124 A | 3/1975 | LeMartret et al. |
| 4,923,886 A | 5/1990 | Shiokawa et al. |
| 4,980,363 A | 12/1990 | Shimotori et al. |
| 5,057,142 A | 10/1991 | Baasner et al. |
| 5,244,867 A | 9/1993 | Ditrich et al. |
| 5,614,520 A | 3/1997 | Kondo et al. |
| 5,846,990 A | 12/1998 | Murugesan et al. |
| 5,859,035 A | 1/1999 | Anthony et al. |
| 5,888,941 A | 3/1999 | Bartroli et al. |
| 5,998,450 A | 12/1999 | Eicken et al. |
| 6,518,290 B1 * | 2/2003 | Sierra .......................... 514/365 |

FOREIGN PATENT DOCUMENTS

| | | |
|---|---|---|
| JP | 57183768 | 11/1982 |
| JP | 01250379 | 10/1989 |
| JP | 02229190 | 9/1990 |
| JP | 04049290 | 2/1992 |
| JP | 4-128275 * | 4/1992 |
| JP | 128275 | 4/1992 |
| JP | 04128275 | 4/1992 |
| WO | WO 95/19972 | 7/1995 |
| WO | WO 98/28282 | 7/1998 |
| WO | WO 99/59570 | 11/1999 |
| WO | WO 99/66925 | 12/1999 |
| WO | WO 00/06085 | 2/2000 |
| WO | WO 01/10798 | 2/2001 |
| WO | WO 01/40207 A1 | 6/2001 |

OTHER PUBLICATIONS

H.-S. Wang, et al, "KCNQ2 and KCNQ3 Potassium Channel Subunits: Molecular Correlates of the M-Channel," Science, 282, pp. 1890-1893, 1998.

* cited by examiner

Primary Examiner—Patricia L. Morris
(74) Attorney, Agent, or Firm—James Epperson

(57) ABSTRACT

Novel 2-arylthiazole derivatives of Formula I are described which are openers of KCNQ potassium channels and are useful in the treatment of disorders that are responsive to the opening of the KCNQ potassium channels, including pain and migraine

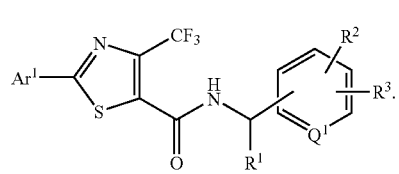

10 Claims, No Drawings

2-ARYL THIAZOLE DERIVATIVES AS KCNQ MODULATORS

REFERENCE TO RELATED APPLICATIONS

This application claims the benefit of U.S. provisional application No. 60/435,970, filed Dec. 20, 2002.

BACKGROUND OF THE INVENTION

The present invention is directed to novel 2-arylthiazole compounds which are modulators of KCNQ potassium channels and are useful in treating disorders responsive to the modulation of the potassium channels. The invention also provides pharmaceutical compositions and methods of treatment with the novel 2-arylthiazole compounds.

Potassium ($K^+$) channels are a diverse class of ion channels and have several critical roles in cell function. One role is in neurons, where $K^+$ channels are responsible, in part, for determining cell excitability by contributing to membrane repolarization following depolarization, resting membrane potential, and regulation of neurotransmitter release. The M-current, measured by electrophysiology recording methods and by pharmacology, has been described as a dominant conductance in controlling neuronal excitability. Pharmacological activation or suppression of M-currents by small molecules could have profound effects in controlling neuronal excitability. Recently, Wang reported that co-assembly of the KCNQ2 and KCNQ3 potassium channels underlies the native M-current in neurons (Wang et al., *Science* 1998, 282, 1890-1893).

Activation or opening of the KCNQ channels, particularly the KCNQ2 or KCNQ2/3 channels, mutated or wild type, may be beneficial for increasing hyperpolarization of neurons, thereby resulting in protection from abnormal synchronous firing during a migraine attack. This invention provides a solution to the problem of abnormal synchronous firing of neurons related to migraine headache by demonstrating that modulators, preferably openers, of KCNQ potassium channels increase hyperpolarization of neurons. This leads to protection against abnormal synchronous neuron firing involved in migraine attacks.

Although the symptom pattern varies among migraine sufferers, the severity of migraine pain justifies a need for vigorous, yet safe and effective, treatments and therapies for the great majority of cases. A need exists for agents that can be used to combat and relieve migraine (and diseases similar to and mechanistically related to migraine), as well as prevent the recurrence of migraine. Also needed are abortive anti-migraine agents, effective in the treatment of acute migraine, as well as in the prodrome phase of a migraine attack. Thus, a clear goal in the art is to discover new, safe, nontoxic and effective anti-migraine compounds and their pharmaceutical compositions for use in anti-migraine treatments.

Because migraine afflicts a large percentage of the population, there is a need to discover compounds and agents that are useful in therapeutics and treatments, and as components of pharmaceutical compositions, for treating the pain and discomfort of migraine headache and other symptoms of migraine. This invention satisfies this need by providing compounds that function as openers of the KCNQ family of potassium ion channels and act as anti-migraine agents.

A number of thiazole derivatives have been disclosed. These references do not teach or suggest the compounds of this invention. See the following: WO 01/40207 A1, JP 04128275 A2, U.S. Pat. No. 5,244,867, U.S. Pat. No. 4,980,363, U.S. Pat. No. 5,846,990, JP 04049290 A2, WO 99/66925 A1, U.S. Pat. No. 5,888,941, U.S. Pat. No. 3,794,636, JP 57183768 A2, U.S. Pat. No. 5,057,142, U.S. Pat. No. 5,859,035, JP 02229190 A2, WO 98/28282 A2, WO 00/06085 A2, U.S. Pat. No. 5,614,520, U.S. Pat. No. 3,689,481, JP 01250379 A2, U.S. Pat. No. 3,872,124, U.S. Pat. No. 4,923,886, WO 99/59570 A1, WO 01/10798 A1, and WO 95/19972 A1.

SUMMARY OF THE INVENTION

The invention encompasses novel 2-arylthiazole compounds and related derivatives of Formula I.

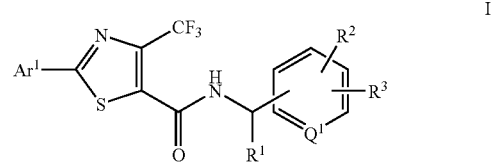

The compounds are openers or activators of KCNQ potassium channels. The invention also describes pharmaceutical compositions and methods of treating disorders sensitive to KCNQ potassium channel opening activity.

DETAILED DESCRIPTION OF THE INVENTION

The invention encompasses compounds of Formula I and related derivatives, including pharmaceutically acceptable salts and solvates,

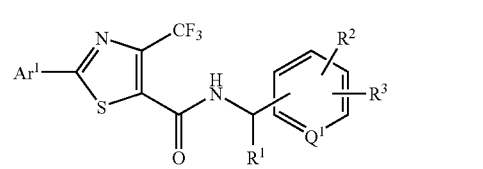

where:
$Q^1$ is CH or N;
$Ar^1$ is selected from the group consisting of

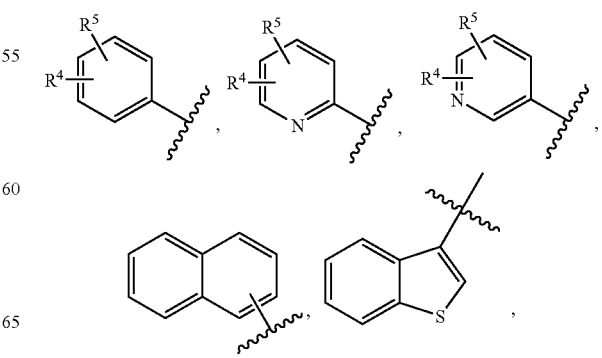

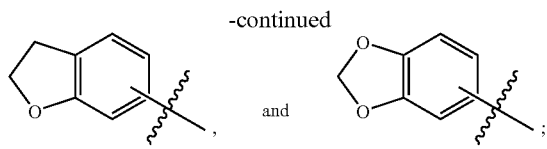

R¹ is hydrogen, $C_{1-6}$alkyl, hydroxymethyl, or trifluoromethyl;

R² is halogen, $C_{1-6}$alkyl, $C_{1-2}$perfluoroalkyl, $C_{1-6}$alkoxy, $C_{1-2}$perfluoroalkoxy, —NR⁶R⁷, —(CH₂)₁₋₄NR⁶R⁷, —O(CH₂)₂₋₃NR⁶R⁷, or pyridyl;

R³ is hydrogen, halogen, or $C_{1-6}$alkoxy;

R⁴ is halogen, $C_{1-6}$alkyl, $C_{1-6}$alkoxy, —NR⁶R⁷, —(CH₂)₁₋₄NR⁶R⁷, —O(CH₂)₂₋₃NR⁶R⁷, or

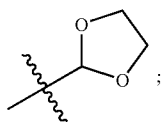

R⁵ is hydrogen, halogen, or $C_{1-6}$alkoxy;

R⁶ is hydrogen, $C_{1-6}$alkyl, —C(=NH)NH₂,

or

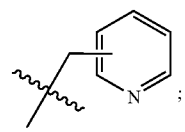

R⁷ is hydrogen or $C_{1-6}$alkyl;

or R⁶ and R⁷ taken together are —CH₂CH(CH₃)OCH(CH₃)CH₂— or —CH₂CH₂XCH₂CH₂—, where X is a chemical bond, CH₂, CHOH, NH, NCH₃, NCOCH₃, O, or S.

"$C_{1-6}$ alkyl" means straight or branched chain alkyl groups such as methyl, ethyl, propyl, isopropyl, butyl, isobutyl, and tert-butyl. "$C_{1-6}$ alkoxy" means an oxygen substituted with straight or branched chain alkyl groups and includes groups such as methoxy, ethoxy, propoxy, isopropoxy, butoxy, isobutoxy, and tert-butoxy.

"KCNQ" means the family of polypeptides that have been described as KCNQ2, KCNQ3, KCNQ4, and KCNQ5 potassium channels as well as heteromultimers of different members. For example, KCNQ2/3, KCNQ2/5 and KCNQ3/5.

The term "pain" includes all types of acute and chronic pain, such as migraine or a migraine attack, cluster headaches, musculoskeletal pain, post-operative pain, surgical pain, inflammatory pain, neuropathic pain such as diabetic neuropathy and pain associated with cancer and fibromyalgias, chronic lower back pain, herpes neuralgia, phantom limb pain, central pain, dental pain, opioid-resistant pain, visceral pain, surgical pain, bone injury pain, pain during labor and delivery, pain resulting from burns, including sunburn, post partum pain, migraine, angina pain, and genitourinary tract-related pain including cystitis. The term is also intended to include nociceptive pain or nociception.

"Therapeutically effective amount" means the amount of a compound required to elicit a meaningful patient benefit. For example, the amount of compound or composition necessary to improve a clinical parameter or ameliorate a symptom.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

The invention also includes all solvated forms of the instant compounds, particularly hydrates. Solvates do not contribute significantly to the physiological activity or toxicity of the compounds and as such function as pharmacological equivalents. Solvates may form in stoichiometric amounts or may form from adventitious solvent or a combination of both. One type of solvate is hydrate, and some hydrated forms include monohydrate, hemihydrate, and dihydrate.

Some of the compounds of the invention possess asymmetric carbon atoms, such as the carbon atom bearing R¹ in Formula Ia. The invention includes all stereoisomeric forms. Stereoisomeric mixtures of the compounds and related intermediates can be separated into individual isomers according to methods commonly known in the art.

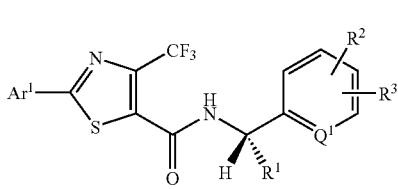

Ia

One aspect of the invention includes compounds of Formula I where Q¹ is CH.

Another aspect of the invention are compounds of Formula I where Ar¹ is

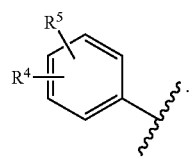

Another aspect of the invention are compounds of Formula I where Ar¹ is

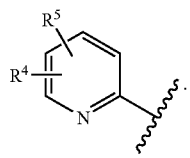

Another aspect of the invention are compounds of Formula I where $R^1$ is hydrogen or methyl.

Another aspect of the invention are compounds of Formula Ig.

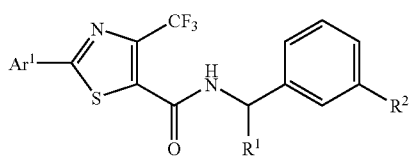

Another aspect of the invention are compounds of Formula I where $R^1$ is $C_{1-6}$alkyl and the compound is that of Formula Ia.

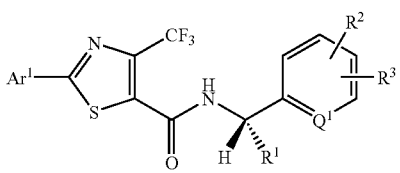

Some compounds of the invention include the following:
(1) 2-(4-fluorophenyl)-N-[1-[3-(trifluoromethoxy)phenyl]ethyl]-4-(trifluoromethyl)-5-thiazolecarboxamide;
(2) 2-(2-methoxyphenyl)-N-[1-[3-(trifluoromethoxy)phenyl]ethyl]-4-(trifluoromethyl)-5-thiazolecarboxamide;
(3) 2-(2-methoxyphenyl)-4-(trifluoromethyl)-N-[1-[3-(trifluoromethyl)phenyl]ethyl]-5-thiazolecarboxamide;
(4) 2-(2-fluorophenyl)-N-[1-[3-(trifluoromethoxy)phenyl]ethyl]-4-(trifluoromethyl)-5-thiazolecarboxamide;
(5) 2-(2-fluorophenyl)-4-(trifluoromethyl)-N-[1-[3-(trifluoromethyl)phenyl]ethyl]-5-thiazolecarboxamide;
(6) 2-(2-methoxyphenyl)-N-[(1S)-1-[3-(4-morpholinyl)phenyl]ethyl]-4-(trifluoromethyl)-5-thiazolecarboxamide;
(7) 2-(3-methoxyphenyl)-N-[1-[3-(trifluoromethoxy)phenyl]ethyl]-4-(trifluoromethyl)-5-thiazolecarboxamide;
(8) N-[1-[3-(dimethylamino)phenyl]ethyl]-2-(2-methoxyphenyl)-4-(trifluoromethyl)-5-thiazolecarboxamide;
(9) N-[1-[3-(dimethylamino)phenyl]ethyl]-2-(2-fluorophenyl)-4-(trifluoromethyl)-5-thiazolecarboxamide;
(10) N-[(3-fluorophenyl)methyl]-2-(2-methoxyphenyl)-4-(trifluoromethyl)-5-thiazolecarboxamide;
(11) 2-(4-methoxyphenyl)-N-[1-[3-(trifluoromethoxy)phenyl]ethyl]-4-(trifluoromethyl)-5-thiazolecarboxamide;
(12) 2-(3,4-dimethoxyphenyl)-N-[1-[3-(trifluoromethoxy)phenyl]ethyl]-4-(trifluoromethyl)-5-thiazolecarboxamide;
(13) 2-(2,4-dimethoxyphenyl)-N-[1-[3-(trifluoromethoxy)phenyl]ethyl]-4-(trifluoromethyl)-5-thiazolecarboxamide;
(14) 2-(2,4-dimethoxyphenyl)-N-[(1S)-1-[3-(4-morpholinyl)phenyl]ethyl]-4-(trifluoromethyl)-5-thiazolecarboxamide;
(15) 2-(2-methoxyphenyl)-N-[1-[3-(1-piperidinyl)phenyl]ethyl]-4-(trifluoromethyl)-5-thiazolecarboxamide;
(16) 2-(2-methoxyphenyl)-N-[1-[3-(1-pyrrolidinyl)phenyl]ethyl]-4-(trifluoromethyl)-5-thiazolecarboxamide;
(17) N-[1-[3-[(2-furanylmethyl)methylamino]phenyl]ethyl]-2-(2-methoxyphenyl)-4-(trifluoromethyl)-5-thiazolecarboxamide;
(18) 2-(2-fluorophenyl)-N-[1-[3-[(2-furanylmethyl)methylamino]phenyl]ethyl]-4-(trifluoromethyl)-5-thiazolecarboxamide;
(19) 2-(3,4-dimethoxyphenyl)-N-[1-[3-(1-pyrrolidinylmethyl)phenyl]ethyl]-4-(trifluoromethyl)-5-thiazolecarboxamide;
(20) 2-(2-fluorophenyl)-N-[1-[3-(4-morpholinylmethyl)phenyl]ethyl]-4-(trifluoromethyl)-5-thiazolecarboxamide;
(21) N-[1-(3-aminophenyl)ethyl]-2-(2-methoxyphenyl)-4-(trifluoromethyl)-5-thiazolecarboxamide;
(22) N-[1-[3-[(aminoiminomethyl)amino]phenyl]ethyl]-2-(2-methoxyphenyl)-4-(trifluoromethyl)-5-thiazolecarboxamide;
(23) 2-(5-fluoro-2-methoxyphenyl)-N-[1-[3-(trifluoromethoxy)phenyl]ethyl]-4-(trifluoromethyl)-5-thiazolecarboxamide;
(24) N-[1-[3-(dimethylamino)phenyl]ethyl]-2-(5-fluoro-2-methoxyphenyl)-4-(trifluoromethyl)-5-thiazolecarboxamide;
(25) 2-(5-fluoro-2-methoxyphenyl)-4-(trifluoromethyl)-N-[1-[3-(trifluoromethyl)phenyl]ethyl]-5-thiazolecarboxamide;
(26) 2-(5-fluoro-2-methoxyphenyl)-N-[(3-fluorophenyl)methyl]-4-(trifluoromethyl)-5-thiazolecarboxamide;
(27) 2-(5-fluoro-2-methoxyphenyl)-N-[(3-methoxyphenyl)methyl]-4-(trifluoromethyl)-5-thiazolecarboxamide;
(28) 2-(5-fluoro-2-methoxyphenyl)-N-[[3-(trifluoromethoxy)phenyl]methyl]-4-(trifluoromethyl)-5-thiazolecarboxamide;
(29) 2-(5-fluoro-2-methoxyphenyl)-N-[(1S)-1-[3-(4-morpholinyl)phenyl]ethyl]-4-(trifluoromethyl)-5-thiazolecarboxamide;
(30) 2-(5-fluoro-2-methoxyphenyl)-N-[(1S)-1-(3-methoxyphenyl)ethyl]-4-(trifluoromethyl)-5-thiazolecarboxamide;
(31) 2-(2-chlorophenyl)-N-[1-[3-(trifluoromethoxy)phenyl]ethyl]-4-(trifluoromethyl)-5-thiazolecarboxamide;
(32) 2-(2-chlorophenyl)-N-[1-[3-(dimethylamino)phenyl]ethyl]-4-(trifluoromethyl)-5-thiazolecarboxamide;
(33) 2-(2-chlorophenyl)-4-(trifluoromethyl)-N-[1-[3-(trifluoromethyl)phenyl]ethyl]-5-thiazolecarboxamide;
(34) 2-(2-chlorophenyl)-N-[(1S)-1-[3-(4-morpholinyl)phenyl]ethyl]-4-(trifluoromethyl)-5-thiazolecarboxamide;
(35) 2-(2-chlorophenyl)-N-[1-[3-(4-morpholinylmethyl)phenyl]ethyl]-4-(trifluoromethyl)-5-thiazolecarboxamide;
(36) 2-[2-[2-(diethylamino)ethoxy]phenyl]-N-[(3-fluorophenyl)methyl]-4-(trifluoromethyl)-5-thiazolecarboxamide;
(37) N-[(1S)-1-(3-methoxyphenyl)ethyl]-2-[2-(4-morpholinyl)phenyl]-4-(trifluoromethyl)-5-thiazolecarboxamide;
(38) 2-[2-(4-morpholinyl)phenyl]-4-(trifluoromethyl)-N-[1-[3-(trifluoromethyl)phenyl]ethyl]-5-thiazolecarboxamide;

(39) 2-[2-(4-morpholinyl)phenyl]-N-[1-[3-(trifluoromethoxy)phenyl]ethyl]-4-(trifluoromethyl)-5-thiazolecarboxamide;
(40) 2-[4-(4-morpholinyl)phenyl]-N-[1-[3-(trifluoromethoxy)phenyl]ethyl]-4-(trifluoromethyl)-5-thiazolecarboxamide;
(41) 2-[2-[[ethyl(4-pyridinylmethyl)amino]methyl]phenyl]-N-[[3-(trifluoromethoxy)phenyl]methyl]-4-(trifluoromethyl)-5-thiazolecarboxamide;
(42) 2-[2-[[ethyl(4-pyridinylmethyl)amino]methyl]phenyl]-N-[(1S)-1-(3-methoxyphenyl)ethyl]-4-(trifluoromethyl)-5-thiazolecarboxamide;
(43) 2-[2-[(dimethylamino)methyl]phenyl]-N-[1-[3-(trifluoromethoxy)phenyl]ethyl]-4-(trifluoromethyl)-5-thiazolecarboxamide;
(44) 2-[2-[(dimethylamino)methyl]phenyl]-N-[[3-(trifluoromethoxy)phenyl]methyl]-4-(trifluoromethyl)-5-thiazolecarboxamide;
(45) 2-[2-[(dimethylamino)methyl]phenyl]-N-[(1S)-1-(3-methoxyphenyl)ethyl]-4-(trifluoromethyl)-5-thiazolecarboxamide;
(46) 2-[2-[(diethylamino)methyl]phenyl]-N-[1-[3-(trifluoromethoxy)phenyl]ethyl]-4-(trifluoromethyl)-5-thiazolecarboxamide;
(47) 2-[2-[(diethylamino)methyl]phenyl]-4-(trifluoromethyl)-N-[1-[3-(trifluoromethyl)phenyl]ethyl]-5-thiazolecarboxamide;
(48) 2-[2-[(diethylamino)methyl]phenyl]-N-[(3-fluorophenyl)methyl]-4-(trifluoromethyl)-5-thiazolecarboxamide;
(49) 2-[2-[(diethylamino)methyl]phenyl]-N-[[3-(trifluoromethoxy)phenyl]methyl]-4-(trifluoromethyl)-5-thiazolecarboxamide;
(50) 2-[2-[(diethylamino)methyl]phenyl]-N-[(1S)-1-[3-(4-morpholinyl)phenyl]ethyl]-4-(trifluoromethyl)-5-thiazolecarboxamide;
(51) 2-[2-[(diethylamino)methyl]phenyl]-N-[(1S)-1-(3-methoxyphenyl)ethyl]-4-(trifluoromethyl)-5-thiazolecarboxamide;
(52) 2-(4-fluorophenyl)-4-(trifluoromethyl)-N-[1-[3-(trifluoromethyl)phenyl]ethyl]-5-thiazolecarboxamide;
(53) 2-(2-methoxyphenyl)-N-(3-pyridinylmethyl)-4-(trifluoromethyl)-5-thiazolecarboxamide;
(54) N-[(3-fluorophenyl)methyl]-2-(3-methoxyphenyl)-4-(trifluoromethyl)-5-thiazolecarboxamide;
(55) N-[1-(2,3-dihydro-5-benzofuranyl)ethyl]-2-(3-methoxyphenyl)-4-(trifluoromethyl)-5-thiazolecarboxamide;
(56) 2-(3-methoxyphenyl)-N-(3-pyridinylmethyl)-4-(trifluoromethyl)-5-thiazolecarboxamide;
(57) 2-(3,4-dimethoxyphenyl)-4-(trifluoromethyl)-N-[1-[3-(trifluoromethyl)phenyl]ethyl]-5-thiazolecarboxamide;
(58) 2-(3,4-dimethoxyphenyl)-N-[1-(3,4-dimethoxyphenyl)ethyl]-4-(trifluoromethyl)-5-thiazolecarboxamide;
(59) 2-(3,4-dimethoxyphenyl)-N-[[3-(trifluoromethoxy)phenyl]methyl]-4-(trifluoromethyl)-5-thiazolecarboxamide;
(60) 2-(3-fluorophenyl)-4-(trifluoromethyl)-N-[1-[3-(trifluoromethyl)phenyl]ethyl]-5-thiazolecarboxamide;
(61) 2-(2,4-dimethoxyphenyl)-N-[(3-fluorophenyl)methyl]-4-(trifluoromethyl)-5-thiazolecarboxamide;
(62) 2-(3-fluorophenyl)-N-[1-[3-(trifluoromethoxy)phenyl]ethyl]-4-(trifluoromethyl)-5-thiazolecarboxamide;
(63) N-[1-(3-bromophenyl)ethyl]-2-(2-methoxyphenyl)-4-(trifluoromethyl)-5-thiazolecarboxamide;
(64) 2-[3-(4-morpholinyl)phenyl]-N-[1-[3-(trifluoromethoxy)phenyl]ethyl]-4-(trifluoromethyl)-5-thiazolecarboxamide;
(65) 2-[3-(4-morpholinyl)phenyl]-4-(trifluoromethyl)-N-[1-[3-(trifluoromethyl)phenyl]ethyl]-5-thiazolecarboxamide;
(66) N-[(1S)-1-(3-methoxyphenyl)ethyl]-2-[3-(4-morpholinyl)phenyl]-4-(trifluoromethyl)-5-thiazolecarboxamide;
(67) 2-[2-[2-(diethylamino)ethoxy]phenyl]-N-[(1S)-1-[3-(4-morpholinyl)phenyl]ethyl]-4-(trifluoromethyl)-5-thiazolecarboxamide;
(68) 2-[2-[2-(diethylamino)ethoxy]phenyl]-N-[(1S)-1-(3-methoxyphenyl)ethyl]-4-(trifluoromethyl)-5-thiazolecarboxamide;
(69) N-[1-(3-aminophenyl)ethyl]-2-(2-fluorophenyl)-4-(trifluoromethyl)-5-thiazolecarboxamide;
(70) 2-[2-[2-(diethylamino)ethoxy]-5-fluorophenyl]-N-[1-[3-(trifluoromethoxy)phenyl]ethyl]-4-(trifluoromethyl)-5-thiazolecarboxamide;
(71) 2-[2-[(dimethylamino)methyl]phenyl]-4-(trifluoromethyl)-N-[1-[3-(trifluoromethyl)phenyl]ethyl]-5-thiazolecarboxamide;
(72) 2-[2-[(diethylamino)methyl]phenyl]-N-[1-[3-(4-morpholinylmethyl)phenyl]ethyl]-4-(trifluoromethyl)-5-thiazolecarboxamide;
(73) 2-[2-[(diethylamino)methyl]phenyl]-N-[1-[3-(3-pyridinyl)phenyl]ethyl]-4-(trifluoromethyl)-5-thiazolecarboxamide;
(74) 2-[2-(4-morpholinylmethyl)phenyl]-N-[1-[3-(trifluoromethoxy)phenyl]ethyl]-4-(trifluoromethyl)-5-thiazolecarboxamide;
(75) 2-[2-(4-morpholinylmethyl)phenyl]-N-[[3-(trifluoromethoxy)phenyl]methyl]-4-(trifluoromethyl)-5-thiazolecarboxamide;
(76) 2-[2-(4-morpholinylmethyl)phenyl]-N-[(1S)-1-[3-(4-morpholinyl)phenyl]ethyl]-4-(trifluoromethyl)-5-thiazolecarboxamide;
(77) 2-(3-fluorophenyl)-N-[(3-fluorophenyl)methyl]-4-(trifluoromethyl)-5-thiazolecarboxamide;
(78) N-[(1S)-1-(3-methoxyphenyl)ethyl]-2-[2-(4-morpholinylmethyl)phenyl]-4-(trifluoromethyl)-5-thiazolecarboxamide;
(79) N-[(1S)-1-(3-methoxyphenyl)ethyl]-2-[2-[(4-methyl-1-piperazinyl)methyl]phenyl]-4-(trifluoromethyl)-5-thiazolecarboxamide;
(80) 2-[2-[[ethyl(4-pyridinylmethyl)amino]methyl]phenyl]-N-[1-[3-(trifluoromethoxy)phenyl]ethyl]-4-(trifluoromethyl)-5-thiazolecarboxamide;
(81) 2-[2-[[ethyl(4-pyridinylmethyl)amino]methyl]phenyl]-N-[(3-methoxyphenyl)methyl]-4-(trifluoromethyl)-5-thiazolecarboxamide;
(82) 2-[2-[[ethyl(4-pyridinylmethyl)amino]methyl]phenyl]-N-[(1S)-1-[3-(4-morpholinyl)phenyl]ethyl]-4-(trifluoromethyl)-5-thiazolecarboxamide;
(83) 2-[2-[[ethyl(4-pyridinylmethyl)amino]methyl]phenyl]-N-[1-[3-(4-morpholinylmethyl)phenyl]ethyl]-4-(trifluoromethyl)-5-thiazolecarboxamide;
(84) 2-[2-[[ethyl(4-pyridinylmethyl)amino]methyl]phenyl]-N-[1-[3-(3-pyridinyl)phenyl]ethyl]-4-(trifluoromethyl)-5-thiazolecarboxamide;
(85) 2-(2-methylbenzoyl)-N-[1-[3-(trifluoromethoxy)phenyl]ethyl]-4-(trifluoromethyl)-5-thiazolecarboxamide;
(86) N-[1-[4-fluoro-3-(4-morpholinyl)phenyl]ethyl]-2-(2-methylbenzoyl)-4-(trifluoromethyl)-5-thiazolecarboxamide;
(87) 2-[3-[(diethylamino)methyl]-2-pyridinyl]-N-[1-[3-(trifluoromethoxy)phenyl]ethyl]-4-(trifluoromethyl)-5-thiazolecarboxamide;

(88) 2-[3-[[ethyl(4-pyridinylmethyl)amino]methyl]-2-pyridinyl]-N-[(1S)-1-[3-(4-morpholinyl)phenyl]ethyl]-4-(trifluoromethyl)-5-thiazolecarboxamide;

(89) 2-[3-[[ethyl(4-pyridinylmethyl)amino]methyl]-2-pyridinyl]-N-[1-[3-(4-morpholinylmethyl)phenyl]ethyl]-4-(trifluoromethyl)-5-thiazolecarboxamide;

(90) N-[(1S)-1-[3-[(2R,6S)-2,6-dimethyl-4-morpholinyl]phenyl]ethyl]-2-[3-(4-morpholinylmethyl)-2-pyridinyl]-4-(trifluoromethyl)-5-thiazolecarboxamide;

(91) N-[(1S)-1-[3-[(2R,6S)-2,6-dimethyl-4-morpholinyl]phenyl]ethyl]-2-[3-[[ethyl(1-methylethyl)amino]methyl]-2-pyridinyl]-4-(trifluoromethyl)-5-thiazolecarboxamide;

(92) N-[(1S)-1-[3-[(2R,6S)-2,6-dimethyl-4-morpholinyl]phenyl]ethyl]-2-[3-[[ethyl(4-pyridinylmethyl)amino]methyl]-2-pyridinyl]-4-(trifluoromethyl)-5-thiazolecarboxamide;

(93) 2-[3-(4-morpholinylmethyl)-2-pyridinyl]-N-[(1S)-1-[3-(3-pyridinyl)phenyl]ethyl]-4-(trifluoromethyl)-5-thiazolecarboxamide;

(94) 2-[3-[[ethyl(1-methylethyl)amino]methyl]-2-pyridinyl]-N-[(1S)-1-[3-(3-pyridinyl)phenyl]ethyl]-4-(trifluoromethyl)-5-thiazolecarboxamide;

(95) 2-[3-[[ethyl(4-pyridinylmethyl)amino]methyl]-2-pyridinyl]-N-[(1S)-1-[3-(3-pyridinyl)phenyl]ethyl]-4-(trifluoromethyl)-5-thiazolecarboxamide;

(96) 2-[3-[[ethyl(1-methylethyl)amino]methyl]-2-pyridinyl]-N-[1-[3-(trifluoromethoxy)phenyl]ethyl]-4-(trifluoromethyl)-5-thiazolecarboxamide;

(97) 2-[3-[(diethylamino)methyl]-2-pyridinyl]-4-(trifluoromethyl)-N-[1-[3-(trifluoromethyl)phenyl]ethyl]-5-thiazolecarboxamide;

(98) 2-[3-[[ethyl(1-methylethyl)amino]methyl]-2-pyridinyl]-4-(trifluoromethyl)-N-[1-[3-(trifluoromethyl)phenyl]ethyl]-5-thiazolecarboxamide;

(99) 2-(3-methyl-2-pyridinyl)-N-[(1S)-1-[3-(3-pyridinyl)phenyl]ethyl]-4-(trifluoromethyl)-5-thiazolecarboxamide;

(100) 2-(3-methyl-2-pyridinyl)-N-[(1S)-1-[3-(4-morpholinyl)phenyl]ethyl]-4-(trifluoromethyl)-5-thiazolecarboxamide;

(101) 2-[3-(1,3-dioxolan-2-yl)-2-pyridinyl]-N-[1-[3-(trifluoromethoxy)phenyl]ethyl]-4-(trifluoromethyl)-5-thiazolecarboxamide;

(102) 2-[3-[[ethyl(1-methylethyl)amino]methyl]-2-pyridinyl]-N-[(1S)-1-[3-(4-morpholinyl)phenyl]ethyl]-4-(trifluoromethyl)-5-thiazolecarboxamide;

(103) 2-[3-[[ethyl(4-pyridinylmethyl)amino]methyl]-2-pyridinyl]-N-[1-[3-(trifluoromethoxy)phenyl]ethyl]-4-(trifluoromethyl)-5-thiazolecarboxamide;

(104) 2-[3-(4-morpholinylmethyl)-2-pyridinyl]-4-(trifluoromethyl)-N-[1-[3-(trifluoromethyl)phenyl]ethyl]-5-thiazolecarboxamide;

(105) 2-benzo[b]thien-3-yl-N-[1-[3-(1-pyrrolidinylmethyl)phenyl]ethyl]-4-(trifluoromethyl)-5-thiazolecarboxamide;

(106) 2-(1,3-benzodioxol-5-yl)-N-[1-[3-(trifluoromethoxy)phenyl]ethyl]-4-(trifluoromethyl)-5-thiazolecarboxamide;

(107) N-[1-[3-[(diethylamino)methyl]phenyl]ethyl]-2-(1-naphthalenyl)-4-(trifluoromethyl)-5-thiazolecarboxamide; and (108) 2-(1,3-benzodioxol-5-yl)-4-(trifluoromethyl)-N-[1-[3-(trifluoromethyl)phenyl]ethyl]-5-thiazolecarboxamide;

and pharmaceutically acceptable salts and solvates of these compounds.

Synthetic Methods

The general procedures used to synthesize intermediates and the compounds of Formula I are illustrated in Schemes 1-4 and are described in detail in the Specific Embodiments section. Reasonable variations of the described procedures, which would be evident to one skilled in the art, are intended to be within the scope of the present invention.

Scheme 1 illustrates a general route to Formula I compounds. Bromothiazole III can be coupled to an aryl boronic acid under Suzuki conditions to provide compounds of Formula II. Although Scheme 1 employs an aryl boronic acid in the Suzuki coupling reaction, other aryl organometallic compounds, such as organostannanes, are well known to undergo transistion metal catalyzed couplings of this type. Hydrolysis of the ester moiety followed by amination of the resulting carboxylic acid generates compounds of Formula I.

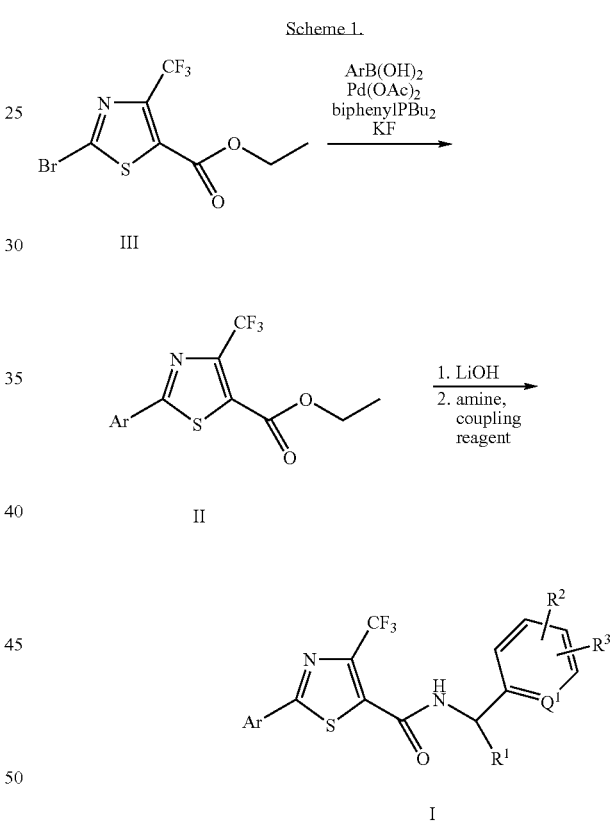

Scheme 2 illustrates the preparation of Formula Ib and Ic compounds. Methoxy compounds of Formula IIa, which encompass both phenyl and pyridyl moieties of $Ar^1$, are demethylated with boron tribromide to generate phenols of Formula IIb. These phenols can be transformed into Formula Ib compounds by alkylating with dibromoethane followed by amination with amines of Formula $HNR^6R^7$ to give thiazoles IId. Hydrolysis followed by amination as described before provides compounds of Formula Ib.

Phenols of Formula IIb can also be triflated followed by palladium catalyzed amination with $HNR^6R^7$ to generate thiazoles of Formula IIf. Hydrolysis and amination as described before provides compounds of Formula Ic.

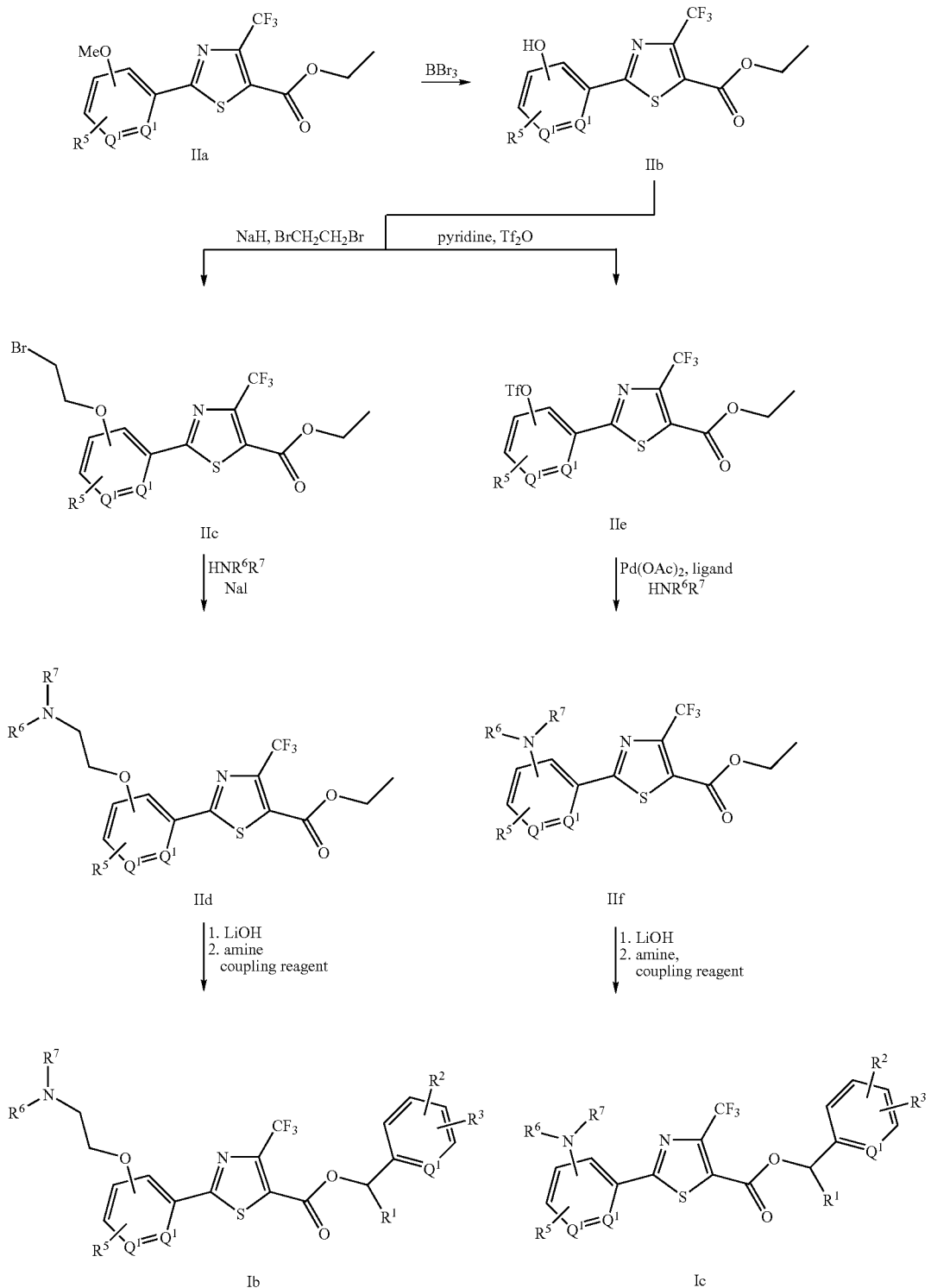

Scheme 3 provides a method for preparing compounds of Formula Id, Ie, and If. Aldehydic aryl bromides of Formula IV, which encompass both phenyl and pyridyl moieties of Ar$^1$, are protected as their ketals followed by transforming the aryl bromide moiety into an aryl stannane. The stannanes are coupled with thiazole III under Stille conditions to provide compounds of Formula IIg. Hydrolysis followed by amination as described before generates Formula Id compounds. The ketals are deprotected and reductively aminated to provide Formula If compounds.

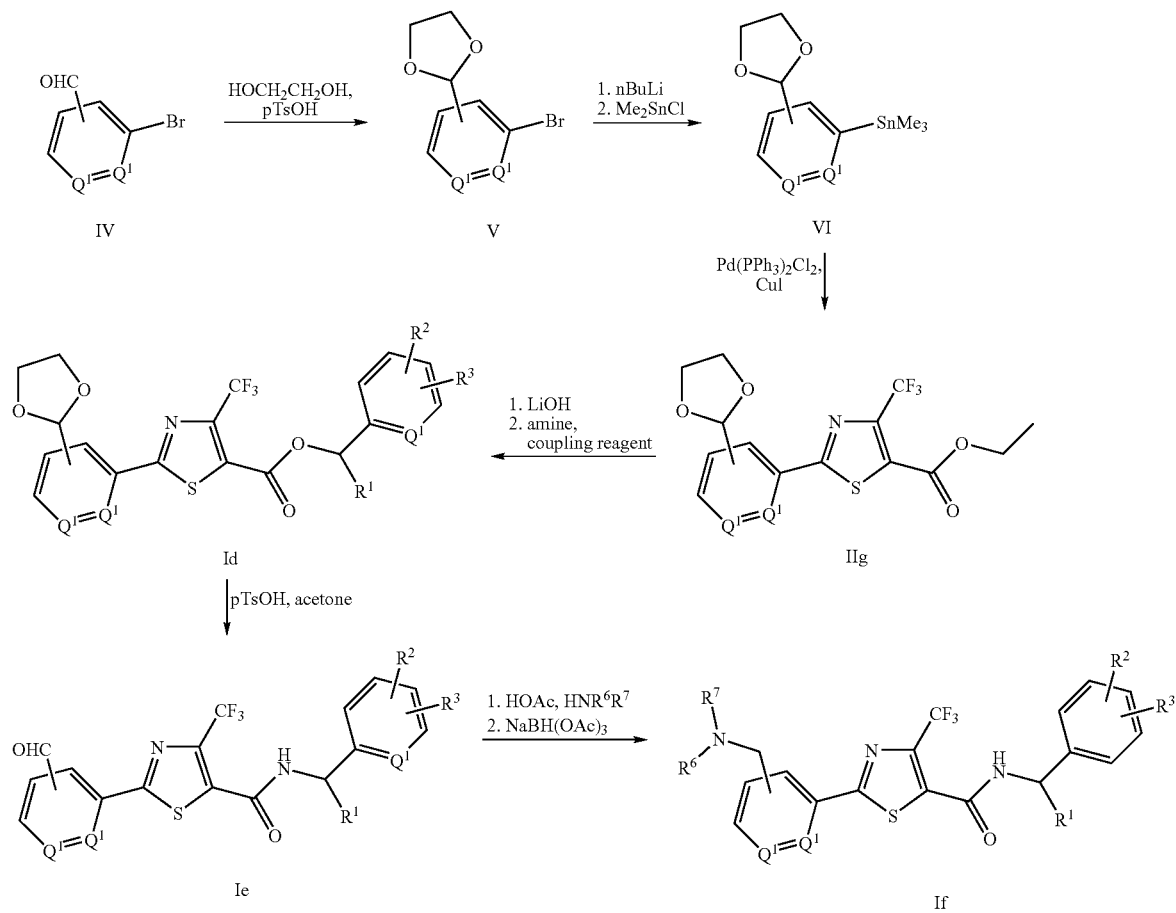

Scheme 4 illustrates an additional method for generating Formula If compounds. Compound IIh, prepared via Scheme 1 with a commercially available boronic acid, is cleaved with osmium tetroxide and periodate to generate aldehydes of Formula IIi. Reductive amination generates compounds of Formula IIj. Hydrolysis followed by amination as described before provides Formula If compounds.

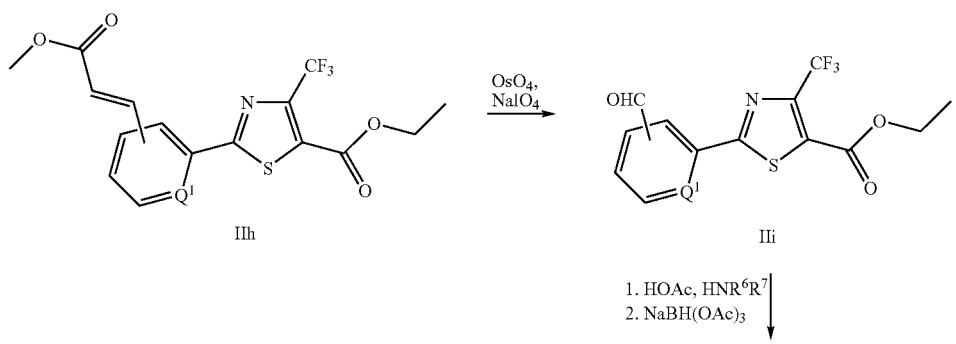

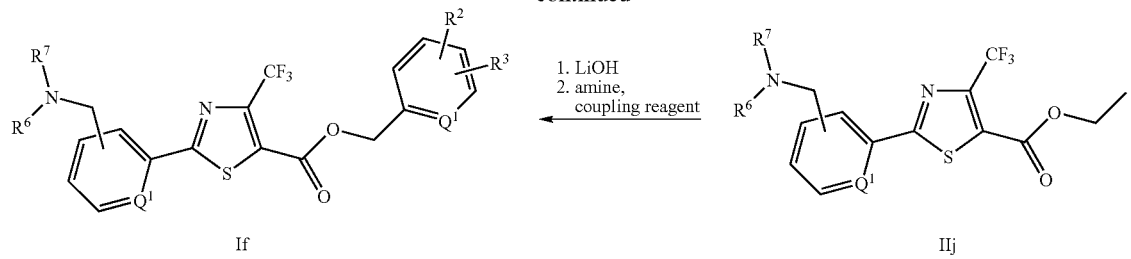

Biological Methods

Potassium (K+) channels are structurally and functionally diverse families of K+-selective channel proteins which are ubiquitous in cells, indicating their central importance in regulating a number of key cell functions [Rudy, B., Neuroscience, 25: 729-749 (1988)]. While widely distributed as a class, K+ channels are differentially distributed as individual members of this class or as families. [Gehlert, D. R., et al., Neuroscience, 52: 191-205 (1993)]. In general, activation of K+ channels in cells, and particularly in excitable cells such as neurons and muscle cells, leads to hyperpolarization of the cell membrane, or in the case of depolarized cells, to repolarization. In addition to acting as an endogenous membrane voltage clamp, K+ channels can respond to important cellular events such as changes in the intracellular concentration of ATP or the intracellular concentration of calcium ($Ca^{2+}$). The central role of K+ channels in regulating numerous cell functions makes them particularly important targets for therapeutic development. [Cook, N. S., Potassium channels: Structure, classification, function and therapeutic potential. Ellis Horwood, Chinchester (1990)]. One class of K+ channels, the KCNQ family exemplified by KCNQ2, KCNQ2/3 heteromultimers, and KCNQ5, is regulated by transmembrane voltage and plays a potentially important role in the regulation of neuronal excitability [Biervert, C., et al., Science, 279: 403-406 (1998); Lerche, C. et al., J. Biol. Chem. 275:22395-22400 (2000); Wang, H. et al., Science, 282:1890-1893 (1998)].

An opener of KCNQ channels, such as the KCNQ2 and KCNQ2/3 channel opener retigabine, exerts its cellular effects by increasing the open probability of these channels [Main J., Mol Pharmacol 58(2):253-62 (2000); Wickenden, A. et al., Mol. Pharm. 58:591-600 (2000)]. This increase in the opening of individual KCNQ channels collectively results in the hyperpolarization of cell membranes, particularly in depolarized cells, produced by significant increases in whole-cell KCNQ-mediated conductance.

Thallium Flux Assay for KCNQ channel Openers. The thallium assay is a modification of that published by Weaver and is referenced in its entirety (Weaver, C. D. WO 02/31508, 2002).

Approximately 20,000 cells/well of an HEK-293 cell line stably transfected with one of the members of the KCNQ family were plated into clear-bottom, black-walled, poly-D-lysine coated, 384 well assay plates in 20 µl/well of low chloride plating medium. Low chloride plating medium was composed of the following: sodium gluconate, 109 mM; potassium gluconate, 5.4 mM; hemi-calcium gluconate, 3.6 mM; magnesium sulfate, 0.8 mM; sodium bicarbonate, 26.2 mM; sodium phosphate monobasic, 1.2 mM; glutamine, 2 mM; glucose, 5 mM; 4-(2-hydroxyethyl)-1-piperazineethanesulfonic acid (HEPES) (pH 7.3) 10 mM, MEM vitamin solution (10× concentration of vitamins, Gibco/LifeTechnologies 11120-052) and MEM amino acid solution (1× concentration of amino acids, Gibco/LifeTechnologies 11130-051).

Following overnight incubation in a 5% $CO_2$ incubator at 37° C., the cells in the plates were loaded with 20 µl/well of a dye loading solution containing the commercially available thallium-sensitive fluorescent dye BTC-AM, the acetomethoxy ester of BTC (see U.S. Pat. No. 5,501,980) (2 µM) and pluronic acid F-127 (Molecular Probes P 6867) (0.02% w/v) in chloride free assay buffer. Chloride free assay buffer was composed of the following: sodium gluconate, 140 mM; potassium gluconate, 2.5 mM; hemi-calcium gluconate, 6 mM; hemi-magnesium gluconate, 2 mM; glucose, 5 mM; HEPES (pH 7.3), 10 mM.

Following incubation in the dye loading solution for from 45-90 min at room temperature, the dye loading solution was removed by aspiration and replaced with 40 µl/well of chloride free assay buffer.

Prior to addition to cell plates, test compound and standard compounds were dissolved in DMSO to 3 mM concentration. Compounds were then diluted from the 3 mM stock to 100-fold over the final assay concentration in DMSO. Finally, compounds in DMSO were diluted from 100-fold over the final assay concentration to 5-fold over the final assay concentration in chloride free assay buffer.

Ten µl/well of compounds at 5-fold over the final assay concentration were then added to the cell plates. This represents a 1:5 dilution, yielding the final test concentration. The wells used for test compounds were A1-P20. Wells A21-P22 contained a standard opener and a maximally efficacious concentration (positive control). Wells A23-P24 contained chloride free assay buffer containing 1% DMSO (negative control).

Following addition of test compounds, the plates were loaded onto the Molecular Devices FLIPR. The 488 nm line of the argon laser was used to excite the BTC and the emission filter was a 540(+/−30) nm. Images were collected at 1 Hz. Ten seconds of baseline were collected and then the FLIPR was used to add 13 µl/well of a stimulus buffer composed of 7.5 mM $Tl_2SO_4$ in chloride free assay buffer. Images were collected for an additional 60 seconds.

For data analysis, the amplitude of the average of the negative controls was subtracted from all wells. The amplitudes of the test compounds were then compared to the value of four standard deviations of the negative control wells. The lowest concentration of a test compound sufficient to generate a signal amplitude greater than or equal to four standard deviations from the amplitude of the negative controls was defined as the minimal active concentration.

For generating $EC_{50}$ values, compounds were serially diluted in 1:3 volume increments to produce a 10 point concentration series. $EC_{50}$ values were calculated by fitting the resulting amplitudes to a single-site logistic equation. EC$_{50}$ was defined as the concentration of test compound required to yield 50% of the maximal response. Maximal response (Maximal opening) was the largest signal amplitude divided by the negative control amplitude generated by any concentration of a test compound.

Table 1 describes the effect of representative Formula I compounds on KCNQ channels.

TABLE 1

| Example | Structure | Min. conc. response (μM) | EC$_{50}$ (μM) |
|---|---|---|---|
| 17 | (4-F-phenyl)-thiazole(CF$_3$)-C(O)NH-CH(CH$_3$)-(3-OCF$_3$-phenyl) | 0.3 | +++ |
| 18 | (2-OMe-phenyl)-thiazole(CF$_3$)-C(O)NH-CH(CH$_3$)-(3-OCF$_3$-phenyl) | 0.3 | +++ |
| 19 | (2-OMe-phenyl)-thiazole(CF$_3$)-C(O)NH-CH(CH$_3$)-(3-CF$_3$-phenyl) | 3 | +++ |
| 20 | (benzo[1,3]dioxol-5-yl)-thiazole(CF$_3$)-C(O)NH-CH(CH$_3$)-(3-OCF$_3$-phenyl) | 0.3 | + |
| 21 | (2-F-phenyl)-thiazole(CF$_3$)-C(O)NH-CH(CH$_3$)-(3-OCF$_3$-phenyl) | 0.3 | +++ |
| 22 | (2-F-phenyl)-thiazole(CF$_3$)-C(O)NH-CH(CH$_3$)-(3-CF$_3$-phenyl) | 0.3 | +++ |
| 23 | (2-OMe-phenyl)-thiazole(CF$_3$)-C(O)NH-CH(CH$_3$)-(3-morpholino-phenyl) | 3 | ++ |

TABLE 1-continued

| Example | Structure | Min. conc. response (μM) | EC$_{50}$ (μM) |
|---|---|---|---|
| 24 | 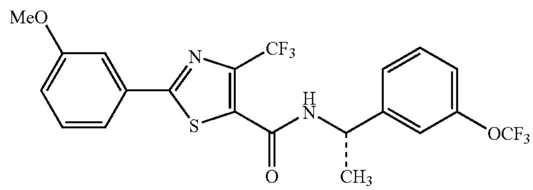 | 3 | ++ |
| 25 | 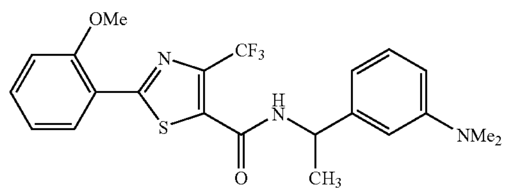 | 3 | + |
| 26 | 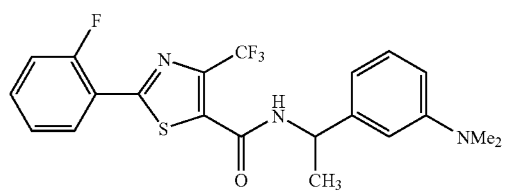 | 3 | ++ |
| 27 | 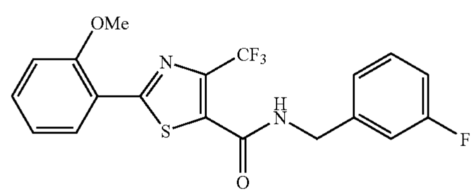 | 3 | + |
| 28 | 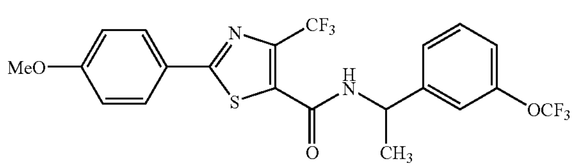 | 10 | + |
| 29 | 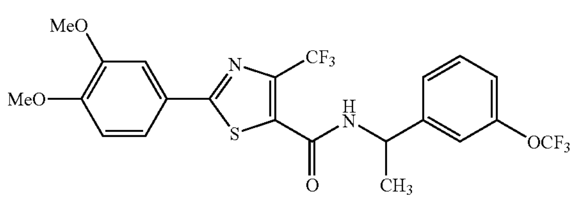 | 3 | ++ |
| 30 | 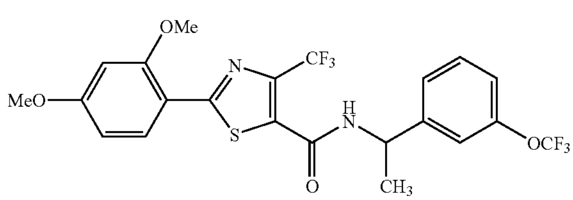 | 3 | ++ |

TABLE 1-continued

| Example | Structure | Min. conc. response (μM) | EC$_{50}$ (μM) |
|---|---|---|---|
| 31 | 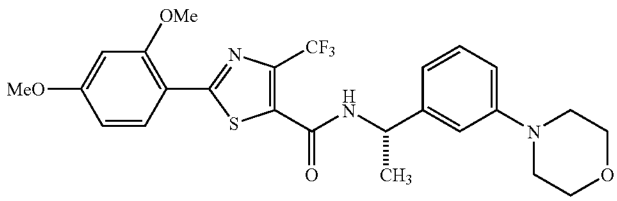 | 3 | + |
| 32 | 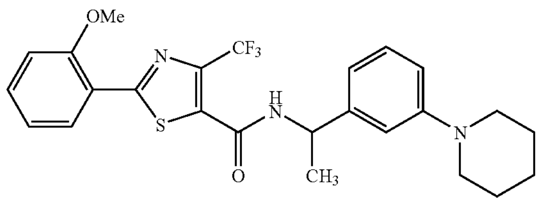 | 0.3 | +++ |
| 33 | 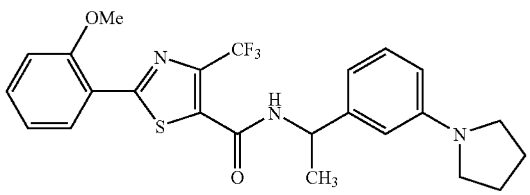 | 3 | ++ |
| 34 | 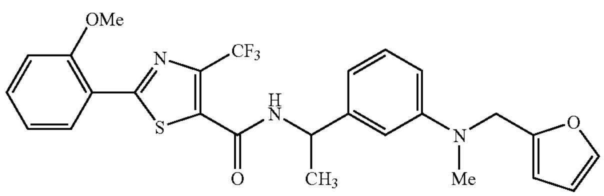 | 0.3 | +++ |
| 35 | 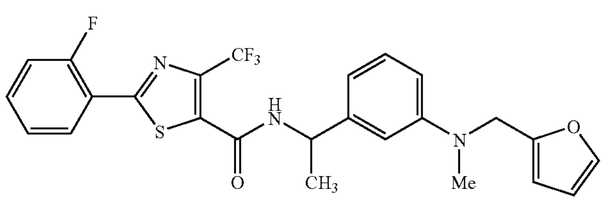 | 0.3 | ++ |
| 36 | 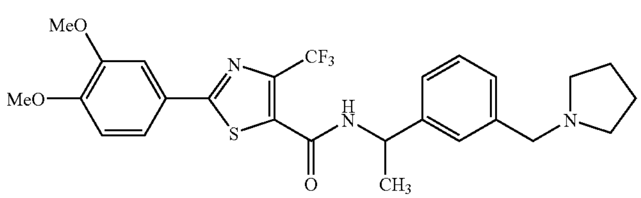 | 10 | + |
| 37 | 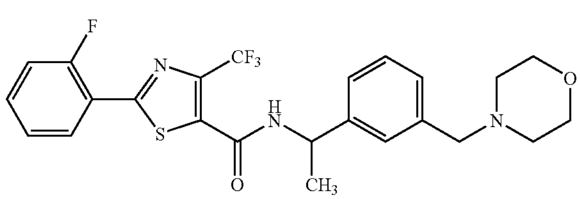 | 3 | + |

TABLE 1-continued

| Example | Structure | Min. conc. response (μM) | EC$_{50}$ (μM) |
|---|---|---|---|
| 38 | 2-(naphthalen-1-yl)-4-(trifluoromethyl)-N-(1-(3-((diethylamino)methyl)phenyl)ethyl)thiazole-5-carboxamide | 30 | + |
| 39 | 2-(2-methoxyphenyl)-4-(trifluoromethyl)-N-(1-(3-aminophenyl)ethyl)thiazole-5-carboxamide | 10 | + |
| 40 | 2-(2-methoxyphenyl)-4-(trifluoromethyl)-N-(1-(3-guanidinophenyl)ethyl)thiazole-5-carboxamide | 30 | + |
| 41 | 2-(2-methoxy-5-fluorophenyl)-4-(trifluoromethyl)-N-(1-(3-(trifluoromethoxy)phenyl)ethyl)thiazole-5-carboxamide | 10 | ++ |
| 42 | 2-(2-methoxy-5-fluorophenyl)-4-(trifluoromethyl)-N-(1-(3-(dimethylamino)phenyl)ethyl)thiazole-5-carboxamide | 10 | ++ |
| 43 | 2-(2-methoxy-5-fluorophenyl)-4-(trifluoromethyl)-N-(1-(3-(trifluoromethyl)phenyl)ethyl)thiazole-5-carboxamide | 3 | ++ |
| 44 | 2-(2-methoxy-5-fluorophenyl)-4-(trifluoromethyl)-N-(3-fluorobenzyl)thiazole-5-carboxamide | 3 | ++ |

TABLE 1-continued

| Example | Structure | Min. conc. response (μM) | EC$_{50}$ (μM) |
|---|---|---|---|
| 45 | 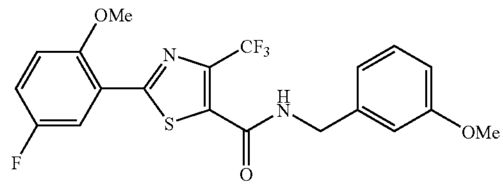 | 3 | + |
| 46 | 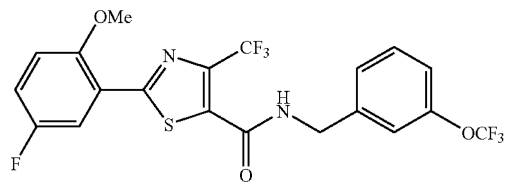 | 10 | + |
| 47 | 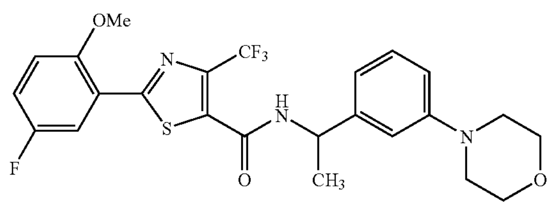 | 3 | + |
| 48 | 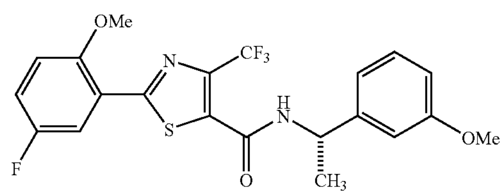 | 3 | ++ |
| 49 | 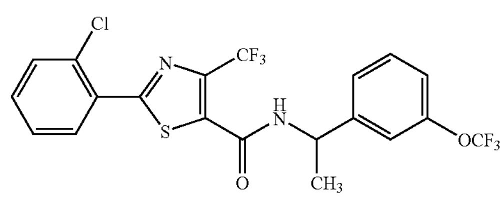 | 0.3 | ++ |
| 50 | 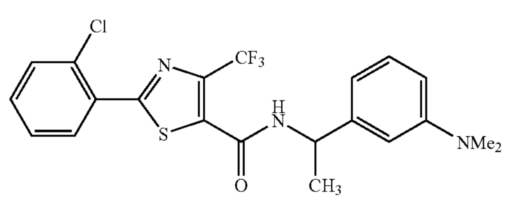 | 0.3 | ++ |
| 51 | 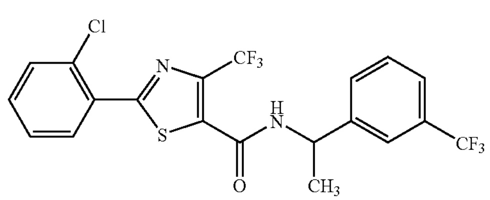 | 0.3 | ++ |

TABLE 1-continued

| Example | Structure | Min. conc. response (μM) | EC$_{50}$ (μM) |
|---|---|---|---|
| 52 | 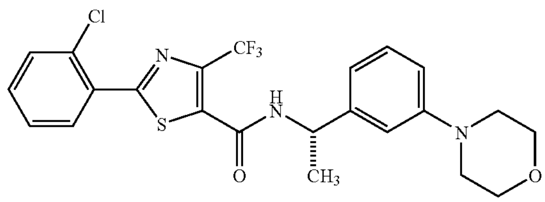 | 3 | ++ |
| 53 | 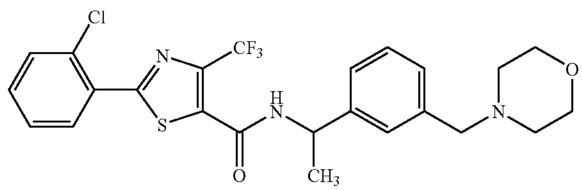 | 3 | + |
| 54 | 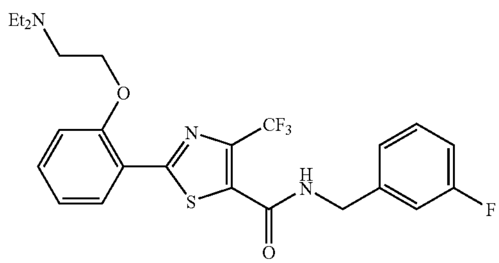 | 0.3 | + |
| 55 | 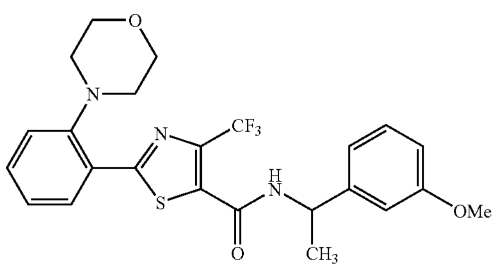 | 0.3 | + |
| 56 | 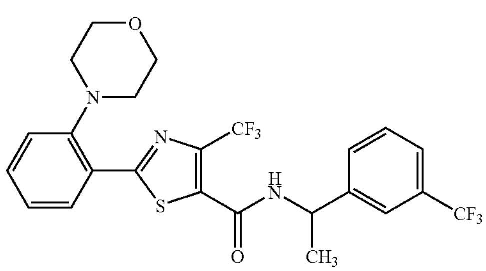 | 0.3 | ++ |
| 57 | 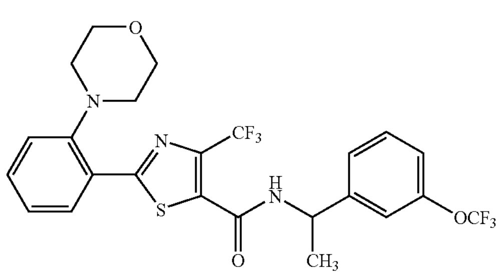 | 0.3 | ++ |

TABLE 1-continued

| Example | Structure | Min. conc. response (μM) | EC$_{50}$ (μM) |
|---|---|---|---|
| 58 | 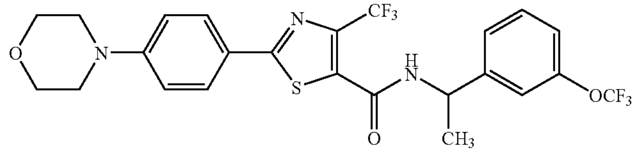 | 30 | ++ |
| 59 | 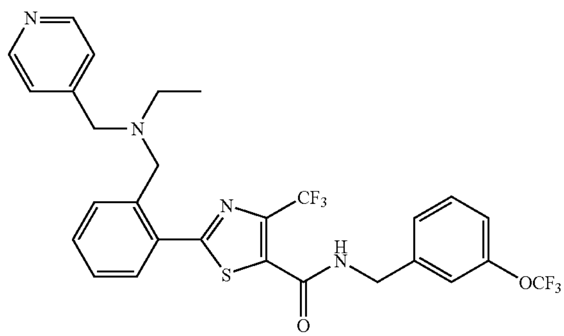 | 3 | ++ |
| 60 | 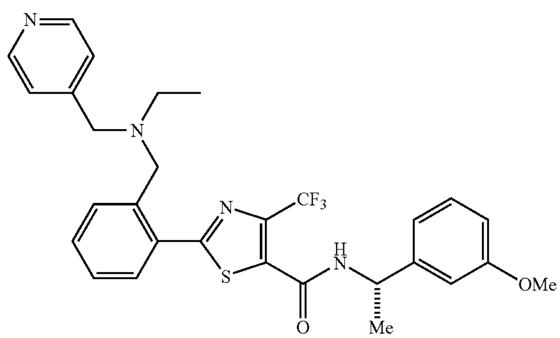 | 0.3 | ++ |
| 61 | 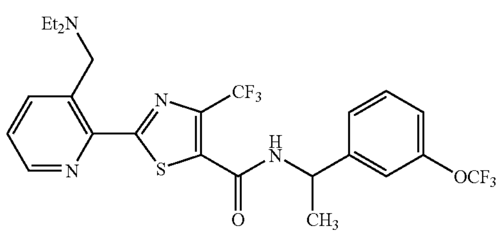 | 30 | ++ |
| 62 | 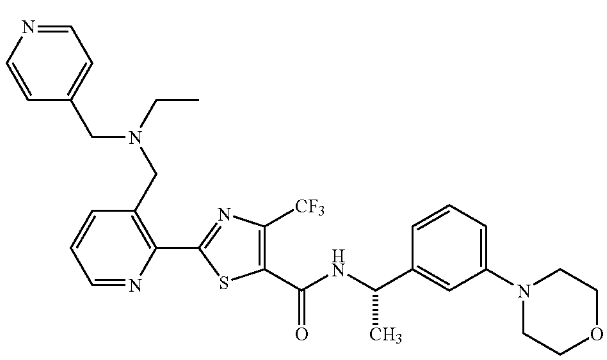 | 3 | ++ |

TABLE 1-continued
| Example | Structure | Min. conc. response (μM) | EC$_{50}$ (μM) |
|---|---|---|---|
| 63 | 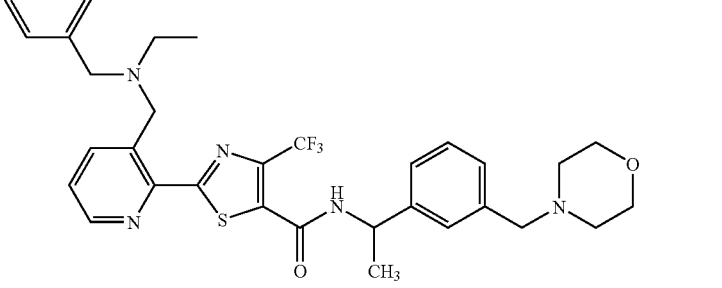 | 30 | ++ |
| 64 | 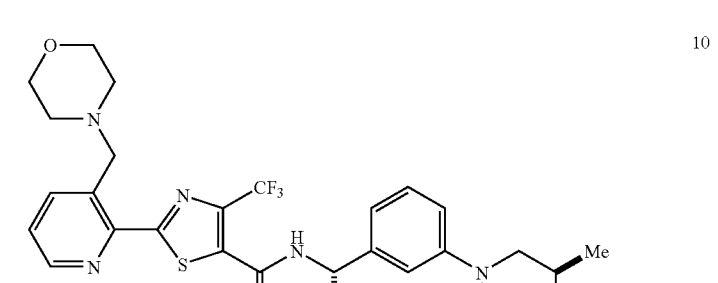 | 10 | ++ |
| 65 | 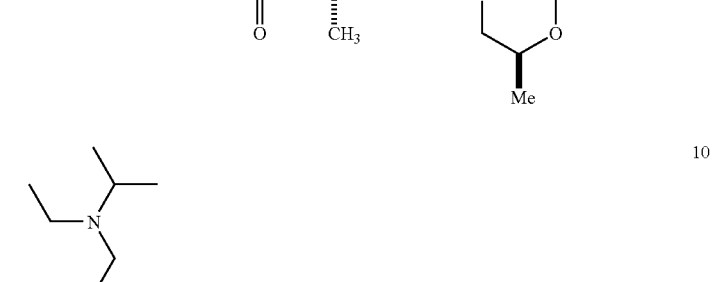 | 10 | ++ |
| 66 | 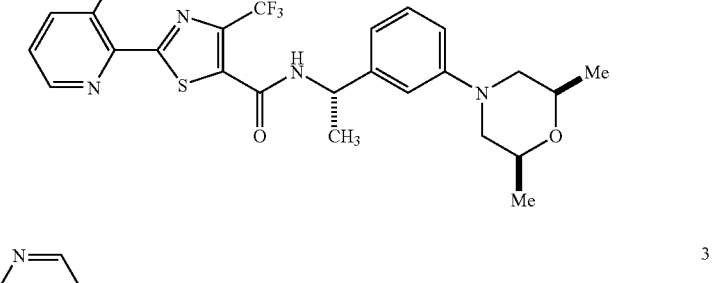 | 3 | ++ |

TABLE 1-continued

| Example | Structure | Min. conc. response (μM) | EC$_{50}$ (μM) |
|---|---|---|---|
| 67 | 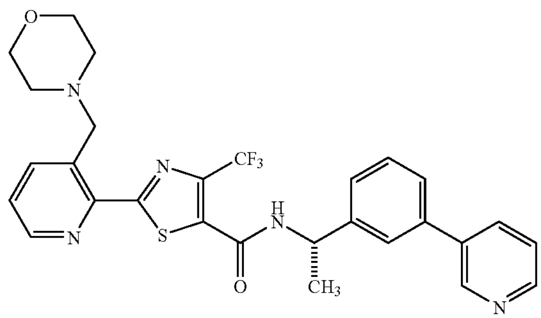 | 30 | ++ |
| 68 | 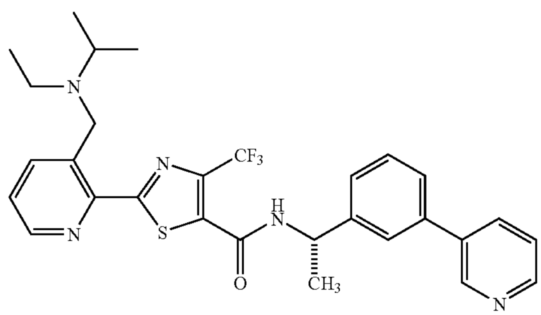 | 30 | + |
| 69 | 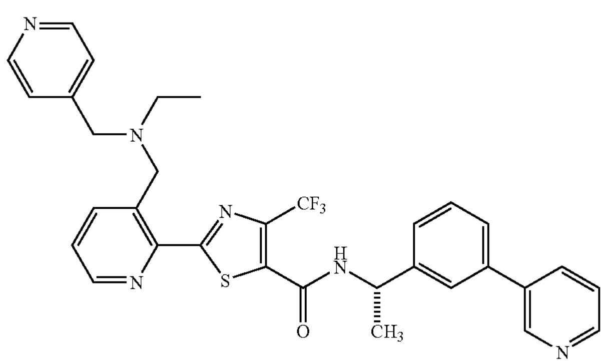 | 3 | ++ |
| 70 | 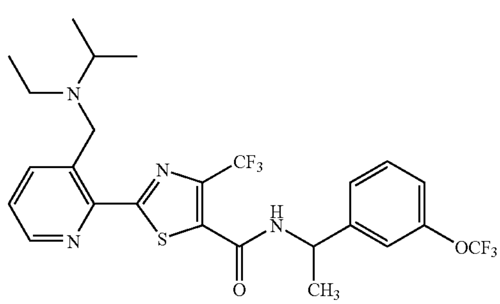 | 3 | ++ |
| 71 | 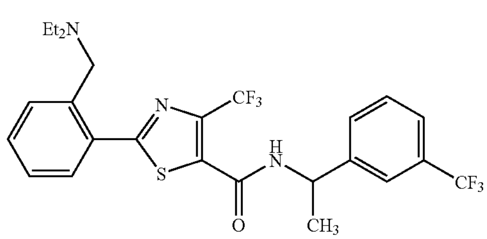 | 30 | ++ |

TABLE 1-continued

| Example | Structure | Min. conc. response (μM) | EC$_{50}$ (μM) |
|---|---|---|---|
| 72 | 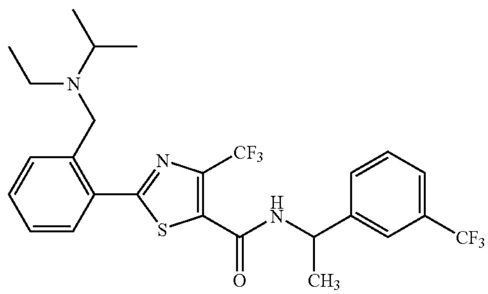 | 3 | ++ |
| 73 | 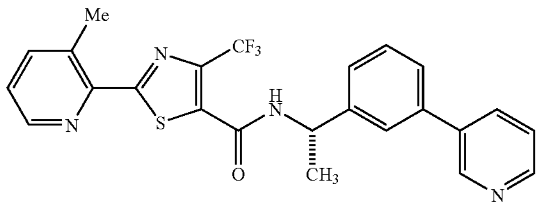 | 0.3 | ++ |
| 74 | 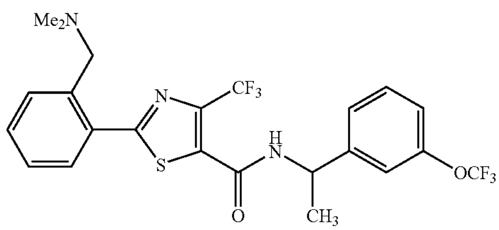 | 3 | + |
| 75 | 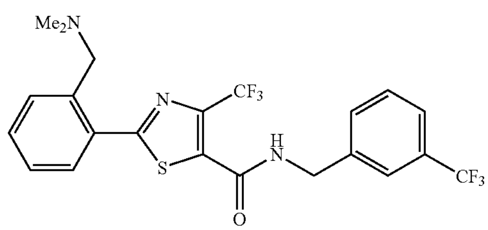 | 30 | ++ |
| 76 | 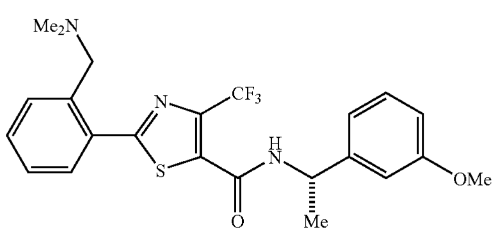 | 10 | ++ |
| 77 | 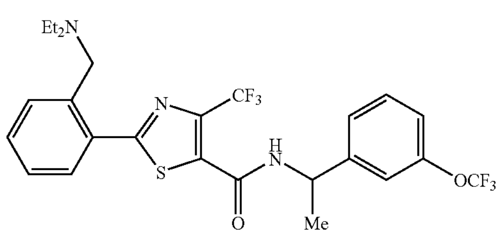 | 0.3 | + |

TABLE 1-continued

| Example | Structure | Min. conc. response (μM) | EC$_{50}$ (μM) |
|---|---|---|---|
| 78 | (Et$_2$NCH$_2$-phenyl)-thiazole(CF$_3$)-C(O)NH-CH(Me)-(3-CF$_3$-phenyl) | 3 | ++ |
| 79 | (Et$_2$NCH$_2$-phenyl)-thiazole(CF$_3$)-C(O)NH-CH$_2$-(3-F-phenyl) | 3 | ++ |
| 80 | (Et$_2$NCH$_2$-phenyl)-thiazole(CF$_3$)-C(O)NH-CH$_2$-(3-OCF$_3$-phenyl) | 3 | + |
| 81 | (Et$_2$NCH$_2$-phenyl)-thiazole(CF$_3$)-C(O)NH-CH(Me)-(3-morpholino-phenyl) | 30 | ++ |
| 82 | (Et$_2$NCH$_2$-phenyl)-thiazole(CF$_3$)-C(O)NH-CH(Me)-(3-OMe-phenyl) | 0.3 | ++ |
| 83 | (4-F-phenyl)-thiazole(CF$_3$)-C(O)NH-CH(CH$_3$)-(3-CF$_3$-phenyl) | 0.3 | na |
| 84 | (2-OMe-phenyl)-thiazole(CF$_3$)-C(O)NH-CH$_2$-(2-pyridyl) | 30 | na |

TABLE 1-continued

| Example | Structure | Min. conc. response (μM) | EC$_{50}$ (μM) |
|---|---|---|---|
| 85 | 2-(3-methoxyphenyl)-4-(trifluoromethyl)-N-(3-fluorobenzyl)thiazole-5-carboxamide | 30 | na |
| 86 | 2-(3-methoxyphenyl)-4-(trifluoromethyl)-N-(1-(2,3-dihydrobenzofuran-5-yl)ethyl)thiazole-5-carboxamide | 3 | na |
| 87 | 2-(benzo[d][1,3]dioxol-5-yl)-4-(trifluoromethyl)-N-(1-(3-(trifluoromethyl)phenyl)ethyl)thiazole-5-carboxamide | 0.3 | na |
| 88 | 2-(3-methoxyphenyl)-4-(trifluoromethyl)-N-(pyridin-2-ylmethyl)thiazole-5-carboxamide | 30 | na |
| 89 | 2-(3,4-dimethoxyphenyl)-4-(trifluoromethyl)-N-(1-(3-(trifluoromethyl)phenyl)ethyl)thiazole-5-carboxamide | 30 | na |
| 90 | 2-(3,4-dimethoxyphenyl)-4-(trifluoromethyl)-N-(1-(3,4-dimethoxyphenyl)ethyl)thiazole-5-carboxamide | 10 | na |
| 91 | 2-(3,4-dimethoxyphenyl)-4-(trifluoromethyl)-N-(3-(trifluoromethoxy)benzyl)thiazole-5-carboxamide | 30 | na |

TABLE 1-continued

| Example | Structure | Min. conc. response (μM) | EC$_{50}$ (μM) |
|---|---|---|---|
| 92 | 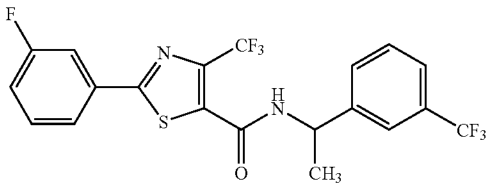 | 3 | na |
| 93 | 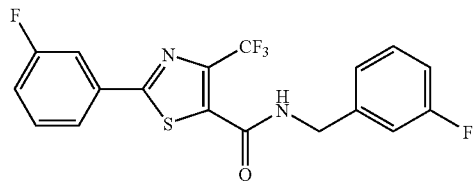 | 10 | na |
| 94 | 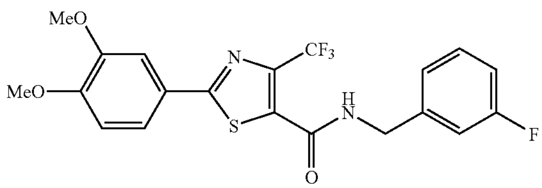 | 30 | na |
| 95 | 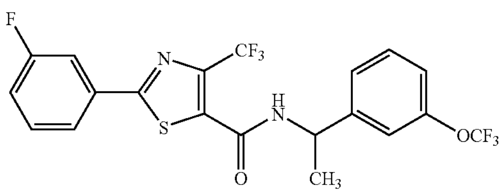 | 0.3 | na |
| 96 | 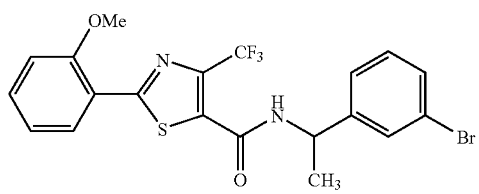 | 3 | na |
| 97 | 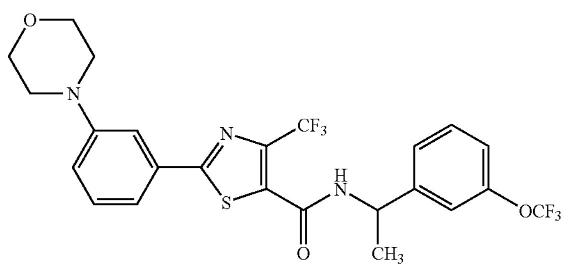 | 10 | na |
| 98 | 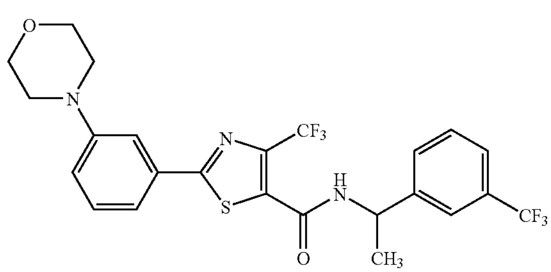 | 3 | na |

TABLE 1-continued

| Example | Structure | Min. conc. response (μM) | EC$_{50}$ (μM) |
|---|---|---|---|
| 99 | 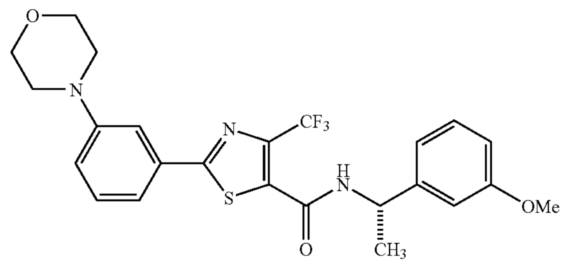 | 3 | na |
| 100 | 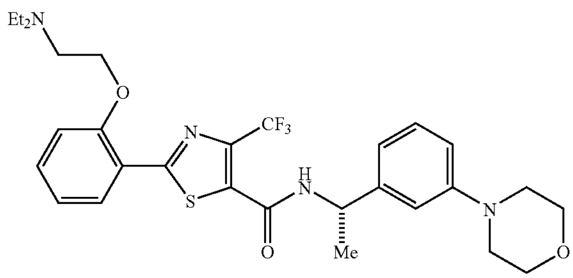 | 30 | na |
| 101 | 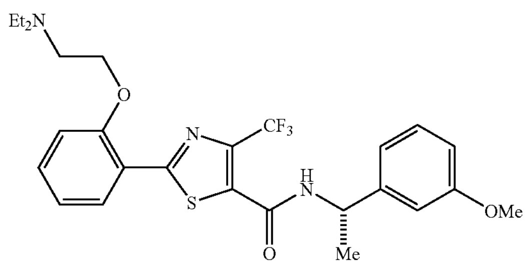 | 3 | na |
| 102 | 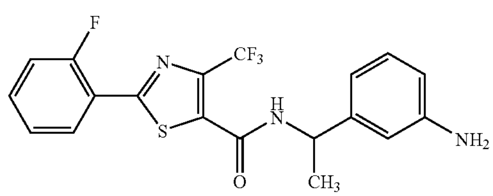 | 0.3 | na |
| 103 | 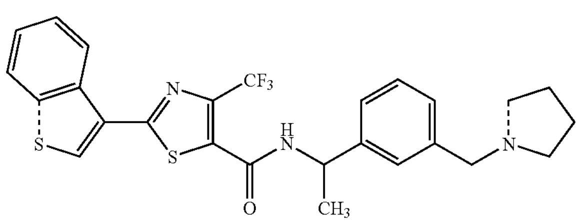 | 0.3 | na |
| 104 | 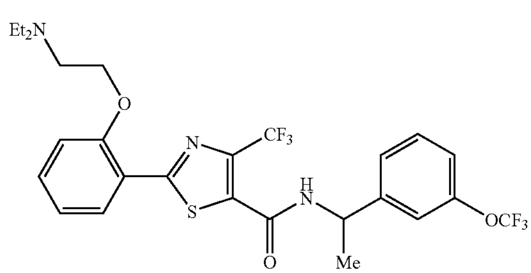 | 10 | na |

TABLE 1-continued

| Example | Structure | Min. conc. response (μM) | EC$_{50}$ (μM) |
|---|---|---|---|
| 105 | 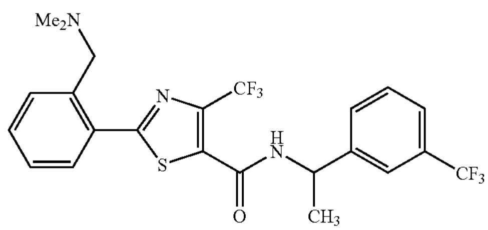 | 30 | na |
| 106 | 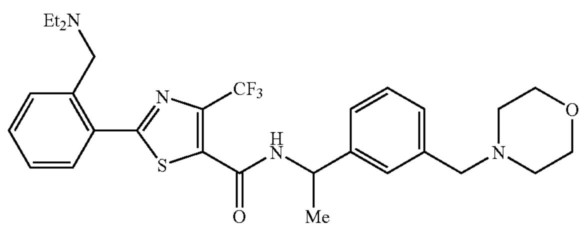 | 10 | na |
| 107 | 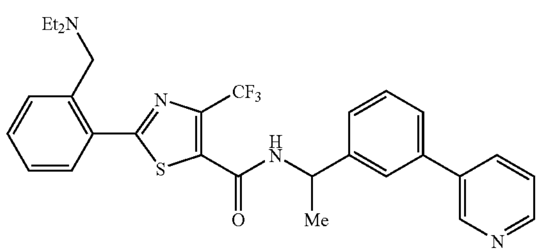 | 30 | na |
| 108 | 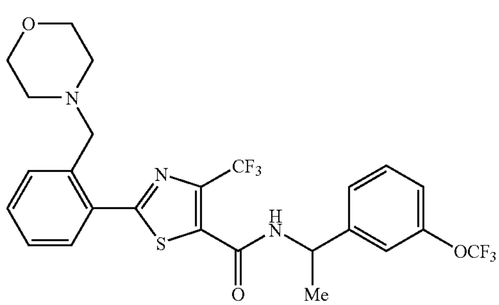 | 0.3 | na |
| 109 | 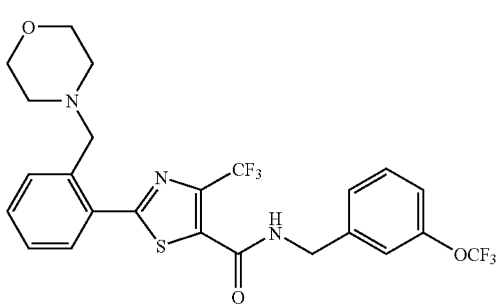 | 3 | na |

TABLE 1-continued

| Example | Structure | Min. conc. response (μM) | EC$_{50}$ (μM) |
|---|---|---|---|
| 110 | 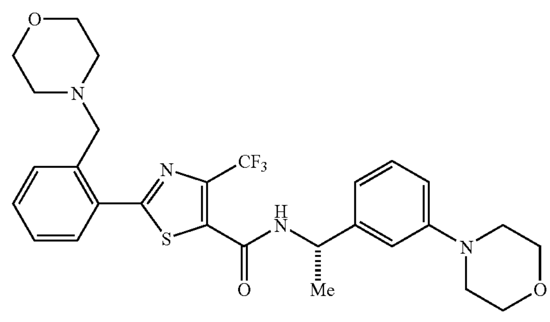 | 3 | na |
| 111 | 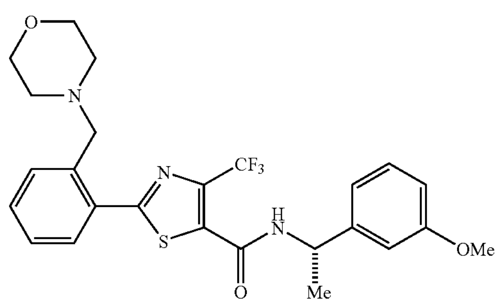 | 0.3 | na |
| 112 | 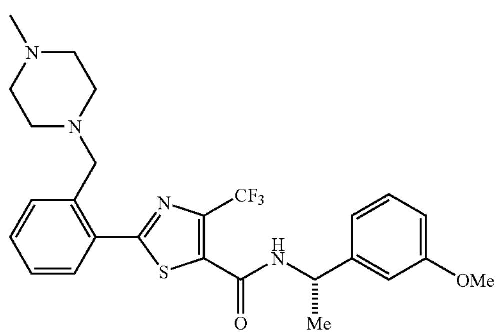 | 30 | na |
| 113 | 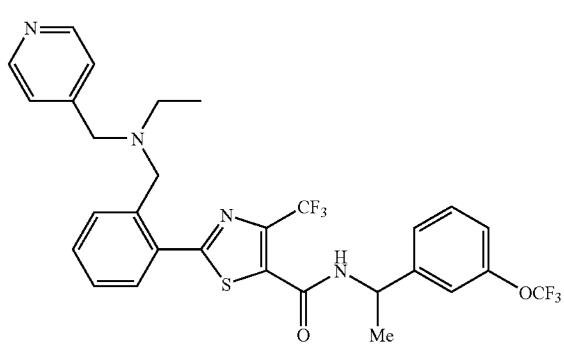 | 0.3 | na |

TABLE 1-continued
| Example | Structure | Min. conc. response (μM) | EC50 (μM) |
|---|---|---|---|
| 114 | 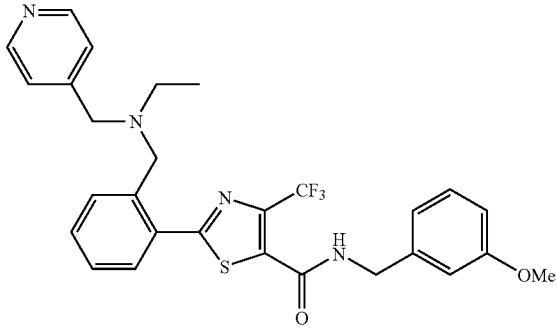 | 3 | na |
| 115 | 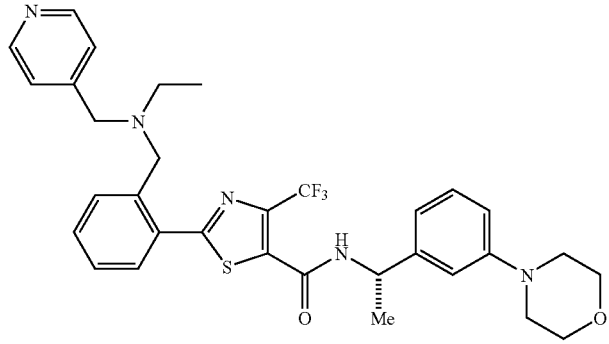 | 3 | na |
| 116 | 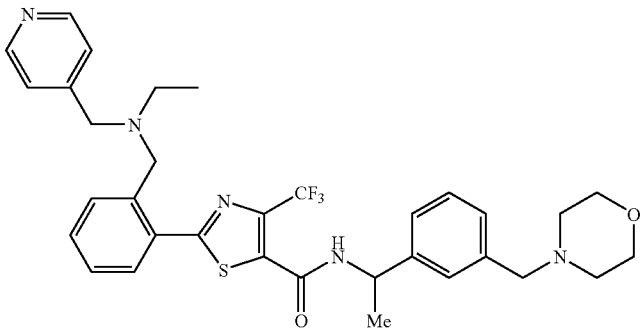 | 3 | na |
| 117 | 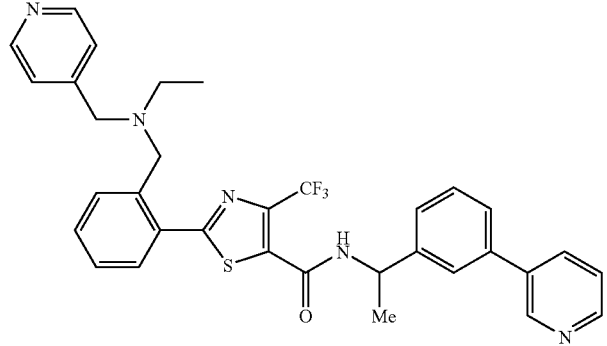 | 0.3 | na |

TABLE 1-continued

| Example | Structure | Min. conc. response (μM) | EC$_{50}$ (μM) |
|---------|-----------|--------------------------|----------------|
| 118 | 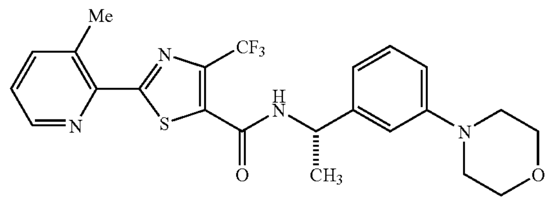 | 10 | na |
| 119 | 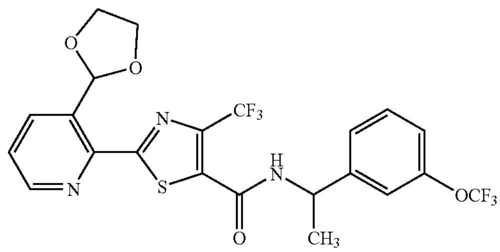 | 3 | na |
| 120 | 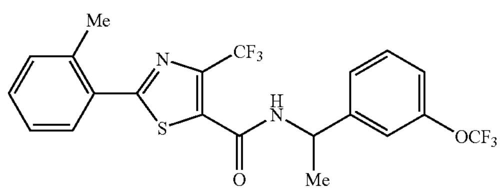 | 0.3 | +++ |
| 121 | 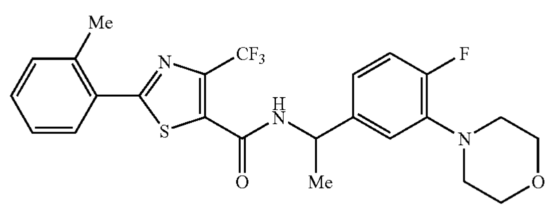 | 3 | + |
| 122 | 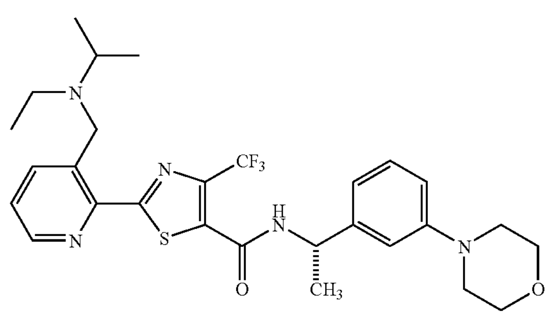 | 30 | na |
| 123 | 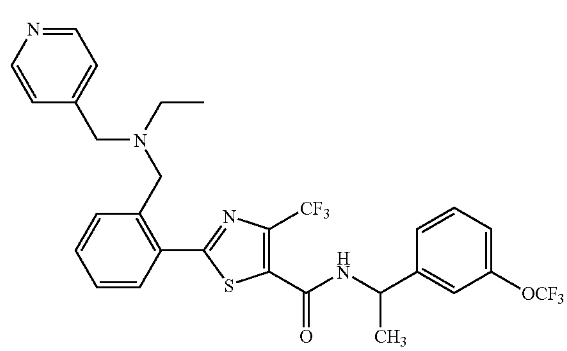 | 3 | na |

TABLE 1-continued

| Example | Structure | Min. conc. response (µM) | EC$_{50}$ (µM) |
|---|---|---|---|
| 124 | (structure: morpholine-CH2-pyridine-thiazole(CF3)-C(O)NH-CH(CH3)-phenyl-CF3) | 3 | na |

EC$_{50}$ values: +++ = <50 nM, ++ = 50-1000 nM, + = 1000-20000 nM.

KCNQ Patch-clamp. Whole-cell patch-clamp recordings were made from an HEK 293 stable cell line expressing mKCNQ2 channels, maintained in culture for 1-2 days. Patch pipettes had initial resistances of 2.5-4 MΩ. Currents were recorded with an EPC-9 amplifier (HEKA, Lambrecht, Germany) controlled with software (Pulse, HEKA) run on a standard lab PC. Series resistance compensation was used during current recording, and set at 80%. The series resistance (R) and cell capacitance (C) were determined electronically by subtracting the capacitive currents at the onset and offset of a 5 mV voltage step. The cancellation of whole-cell capacitive transients was virtually complete in all cells. Analog current signals were low-pass filtered at 2.9 kHz using a four-pole Bessel filter −3 dB) and stored on a local network server computer at a sampling rate of 1.5 kHz. All recordings were performed at room temperature (20-22° C.). The pipette solution contained (mM) KCl, 150; CaCl$_2$, 2.5; EGTA, 5; MgCl$_2$, 1; HEPES, 10; pH to 7.3 with KOH, and Osmolality of 290-300 mOsm. The extracellular solution contained (mM): NaCl, 140; KCl, 2.5; CaCl$_2$, 2.5; MgCl$_2$, 1; glucose, 10; HEPES, 10; pH to 7.3 with NaOH, and Osmolality of 305-310 mOsm.

For analysis of agents effects on mKCNQ2 currents, the raw current records were displayed on the digital oscilloscope of the Pulse software application. Concentration response data were generated by measuring the difference in the steady-state amplitude of current in the presence of compound at the end of a 600 ms voltage-clamp step from a holding potential of −80 mV. The concentration-response data were fitted with Hill-type equations:

$$I = I_{max}/(1+EC_{50}/[A]^{nH}),$$

where I is the steady-state current at a given concentration of agonist [A]; and $I_{max}$, $EC_{50}$ and nH are parameters estimated from the curve fit. In some cases the concentration-response data were fitted with equations consisting of the sum of two Hill-type components. Current-voltage (I/V) relationships for agonist-evoked currents were obtained by performing 600 ms voltage steps (−110 mV to +40 mV) in the absence and presence of agonist.

Example 21 was verified in a patch-clamp assay measuring the effect of compounds on the current of KCNQ2 channels. The compound exhibited an EC$_{50}$ of 3.0 nM, demonstrating that this compound opened the KCNQ2 channel.

Chung model of neuropathic pain (Chung surgery and von Frey test). To test agents for activity against peripheral mononeuropathy nerve injury-induced tactile allodynia, male Sprague Dawley rats (wt. 120-160 g) were surgically prepared with unilateral tight ligation of spinal nerves L5 and L6 following the method of Kim and Chung (Kim S. H., Chung J. M. (1992) Pain, September; 50(3):355-63). After 3-4 weeks recovery, paw withdrawal to light touch was assessed as described by Chaplan et al. (Chaplan S. R., et al., (1994) J. Neurosci Methods, July; 53(1):55-63). In brief, rats are placed in a plastic cage with a wire mesh bottom and allowed to acclimate for 15-30 minutes, until cage exploration and grooming stops. The plantar surface of each hind paw is touched with a series of von Frey hairs with varying stiffness requiring a known force to buckle to determine the nociceptive threshold. Adult male Sprague Dawley rats (avg. wt. 340 g) were tested in the present study. After acclimation, baseline von Frey thresholds were assessed for the injured hindpaw at −15 min. Test compounds were delivered at 0 min by the intravenous (i.v.) route in a volume of 0.5-2 ml/kg. The vehicle for test compounds was 100% PEG-400. For gabapentin the vehicle was deionized H$_2$O. Animals were tested in one of the following 4 treatment conditions: (a) PEG400, (b) gabapentin (Neurontin) 100 mg/kg, (c) test compounds 3 mg/kg and (d) test compounds 10 mg/kg. Following drug administration, von Frey thresholds were measured at 15, 30, 60 and 90 min. Data were analyzed by a 2-way repeated measures analysis of variance followed by Dunnett's test (p<0.05). Experimenters were kept blind to the treatment condition of rats they tested.

Reversal of neuropathic pain behavior may be expressed as a percentage (0-100%) of the maximum possible effect, over and above the vehicle effects. Specifically, drug effects can be described in terms Δ% MPE according to the following equation:

$$\Delta\%\ MPE = \left(\frac{(AUCdrug - AUCvehicle)}{((Time \times Max) - AUCvehicle)}\right) \times 100$$

where:

AUCdrug=area under the curve for von Frey thresholds of the drug-treated group;

AUCvehicle=area under the curve for von Frey thresholds in the vehicle group;

Time=duration of post-drug testing period (90 min); and Max=maximum von Frey threshold (15 g).

For example, a compound which immediately reversed neuropathic pain behavior to normal levels, such that animals only responded to the highest von Frey filament (15 g), and maintained normal levels through out the post-drug testing period (90 min) would be calculated as Δ% MPE=100%.

The results for example 21 are provided in the following Table 2.

TABLE 2

| Compound | AUC (Δ % MPE)* |
|---|---|
| Gabapentin | 50 (100 mg/kg, i.v.) |
| Example 21 | 28 (10 mg/kg, i.v.) |

*Δ % MPE = % MPE (Drug AUC) − % MPE (Vehicle AUC)

Diabetic model of neuropathic pain (Streptozoticin & von Frey test). To test agents for activity against systemic polyneuropathy nerve injury-induced tactile allodynia, animals were treated with streptozoticin (STZ) to create a diabetic condition by selective cytotoxic action upon pancreatic β-islet cells that produce insulin following the method of Courteix, et al. (Courteix C., et al., (1993) *Pain*, April; 53(1):81-8). In brief, male Sprague Dawley rats (wt. 200-275 g) received an injection of STZ (75 mg/kg, i.p.) and diabetes was confirmed three weeks after STZ injection by measurement of tail vein blood glucose levels. After 3-4 weeks, paw withdrawal to light touch was assessed as described by Chaplan et al. (Chaplan S. R., et al., (1994) *J Neurosci Methods*, July; 53(1):55-63). In brief, rats are placed in a plastic cage with a wire mesh bottom and allowed to acclimate for 15-30 minutes, until cage exploration and grooming stops. The plantar surface of each hind paw is touched with a series of von Frey hairs with varying stiffness requiring a known force to buckle to determine the nociceptive threshold. Adult male Sprague Dawley rats (avg. wt. 300 g) were tested in the present study. After acclimation, baseline von Frey thresholds were assessed for the injured hindpaw at −15 min. All test compounds were delivered at 0 min by the intravenous (i.v.) route in a volume of 0.5-2 ml/kg. The vehicle for the compounds of Formula I was 100% PEG-400. For gabapentin the vehicle was deionized $H_2O$. Animals were tested in one of the following 4 treatment conditions: (a) PEG400, (b) gabapentin (Neurontin) 200 mg/kg, (c) test compounds 10 mg/kg and (d) test compounds 30 mg/kg. Following drug administration, von Frey thresholds were measured at 15, 30, 60 and 90 min. Data were analyzed by a 2-way repeated measures analysis of variance followed by Dunnett's test (p<0.05). Experimenters were kept blind to the treatment condition of rats they tested.

Reversal of neuropathic pain behavior may be expressed as a percentage (0-100%) of the maximum possible effect, over and above the vehicle effects. Specifically, drug effects can be described in terms Δ% MPE according to the following equation:

$$\Delta \% \ MPE = \left( \frac{(AUCdrug - AUCvehicle)}{((Time \times Max) - AUCvehicle)} \right) \times 100$$

where: AUCdrug=area under the curve for von Frey thresholds of the drug-treated group; AUCvehicle=area under the curve for von Frey thresholds in the vehicle group; Time=duration of post-drug testing period (90 min); and Max=maximum von Frey threshold (15 g).

For example, a compound which immediately reversed neuropathic pain behavior to normal levels, such that animals only responded to the highest von Frey filament (15 g), and maintained normal levels through out the post-drug testing period (90 min) would be calculated as Δ% MPE=100%.

The results for example 21 are provided in the following Table 3.

TABLE 3

| Compound | AUC (Δ % MPE)* |
|---|---|
| Example 21 | 28 (10 mg/kg, i.v.) |

*Δ % MPE = % MPE (Drug AUC) − % MPE (Vehicle AUC)

These results suggest that compounds of Formula I are efficacious in reducing neuropathic pain including pain associated with diabetic neuropathy.

Pharmaceutical Composition and Methods of Treatment

Another aspect of this invention includes pharmaceutical compositions comprising at least one compound of Formula I in combination with a pharmaceutical adjuvant, carrier or diluent.

A further aspect of this invention relates to a method of treatment or prevention of disorders responsive to opening of KCNQ potassium channels in a mammal in need thereof, which comprises administering to said mammal a therapeutically effective amount of a compound of Formula I. The compounds of Formula I should be useful in the treatment of treatment of migraine or a migraine attack, cluster headaches, bipolar disorder, convulsions, mania, acute mania, epilepsy, anxiety, depression, schizophrenia, functional bowel disorders, stroke, traumatic brain injury, multiple sclerosis, neurodegenerative disorders or alleviating pain such as musculoskeletal pain, post operative pain, surgical pain, inflammatory pain, neuropathic pain such as diabetic neuropathy and pain associated with cancer and fibromyalgia.

For therapeutic use, the compounds of Formula I will normally be administered as pharmaceutical compositions comprising as an active ingredient at least one compound in association with a pharmaceutically acceptable solid or liquid carrier and, optionally, with pharmaceutically acceptable adjutants and excipients employing standard and conventional techniques.

The pharmaceutical compositions include suitable dosage forms for oral, parenteral (including subcutaneous, intramuscular, intradermal and intravenous) bronchial or nasal administration. If a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in which case conventional suspending agents may be employed. Conventional preservatives, buffering agents and the like also may be added to the parenteral dosage forms. Aerosol compositions can be formed with pharmaceutically accepted propellants. The pharmaceutical compositions are prepared by conventional techniques and are normally formulated in unit doses. The unit dose depends on the composition and can range from about 0.01 mg to about 1000 mg. Some unit doses for solid compositions are 1 mg, 10, mg, 100 mg, and 1000 mg. Some unit doses for liquid compositions are 0.01 mg/mL, 0.1 mg/mL, 1 mg/mL, 10 mg/mL, and 100 mg/mL.

A suitable dose of a compound of Formula I or a related pharmaceutical composition for a mammal, including man, is about 0.01 mg/kg to about 100 mg/kg body weight daily of active ingredient. For parenteral administration, the dose may be in the range of about 0.1 mg/kg to about 10 mg/kg body weight for intravenous administration. For oral administration, the dose may be in the range about 0.1 mg/kg to about 100 mg/kg body weight. The active ingredient can be administered continuously or in equal doses from one to four times a day. Usually a small dose is administered, and the dosage is gradually increased until the optimal dosage for the patient is determined. The specific dosing regimen, however, must be carefully monitered and adjusted using sound medical judgement.

DESCRIPTION OF SPECIFIC EMBODIMENTS

Unless otherwise stated, solvents and reagents were used directly as obtained from commercial sources, and reactions were performed under a nitrogen atmosphere. Flash chromatography was conducted on Silica gel 60 (0.040-0.063 particle size; EM Science supply). $^1$H NMR spectra were recorded on a Bruker DRX-500f at 500 MHz; a Bruker DPX-300B at 300 MHz; or a Varian Gemini 300 at 300 MHz. The chemical shifts were reported in ppm on the δ scale relative to δ TMS=0. The following internal references were used for the residual protons in the following solvents: CDCl$_3$ ($\delta_H$ 7.26), CD$_3$OD ($\delta_H$ 3.30) and DMSO-d$_6$ ($\delta_H$ 2.50). Standard acronyms were employed to describe the multiplicity patterns: s (singlet), d (doublet), t (triplet), q (quartet), quint (quintet), m (multiplet), br (broad), app (apparent). The coupling constant (J) is in hertz. LC/MS was performed on a Shimadzu LC-10AS liquid chromatograph using a SPD-10AV UV-VIS detector with Mass Spectrometry data determined using a Micromass LC Platform in positive electrospray ionization mode (ESI+). Mass Spectrometry (MS) data was obtained using a standard flow injection technique on a Micromass LC Platform in positive electrospray ionization mode (ESI+) unless otherwise noted. High resolution mass spectrometry (HRMS) data was obtained using a standard flow injection technique on a Finnigan MAT 900 mass spectrometer in electrospray ionization (ESI) mode. The analytical reverse phase HPLC methods are as follows unless otherwise noted. A run of x minutes is a gradient of x−1 minutes from 100% A to 100% B followed by a 1 min at 100% B. For example, a 3 min run is 2 min gradient from 100% A to 100% B followed by 1 min at 100% B. Solvent A: 10% MeOH/90% H$_2$O/0.1% TFA; solvent B: 90% MeOH/10% H$_2$O/0.1% TFA; Column 1: YMC ODS-A 3.0×50 mm S7 C18; column 2: XTERRA 3.0×50 mm S7; column 3: YMC ODS-A C18 S5 4.6×33 mm; column 4: XTERRA C18 S5 4.6×50 mm; column 5 YMC C18 S5 4.6×50 mm. Preparative reverse phase HPLC was performed on a Shimadzu LC-8A automated preparative HPLC system with detector (SPD-10AV UV-VIS) wavelength and solvent systems (A and B) the same as above except where otherwise noted.

EXAMPLE 1

2-Amino-4-Trifluoromethyl-thiazole-5-carboxylic acid ethyl ester. To a solution of ethyl 2-chloro-4,4,4-trifluoroacetoacetate (50.0 g, 230 mmol) in ethanol (250 mL) was added thiourea (17.5 g, 230 mmol). The resulting mixture was heated at reflux for 3 h, at which time TLC indicated a complete reaction. The mixture was concentrated in vacuo, and the residue dissolved in ether. The organic layer was successively washed with aqueous sodium bicarbonate, and brine, then dried over magnesium sulfate and concentrated in vacuo. The resulting solid was recrystalized with ethyl acetate and hexanes to give white crystals (41.64 g, 75% yield). $^1$H NMR (MeOD-d4, 300 MHz): δ 4.26 (q, J=7.1 Hz, 2H), 1.31 (t, J=7.1 Hz, 3H).

EXAMPLE 2

2-Bromo-4-Trifluoromethyl-thiazole-5-carboxylic acid ethyl ester (III). To a solution of the aminothiazole (40.0 g, 167 mmol) in 48% HBr (300 mL) at 0° C. was added a 0° C. solution of sodium nitrite (17.0 g, 250 mmol) in water (200 mL) dropwise over 1 h. The mixture was stirred at 0° C. for an additional 0.5 h, at which time a 0° C. solution of CuBr (23.9 g, 167 mmol) in 48% HBr (200 mL) over 0.5 h. The mixture was stirred for an additional 0.5 h at 0° C., then for 2 h at room temperature. The mixture was then extracted three times with methylene chloride. The combined organic extracts were then dried over magnesium sulfate, filtered, and concentrated in vacuo. The product was purified by chromatography (SiO2, Hexane to 2.5% EtOAc/Hexane) to yield pure IV (47.0 g, 93% yield). $^1$H NMR (CDCl$_3$, 300 MHz): δ 4.40 (q, J=7.1 Hz, 2H), 1.38 (t, J=7.1 Hz, 3H).

EXAMPLE 3

Preparation of Formula II Compounds

2-Phenyl-4-trifluoromethyl-thiazole-5-carboxylic acid ethyl ester. To a solution of thiazole III (2.0 g, 6.6 mmol) and the phenyl boronic acid (9.9 mmol) in THF (10 mL) was added potassium fluoride (1.15 g, 19.8 mmol), palladium (II) acetate (74 mg, 0.33 mmol), and 2-(di-t-butylphosphino) biphenyl (197 mg, 0.66 mmol). This mixture was stirred at 25° C. for 24 h. Diethyl ether (100 mL) was then added and the mixture was washed with 1 N aqueous NaOH (2×50 mL), saturated aqueous NaCl (1×50 mL), dried over MgSO$_4$ and concentrated in vacuo to give an off-white solid. Purification by flash chromatography (silica, 0-2.5% ethyl acetate/hexane) gave the product, generally in 60-90% yield.

EXAMPLE 4

Preparation of IIb

To a solution of 2-(2-methoxy)phenyl-4-trifluoromethyl-thiazole-5-carboxylic acid ethyl ester (3.78 mmol) in CH$_2$Cl$_2$ (17.7 mL) at −78° C. under a Nitrogen atmosphere was added 1M BBr$_3$ in CH$_2$Cl$_2$ (4.75 mL, 4.75 mmol, 1.25 eq). The resulting mixture was stirred for 2 h at 0° C., at which time TLC indicated the consumption of starting material. The solution was cooled to −78° C. and quenched with saturated NaHCO$_3$ solution. The mixture was brought to room temperature, and extracted three times with CH$_2$Cl$_2$. The combined organic phases were dried over MgSO$_4$ and concentrated in vacuo. Purification was accomplished with chromatography on silica gel (10% EtOAc/Hexane). Yield: 900 mg (75%).

EXAMPLE 5

Preparation of IIc

To a solution of 2-(2-hydroxy)phenyl-4-trifluoromethyl-thiazole-5-carboxylic acid ethyl ester (3.15 mmol) in DMF (30.0 mL) at ambient temperature under a Nitrogen atmosphere was added 1,2-dibromoethane (5.43 mL, 63 mmol, 20 eq), then excess NaH. The resulting mixture was stirred for 18 h, at which time HPLC indicated the consumption of starting material. The solution was carefully quenched with ethanol, followed by saturated NH$_4$Cl solution. The solution was extracted three times with EtOAc, the combined organic phases were dried over MgSO$_4$ and concentrated in vacuo. Purification was accomplished with chromatography on silica gel. Yield: 950 mg (71%).

EXAMPLE 6

Preparation of IId

To a solution of 2-[2-(2-bromoethoxy)]phenyl-4-trifluoromethyl-thiazole-5-carboxylic acid ethyl ester (826 μmol) in acetone (3.5 mL) at ambient temperature under a Nitrogen atmosphere was added the appropriate secondary amine (4.13 mmol, 5 eq), then catalytic NaI (31 mg, 207 μmol, 0.2 eq). The resulting mixture was heated to 80° C. and stirred for 18 h, at which time HPLC indicated the consumption of starting material. The solution was concentrated in vacuo. Purification was accomplished with chromatography on silica gel (CH$_2$Cl$_2$, followed by 5% MeOH/CH$_2$Cl$_2$). Yield: 320 mg (93%).

EXAMPLE 7

Preparation of IIe

To a suspension of 2-(2-hydroxy)phenyl-4-trifluoromethyl-thiazole-5-carboxylic acid ethyl ester (3.15 mmol) in CH$_2$Cl$_2$ (10.0 mL) at 0° C. under a Nitrogen atmosphere was added pyridine (1.28 mL, 15.8 mmol, 5 eq), at which time the mixture was a homogeneous solution. Triflic anhydride (610 μL, 3.63 mmol, 1.15 eq) was added dropwise, and the reaction was stirred for 0.5 h, at which time TLC indicated the consumption of starting material. The solution was quenched with saturated NH$_4$Cl solution. The solution was extracted three times with CH$_2$Cl$_2$, the combined organic phases were dried over MgSO$_4$ and concentrated in vacuo. Purification was accomplished with chromatography on silica gel (10% EtOAc/Hexane). Yield: 601.9 mg (42%).

EXAMPLE 8

Preparation of IIf

To mixture of 2-(2-trifluoromethylsulfonyl)phenyl-4-trifluoromethyl-thiazole-5-carboxylic acid ethyl ester (557 μmol), Cs$_2$CO$_3$ (510 mg, 1.56 mmol, 2.8 eq), Pd(OAc)$_2$ (7.5 mg, 33 μmol, 0.06 eq), and BINAP (31.3 mg, 50 μmol, 0.09 eq) in a sealed tube was added toluene (10.0 mL), followed by morpholine (117 μL, 1.34 mmol, 2.4 eq). The mixture was flushed with Nitrogen, and heated at 90° C. for 24 h. The solvent was removed in vacuo and the crude product was used directly for subsequent chemistry.

EXAMPLE 9

Preparation of IIg

A solution of stannane VI (3.8 g, 12.1 mmol, 2 eq) and bromide III (1.83 g, 6.0 mmol, 1 eq) in DMF (17.2 mL) was sparged with Nitrogen. Solid Pd(PPh$_3$)$_2$Cl$_2$ (217 mg, 309 μmol, 0.052 eq) and CuI (92 mg, 483 μmol, 0.081 eq) were added, and the reaction was heated at 60° C. in a sealed tube for 18 h. The reaction was cooled to ambient temperature, and was diluted with water. The mixture was extracted two times into EtOAc, and the combined organic layers were washed with saturated NaCl solution. The EtOAc solution was further dried over MgSO$_4$, and concentrated in vacuo. Purification by silica gel chromatography (25% EtOAc/Hexane) provided the pure product. Yield: 1.97 g, (88%).

EXAMPLE 10

Preparation of IIi

To a solution of cinnamate ester IIh (3.18 g, 8.26 mmol, 1 eq) in ether (26 mL) was added a solution of sodium periodate (3.83 g, 17.9 mmol, 2.17 eq) in water (26 mL). A 2.5 wt % solution of OsO$_4$ in t-BuOH (5.6 mL, 427 μmol, 0.052 eq) was then added. The resulting mixture was vigorously stirred at ambient temperature for 24 h. The reaction was filtered through a pad of silica gel and then was concentrated in vacuo to afford the brown aldehyde IIi. Quantitative yield.

EXAMPLE 11

Preparation of V

To a solution of 2-bromobenzaldehyde (5.30 mmol) in benzene (40 mL) was added ethylene glycol (1.26 mL, 22.6 mmol, 4.3 eq) and p-toluenesulfonic acid (70 mg, 0.37 mmol, 0.07 eq). The resulting mixture was heated at reflux in a Dean-Stark apparatus. After 4 h, the reaction was cooled to ambient temperature, quenched with triethylamine, and concentrated in vacuo. Purification was accomplished with chromatography on silica gel. Quantitative yield.

EXAMPLE 12

Preparation of VI

To a solution of 2-dioxolanyl bromobenzene (13.0 mmol) in THF (22.5 mL) at −78° C. under Nitrogen was added 2.5 M n-BuLi in hexane (5.73 mL, 14.3 mmol, 1.1 eq) dropwise. After 1 h, a 1 M solution of Me$_3$SnCl in THF (14.4 mL, 14.4 mmol, 1.1 eq) was added. After 15 minutes, the temperature bath was removed, and the reaction was allowed to reach ambient temperature. Ether was added, followed by water. The mixture was extracted two times into ether, and the combined organic layers were washed with saturated NaCl solution. The ether solution was further dried over $MgSO_4$, and concentrated in vacuo. $^1$H NMR revealed ~90% conversion to the desired stannane, which was used as-is in subsequent chemistry. Mass yield: 3.8 g, (92%).

Preparation of Formula I Compounds

Examples of Ester Hydrolysis Procedure

EXAMPLE 13

2-Phenyl-4-trifluoromethyl-thiazole-5-carboxylic acid. To a solution of 2-phenyl-4-trifluoromethyl-thiazole-5-carboxylic acid ethyl ester (1.6 g, 5.3 mmol) in THF (16 mL) was added 1 N aqueous LiOH (16 mL, 16 mmol). This mixture was brought to reflux and stirred vigorously for 1 h. The mixture was allowed to cool to 25° C. and 1 N aqueous HCl (35 mL, 35 mmol) was added. The mixture was extracted with ethyl acetate (2×50 mL) and the combined organic extracts were washed with saturated aqueous NaCl (1×50 mL), dried over $MgSO_4$ and concentrated in vacuo to give the carboxylic acid as a white solid (1.32 g, 91%).

Examples of Carboxylic Acid Amimation Procedures

EXAMPLE 14

2-Phenyl-4-trifluoromethyl-thiazole-5-carboxylic acid [1-(3-trifluoromethoxyphenyl)-ethyl]-amide. To a solution of 2-phenyl-4-trifluoromethyl-thiazole-5-carboxylic acid (35 mg, 0.128 mmol) in DMF (1 mL) was added PyBOP (73 mg, 0.141 mmol) and DMAP (16 mg, 0.128 mmol). A solution of 1-(3-trifluoromethoxyphenyl)-ethylamine (27 mg, 0.128 mmol) in DMF (0.5 mL) was then added, followed by $Et_3N$ (36 µL, 0.256 mmol). This mixture was stirred at 25° C. for 18 h. The reaction mixture was applied directly to a preparatory HPLC column for purification (C18, 10-100% methanol/water/0.1% trifluoroacetic acid) which gave the amide as a white solid (24.9 mg, 42%).

EXAMPLE 15

Preparation of Id

To a solution of acetal Ic (224 µmol) in 9:1 acetone:water (6 mL) was added p-toluenesulfonic acid (20 mg, 105 µmol, 0.47 eq). The resulting mixture was heated to 60° C. After 16 h, the reaction was cooled to ambient temperature, quenched with saturated $NaHCO_3$ solution, and extracted three times into EtOAc. The combined organic phases were dried over $MgSO_4$ and concentrated in vacuo. Purification was accomplished with chromatography on silica gel. Quantitative yield.

EXAMPLE 16

Preparation of Ie

To a suspension of aldehyde Id (91.1 µmol) in ethylene glycol dimethyl ether (400 µL) was added the appropriate amine (230 µmol, 2.5 eq), trimethyl orthoformate (33 µL, 300 µmol, 3.3 eq), and acetic acid (2 µL, 35 µmol, 0.38 eq). The resulting mixture was stirred at ambient temperature for 24 h. Solid $NaBH(OAc)_3$ was then added, and stirring was continued for another 16 h. The reaction was diluted with methanol and loaded onto a strong-cation ion exchange column (SCX). The column was washed with methanol (20 mL), then the desired product was eluted with 2 M $NH_3$/MeOH (15 mL). The ammonia solution was concentrated in vacuo to afford the pure products.

All examples were made using these methods. Compounds which needed further purification were purified by flash chromatography (silica, 0-10% methanol/chloroform).

EXAMPLE 17

2-(4-fluorophenyl)-4-(trifluoromethyl)-N-[1-[3-(trifluoromethoxy)phenyl]ethyl]-5-thiazolecarboxamide. $^1$H NMR ($CDCl_3$, 300 MHz): δ 7.96-7.92 (m, 2H), 7.41-7.32 (m, 2H), 7.21-7.13 (m, 4H), 6.45 (br d, J=6.6 Hz, 1H), 5.27 (app quint, J=7.0 Hz, 1H), 1.61 (d, J=7.0 Hz, 3H); LCMS (M+) 478, RT=1.833 (column 1; run time: 3 min).

EXAMPLE 18

2-(2-methoxyphenyl)-4-(trifluoromethyl)-N-[1-[3-(trifluoromethoxy)phenyl]ethyl]-5-thiazolecarboxamide. $^1$H NMR ($CDCl_3$, 300 MHz): δ 8.43-8.40 (m, 1H), 7.47-7.03 (m, 7H), 6.43 (app br d, 1H), 5.30 (app quint, J=7.0 Hz, 1H), 4.05 (s, 3H), 1.61 (d, J=7.0 Hz, 3H); LCMS (M+) 490, RT=1.850 (column 5; run time: 3 min).

EXAMPLE 19

2-(2-methoxyphenyl)-4-(trifluoromethyl)-N-[1-[3-(trifluoromethyl)phenyl]ethyl]-5-thiazolecarboxamide. $^1$H NMR ($CDCl_3$, 300 MHz): δ 8.43-8.40 (m, 1H), 7.63-7.44 (m, 5H), 7.13-7.03 (m, 2H), 6.45 (br d, 1H), 5.33 (app quint, J=7.0 Hz, 1H), 4.05 (s, 3H), 1.63 (d, J=7.0 Hz, 3H); LCMS (M+) 474, RT=1.800 (column 5; run time: 3 min).

EXAMPLE 20

2-(3,4-dioxolanylphenyl)-4-(trifluoromethyl)-N-[1-[3-(trifluoromethoxy)phenyl]ethyl]-5-thiazolecarboxamide. $^1$H NMR ($CDCl_3$, 300 MHz): δ 7.47-7.38 (m, 3H), 7.30 (d, J=7.7 Hz, 1H), 7.17 (m, 2H), 6.87 (d, J=7.7 Hz, 1H), 6.43 (br d, J=5.9 Hz, 1H), 6.05 (s, 2H), 5.27 (app quint, J=7.0 Hz, 1H), 1.60 (d, J=7.0 Hz, 3H); LCMS (M+) 504, RT=1.817 (column 1; run time: 3 min).

EXAMPLE 21

2-(2-fluorophenyl)-4-(trifluoromethyl)-N-[1-[3-(trifluoromethoxy)phenyl]ethyl]-5-thiazolecarboxamide. $^1$H NMR ($CDCl_3$, 300 MHz): δ 8.35-8.30 (m, 1H), 7.48-7.27 (m, 4H), 7.24-7.18 (m, 3H), 6.43 (br d, J=5.9 Hz, 1H), 5.30 (app quint, J=7.0 Hz, 1H), 1.62 (d, J=7.0 Hz, 3H); LCMS (M+) 478, RT=1.833 (column 5; run time: 3 min).

EXAMPLE 22

2-(2-fluorophenyl)-4-(trifluoromethyl)-N-[1-[3-(trifluoromethyl)phenyl]ethyl]-5-thiazolecarboxamide. $^1$H NMR ($CDCl_3$, 300 MHz): δ 8.33 (dd, J=1.8, 7.7 Hz, 1H), 7.62-7.45 (m, 5H), 7.33-7.28 (m, 1H), 7.25-7.18 (m, 1H), 6.45 (app br d, 1H), 5.33 (app quint, J=7.0 Hz, 1H), 1.64 (d, J=7.0 Hz, 3H); LCMS (M+) 462, RT=1.797 (column 5; run time: 3 min).

EXAMPLE 23

2-(2-methoxyphenyl)-4-(trifluoromethyl)-N-[1-[3-(1-morpholinyl)phenyl]ethyl]-5-thiazolecarboxamide. $^1$H NMR (CDCl$_3$, 300 MHz): δ 8.42-8.39 (m, 1H), 7.49-7.44 (m, 1H), 7.29 (m, 1H), 7.12-7.03 (m, 2H), 6.93-6.83 (m, 3H), 6.42 (br d, J=6.2 Hz, 1H), 5.24 (app quint, J=7.0 Hz, 1H), 4.04 (s, 3H), 3.86 (t, J=4.7 Hz, 4H), 3.18 (t, J=4.7 Hz, 4H), 1.60 (d, J=7.0 Hz, 3H); LCMS (M+) 491, RT=1.537 (column 1; run time: 3 min).

EXAMPLE 24

2-(3-methoxyphenyl)-4-(trifluoromethyl)-N-[1-[3-(trifluoromethoxy)phenyl]ethyl]-5-thiazolecarboxamide. $^1$H NMR (CDCl$_3$, 300 MHz): δ 7.49-7.32 (m, 5H), 7.21-7.05 (m, 3H), 6.46 (br d, J=6.2 Hz, 1H), 5.28 (app quint, J=7.0 Hz, 1H), 3.88 (s, 3H), 1.61 (d, J=7.0 Hz, 3H); LCMS (M+) 490, RT=1.867 (column 1; run time: 3 min).

EXAMPLE 25

2-(2-methoxyphenyl)-4-(trifluoromethyl)-N-[1-[3-(dimethylamino)phenyl]ethyl]-5-thiazolecarboxamide. $^1$H NMR (CDCl$_3$, 300 MHz): δ 8.42 (dd, J=1.5, 7.7 Hz, 1H), 7.47-7.44 (m, 1H), 7.27-7.22 (m, 1H), 7.13-7.03 (m, 2H), 6.74 (m, 3H), 6.41 (app br d, 1H), 5.23 (app quint, J=7.0 Hz, 1H), 4.05 (s, 3H), 2.97 (s, 6H), 1.62 (d, J=7.0 Hz, 3H); LCMS (M+) 449, RT=1.360 (column 5; run time: 3 min).

EXAMPLE 26

2-(2-fluorophenyl)-4-(trifluoromethyl)-N-[1-[3-(dimethylamino)phenyl]ethyl]-5-thiazolecarboxamide. $^1$H NMR (CDCl$_3$, 300 MHz): δ 8.31 (td, J=1.8, 7.7 Hz, 1H), 7.55-7.45 (m, 1H), 7.31-7.21 (m, 3H), 6.73 (m, 3H), 6.45 (brd, J=6.2 Hz, 1H), 5.25 (app quint, J=7.0 Hz, 1H), 2.97 (s, 6H), 1.61 (d, J=7.0 Hz, 3H); LCMS (M+) 437, RT=1.287 (column 5; run time: 3 min).

EXAMPLE 27

2-(2-methoxyphenyl)-4-(trifluoromethyl)-N-(3-fluorophenyl)methyl-5-thiazolecarboxamide. $^1$H NMR (CDCl$_3$, 300 MHz): δ 8.42 (dd, J=1.8, 8.1 Hz, 1H), 7.47-7.44 (m, 1H), 7.34 (m, 1H), 7.14-6.97 (m, 5H), 6.73 (m, 3H), 6.53 (br s, 1H), 4.64 (d, J=5.9 Hz, 2H), 4.06 (s, 3H); LCMS (M+) 410, RT=1.697 (column 5; run time: 3 min).

EXAMPLE 28

2-(4-methoxyphenyl)-4-(trifluoromethyl)-N-[1-[3-(trifluoromethoxy)phenyl]ethyl]-5-thiazolecarboxamide. $^1$H NMR (CDCl$_3$, 300 MHz): δ 7.88 (dt, J=2.4, 9.5 Hz, 2H), 7.44-7.37 (m, 1H), 7.34-7.27 (m, 1H), 7.23-7.12 (m, 2H), 6.97 (dt, J=2.3, 9.4 Hz, 2H), 6.42 (br d, J=6.6 Hz, 1H), 5.27 (app quint, J=7.0 Hz, 1H), 3.87 (s, 3H), 1.60 (d, J=7.0 Hz, 3H); LCMS (M+) 490, RT=1.863 (column 5; run time: 3 min).

EXAMPLE 29

2-(3,4-dimethoxyphenyl)-4-(trifluoromethyl)-N-[1-[3-(trifluoromethoxy)phenyl]ethyl]-5-thiazolecarboxamide. $^1$H NMR (CDCl$_3$, 300 MHz): δ 7.49-7.26 (m, 4H), 7.17 (m, 2H), 6.90 (d, J=8.1 Hz, 1H), 6.43 (br d, J=7.0 Hz, 1H), 5.28 (app quint, J=7.0 Hz, 1H), 3.97 (s, 3H), 3.94 (s, 3H), 1.61 (d, J=7.0 Hz, 3H); LCMS (M+) 520, RT=1.813 (column 1; run time: 3 min).

EXAMPLE 30

2-(2,4-dimethoxyphenyl)-4-(trifluoromethyl)-N-[1-[3-(trifluoromethoxy)phenyl]ethyl]-5-thiazolecarboxamide. $^1$H NMR (CDCl$_3$, 300 MHz): δ 8.31 (d, J=8.8 Hz, 1H), 7.42-7.13 (m, 4H), 6.62 (dd, J=2.3, 8.8 Hz, 1H), 6.52 (d, J=2.3 Hz, 1H), 6.45 (br d, J=6.6 Hz, 1H), 5.28 (app quint, J=7.0 Hz, 1H), 4.00 (s, 3H), 3.87 (s, 3H), 1.60 (d, J=7.0 Hz, 3H); LCMS (M+) 520, RT=1.873 (column 1; run time: 3 min).

EXAMPLE 31

2-(2,4-dimethoxyphenyl)-4-(trifluoromethyl)-N-[1-[3-(4-morpholinyl)phenyl]ethyl]-5-thiazolecarboxamide. $^1$H NMR (CDCl$_3$, 500 MHz): δ 8.32 (d, J=8.8 Hz, 1H), 7.30-7.24 (m, 1H), 6.93-6.83 (m, 3H), 6.62 (dd, J=2.4, 8.8 Hz, 1H), 6.53 (d, J=2.4 Hz, 1H), 6.42 (br d, J=7.0 Hz, 1H), 5.24 (app quint, J=7.0 Hz, 1H), 4.01 (s, 3H), 3.87 (s, 3H), 3.86 (t, J=4.9 Hz, 4H), 3.18 (t, J=4.9 Hz, 4H), 1.60 (d, J=7.0 Hz, 3H); LCMS (M+) 521, RT=1.607 (column 1; run time: 3 min).

EXAMPLE 32

2-(2-methoxyphenyl)-4-(trifluoromethyl)-N-[1-[3-(1-piperidinyl)phenyl]ethyl]-5-thiazolecarboxamide. $^1$H NMR (CDCl$_3$, 300 MHz): δ 8.42 (dd, J=1.5, 7.7 Hz, 1H), 7.49-7.44 (m, 1H), 7.28-7.23 (m, 1H), 7.13-7.03 (m, 2H), 6.95-6.80 (m, 3H), 6.40 (app br d, 1H), 5.24 (app quint, J=7.0 Hz, 1H), 4.05 (s, 3H), 3.18 (t, J=5.1 Hz, 4H), 1.72 (t, J=5.1 Hz, 4H), 1.60 (d, J=7.0 Hz, 3H), 1.56 (s, 2H); LCMS (M+) 489, RT=1.427 (column 1; run time: 3 min).

EXAMPLE 33

2-(2-methoxyphenyl)-4-(trifluoromethyl)-N-[1-[3-(1-pyrrolidinyl)phenyl]ethyl]-5-thiazolecarboxamide. $^1$H NMR (CDCl$_3$, 300 MHz): δ 8.41 (dd, J=1.2, 7.8 Hz, 1H), 7.48-7.02 (m, 4H), 6.66 (d, J=7.4 Hz, 1H), 6.52 (m, 3H), 5.25 (app quint, J=6.8 Hz, 1H), 4.03 (s, 3H), 3.29 (t, J=6.2 Hz, 4H), 2.01 (t, J=6.2 Hz, 4H), 1.60 (d, J=6.8 Hz, 3H); LCMS (M+) 475, RT=1.593 (column 1; run time: 3 min).

EXAMPLE 34

2-(2-methoxyphenyl)-4-(trifluoromethyl)-N-[1-[3-[(2-furanylmethyl)methylamino]phenyl]ethyl]-5-thiazolecarboxamide. $^1$H NMR (CDCl$_3$, 300 MHz): δ 8.41 (dd, J=1.8, 8.1 Hz, 1H), 7.45-7.02 (m, 5H), 6.82-6.74 (m, 3H), 6.45 (brd, J=7.1 Hz, 1H), 6.28 (m, 1H), 6.16 (brd, J=3.1 Hz, 1H), 5.23 (app quint, J=7.0 Hz, 1H), 4.46 (s, 2H), 4.03 (s, 3H), 3.01 (s, 3H), 1.61 (d, J=7.0 Hz, 3H); LCMS (M+) 515, RT=1.570 (column 1; run time: 3 min).

EXAMPLE 35

2-(2-fluorophenyl)-4-(trifluoromethyl)-N-[1-[3-[(2-furanylmethyl)methylamino]phenyl]ethyl]-5-thiazolecarboxamide. $^1$H NMR (CDCl$_3$, 300 MHz): δ 8.31 (td, J=1.8, 7.7 Hz, 1H), 7.46-7.21 (m, 5H), 6.80-6.72 (m, 3H, 6.46 (br d, J=7.0 Hz, 1H), 6.28 (dd, J=2.0, 3.1 Hz, 1H), 6.14 (br d, J=2.6 Hz, 1H), 5.22 (app quint, J=7.0 Hz, 1H), 4.46 (s, 2H), 3.01 (s, 3H), 1.61 (d, J=7.0 Hz, 3H); LCMS (M+) 503, RT=1.560 (column 1; run time: 3 min).

EXAMPLE 36

2-(3,4-dimethoxyphenyl)-4-(trifluoromethyl)-N-[1-[3-[(1-pyrrolidinyl)methyl]phenyl]ethyl]-5-thiazolecarboxamide. $^1$H NMR (CDCl$_3$, 500 MHz): δ 7.47-7.23 (m, 5H), 6.88 (d, J=8.4 Hz, 1H), 6.52 (br d, J=7.3 Hz, 1H), 5.25 (app quint, J=7.1 Hz, 1H), 3.95 (s, 3H), 3.92 (s, 3H), 3.63 (m, 2H), 2.52 (br s, 4H), 1.79 (t, J=6.6 Hz, 4H), 1.60 (d, J=6.9 Hz, 3H); LCMS (M+) 519, RT=(column 1; run time: 3 min).

EXAMPLE 37

2-(2-fluorophenyl)-4-(trifluoromethyl)-N-[1-[3-[(4-morpholinyl)methyl]phenyl]ethyl]-5-thiazolecarboxamide. $^1$H NMR (CDCl$_3$, 400 MHz): δ 8.31 (m, 1H), 7.47 (m, 1H), 7.34-7.21 (m, 5H), 6.51 (br d, J=7.0, 1H), 5.27 (app quint, J=7.1 Hz, 1H), 3.71 (t, J=4.6 Hz, 4H), 3.50 (s, 2H), 2.44 (t, J=4.3 Hz, 4H), 1.61 (d, J=6.9 Hz, 3H); LCMS (M+) 493, RT=1.407 (column 1; run time: 3 min).

EXAMPLE 38

2-(1-naphthyl)-4-(trifluoromethyl)-N-[1-[3-[(diethylamino)methyl]phenyl]ethyl]-5-thiazolecarboxamide. $^1$H NMR (CDCl$_3$, 300 MHz): δ 8.72 (d, J=8.4 Hz, 1H), 8.00-7.24 (m, 9H), 6.61 (br d, J=7.1, 1H), 5.30 (app quint, J=7.1 Hz, 1H), 3.59 (s, 2H), 2.54 (q, J=7.1 Hz, 1H), 1.64 (d, J=6.9 Hz, 3H), 1.06 (t, J=7.1 Hz, 6H); LCMS (M+) 511, RT=1.557 (column 1; run time: 3 min).

EXAMPLE 39

2-(2-methoxyphenyl)-4-(trifluoromethyl)-N-[1-(3-aminophenyl)ethyl]-5-thiazolecarboxamide. $^1$H NMR (CDCl$_3$, 300 MHz): δ 8.40 (dd, J=1.8, 8.1 Hz, 1H), 7.45 (ddd, J=1.8,7.2,8.5 Hz, 1H), 7.16-7.02 (m, 3H), 6.80-6.67 (m, 3H), 6.38 (br d, J=7.3 Hz, 1H), 5.18 (app quint, J=7.1 Hz, 1H), 4.03 (s, 3H), 1.57 (d, J=6.9 Hz, 3H); LCMS (M+) 421, RT=1.230 (column 1; run time: 3 min).

EXAMPLE 40

2-(2-methoxyphenyl)-4-(trifluoromethyl)-N-[1-[3-(guanidinyl)phenyl]ethyl]-5-thiazolecarboxamide. $^1$H NMR (MeOD, 300 MHz): δ 8.36 (dd, J=1.5, 8.1 Hz, 1H), 7.54-7.13 (m, 7H), 5.16 (app quint, J=7.1 Hz, 1H), 4.10 (s, 3H), 1.56 (d, J=6.9 Hz, 3H); LCMS (M+) 463, RT=1.263 (column 1; run time: 3 min).

EXAMPLE 41

2-(5-fluoro-2-methoxyphenyl)-4-(trifluoromethyl)-N-[1-[3-(trifluoromethoxy)phenyl]ethyl]-5-thiazolecarboxamide. $^1$H NMR (CDCl$_3$, 300 MHz): δ 8.12 (dd, J=3.1, 9.2 Hz, 1H), 7.43-7.13 (m, 5H), 6.99 (dd, J=4.2, 9.1 Hz, 1H), 6.44 (br d, J=6.9 Hz, 1H), 5.29 (app quint, J=7.1 Hz, 1H), 4.03 (s, 3H), 1.61 (d, J=6.9 Hz, 3H); LCMS (M+) 508, RT=2.723 (column 3; run time: 4 min).

EXAMPLE 42

2-(5-fluoro-2-methoxyphenyl)-4-(trifluoromethyl)-N-[1-[3-(dimethylamino)phenyl]ethyl]-5-thiazolecarboxamide. $^1$H NMR (CDCl$_3$, 300 MHz): δ 8.12 (dd, J=3.2, 9.2 Hz, 1H), 7.27-6.69 (m, 6H), 6.45 (br d, J=6.7 Hz, 1H), 5.25 (app quint, J=7.1 Hz, 1H), 4.03 (s, 3H), 2.97 (s, 6H), 1.62 (d, J=6.9 Hz, 3H); LCMS (M+) 467, RT=2.103 (column 3; run time: 4 min).

EXAMPLE 43

2-(5-fluoro-2-methoxyphenyl)-4-(trifluoromethyl)-N-[1-[3-(trifluoromethyl)phenyl]ethyl]-5-thiazolecarboxamide. $^1$H NMR (CDCl$_3$, 300 MHz): δ 8.13 (dd, J=2.9, 9.2 Hz, 1H), 7.62-7.50 (m, 4H), 7.20-6.97 (m, 2H), 6.45 (br d, J=7.3 Hz, 1H), 5.33 (app quint, J=6.9 Hz, 1H), 4.04 (s, 3H), 1.63 (d, J=7.0 Hz, 3H); LCMS (M+) 492, RT=2.680 (column 3; run time: 4 min).

EXAMPLE 44

2-(5-fluoro-2-methoxyphenyl)-4-(trifluoromethyl)-N-[(3-fluorophenyl)methyl]-5-thiazolecarboxamide. $^1$H NMR (CDCl$_3$, 300 MHz): δ 8.14 (dd, J=3.2, 9.3 Hz, 1H), 7.36-6.98 (m, 6H), 6.45 (app br s, 1H), 4.65 (d, J=5.8 Hz, 2H), 4.05 (s, 3H); LCMS (M+) 428, RT=2.557 (column 3; run time: 4 min).

EXAMPLE 45

2-(5-fluoro-2-methoxyphenyl)-4-(trifluoromethyl)-N-[(3-methoxyphenyl)methyl]-5-thiazolecarboxamide. $^1$H NMR (CDCl$_3$, 300 MHz): δ 8.13 (dd, J=3.3, 9.2 Hz, 1H), 7.32-6.84 (m, 6H), 6.45 (app br s, 1H), 4.63 (d, J=5.6 Hz, 2H), 4.05 (s, 3H), 3.82 (s, 3H); LCMS (M+) 440, RT=20547 (column 3; run time: 4 min).

EXAMPLE 46

2-(5-fluoro-2-methoxyphenyl)-4-(trifluoromethyl)-N-[(3-trifluoromethoxyphenyl)methyl]-5-thiazolecarboxamide. $^1$H NMR (CDCl$_3$, 300 MHz): δ 8.13 (dd, J=3.3, 9.2 Hz, 1H), 7.44-6.98 (m, 6H), 6.52 (app br s, 1H), 4.68 (d, J=5.9 Hz, 2H), 4.05 (s, 3H); LCMS (M+) 494, RT=2.713 (column 3; run time: 4 min).

EXAMPLE 47

(S)-2-(5-fluoro-2-methoxyphenyl)-4-(trifluoromethyl)-N-[1-[3-(4-morpholinyl)phenyl]ethyl]-5-thiazolecarboxamide. $^1$H NMR (CDCl$_3$, 300 MHz): δ 8.10 (dd, J=2.9, 9.2 Hz, 1H), 7.46-6.96 (m, 6H), 6.67 (br d, J=6.9 Hz, 1H), 5.27 (app quint, J=7.0 Hz, 1H), 4.07-3.98 (m, 5H), 3.42 (t, J=4.8 Hz, 4H), 1.60 (d, J=7.0 Hz, 3H); LCMS (M+) 509, RT=2.383 (column 3; run time: 4 min).

EXAMPLE 48

(S)-2-(5-fluoro-2-methoxyphenyl)-4-(trifluoromethyl)-N-[1-[3-(methoxy)phenyl]ethyl]-5-thiazolecarboxamide. $^1$H NMR (CDCl$_3$, 300 MHz): δ 8.13 (dd, J=3.2, 9.3 Hz, 1H), 7.33-6.83 (m, 6H), 6.38 (br d, J=6.6 Hz, 1H), 5.32-5.20 (m, 1H), 4.04 (s, 3H), 3.82 (s, 3H), 1.61 (d, J=6.9 Hz, 3H); LCMS (M+) 454, RT=2.560 (column 3; run time: 4 min).

EXAMPLE 49

2-(2-chlorophenyl)-4-(trifluoromethyl)-N-[1-[3-(trifluoromethoxy)phenyl]ethyl]-5-thiazolecarboxamide. $^1$H NMR (CDCl$_3$, 300 MHz): δ 8.38-8.31 (m, 1H), 7.54-7.18 (m, 7H), 6.40 (app br s, 1H), 5.31 (app quint, J=7.1 Hz, 1H), 1.62 (d, J=7.0 Hz, 3H); LCMS (M+) 494, RT=2.733 (column 3; run time: 4 min).

EXAMPLE 50

2-(2-chlorophenyl)-4-(trifluoromethyl)-N-[1-[3-(dimethylamino)phenyl]ethyl]-5-thiazolecarboxamide. $^1$H NMR (CDCl$_3$, 500 MHz): δ 8.35-8.31 (m, 1H), 7.53-7.49 (m, 1H), 7.44-7.38 (m, 2H), 7.27-7.22 (m, 1H), 6.74-6.65 (m, 3H), 6.47 (br d, J=6.7 Hz, 1H), 5.23 (app quint, J=7.0 Hz, 1H), 2.97 (s, 6H), 1.62 (d, J=6.8 Hz, 3H); LCMS (M+) 453, RT=2.077 (column 3; run time: 4 min).

EXAMPLE 51

2-(2-chlorophenyl)-4-(trifluoromethyl)-N-[1-[3-(trifluoromethyl)phenyl]ethyl]-5-thiazolecarboxamide. $^1$H NMR (CDCl$_3$, 300 MHz): δ 8.38-8.31 (m, 1H), 7.62-7.39 (m, 7H), 6.44 (br d, J=6.0 Hz, 1H), 5.34 (app quint, J=6.9 Hz, 1H), 1.64 (d, J=7.0 Hz, 3H); LCMS (M+) 478, RT=2.687 (column 3; run time: 4 min).

EXAMPLE 52

2-(2-chlorophenyl)-4-(trifluoromethyl)-N-[1-[3-(4-morpholinyl)phenyl]ethyl]-5-thiazolecarboxamide. $^1$H NMR (CDCl$_3$, 500 MHz): δ 8.36-8.30 (m, 1H), 7.52-7.26 (m, 4H), 6.92-6.84 (m, 3H), 6.45 (br d, J=7.0 Hz, 1H), 5.24 (app quint, J=7.0 Hz, 1H), 3.86 (t, J=4.8 Hz, 4H), 3.18 (t, J=4.8 Hz, 4H), 1.61 (d, J=6.9 Hz, 3H); LCMS (M+) 495, RT=2.397 (column 3; run time: 4 min).

EXAMPLE 53

2-(2-chlorophenyl)-4-(trifluoromethyl)-N-[1-[3-(4-morpholinylmethyl)phenyl]ethyl]-5-thiazolecarboxamide. $^1$H NMR (CDCl$_3$, 400 MHz): δ 8.36-8.31 (m, 7H), 6.45 (br d, J=6.8 Hz, 1H), 5.28 (app quint, J=7.1 Hz, 1H), 3.71 (t, J=4.5 Hz, 4H), 3.51 (s, 2H), 2.44 (t, J=4.5 Hz, 4H), 1.62 (d, J=6.9 Hz, 3H); LCMS (M+) 509, RT=2.093 (column 3; run time: 4 min).

EXAMPLE 54

2-[2-(2-diethylaminoethyl)phenyl]-4-(trifluoromethyl)-N-(3-fluorobenzyl)-5-thiazolecarboxamide. $^1$H NMR (CDCl$_3$, 300 MHz): δ 8.42 (m, 1H), 7.46-7.30 (m, 2H), 7.15-7.01 (m, 5H), 6.48 (app br s, 1H), 4.65 (d, J=5.6 Hz, 2H), 4.30 (t, J=6.6 Hz, 2H), 3.05 (t, J=6.6 Hz, 2H), 2.65 (q, J=7.3 Hz, 4H), 1.07 (t, J=7.3 Hz, 6H); LCMS (M+) 495, RT=1.420 (column 3; run time: 3 min).

EXAMPLE 55

2-[2-(4-morpholinyl)phenyl]-4-(trifluoromethyl)-N-[1-[3-(methoxy)phenyl]ethyl]-5-thiazolecarboxamide. $^1$H NMR (CDCl$_3$, 300 MHz): δ 8.39 (m, 1H), 7.48-7.27 (m, 4H), 6.98-6.83 (m, 3H), 6.41 (br d, J=6.2 Hz, 1H), 5.25 (app quint, J=7.0 Hz, 1H), 3.97 (t, J=4.5 Hz, 4H), 3.82 (s, 3H), 2.97 (t, J=4.5 Hz, 4H), 1.60 (d, J=7.0 Hz, 3H); LCMS (M+) 491, RT=2.447 (column 3; run time: 4 min).

EXAMPLE 56

2-[2-(4-morpholinyl)phenyl]-4-(trifluoromethyl)-N-[1-[3-(trifluoromethyl)phenyl]ethyl]-5-thiazolecarboxamide. $^1$H NMR (CDCl$_3$, 300 MHz): δ 8.40 (m, 1H), 7.63-7.31 (m, 7H), 6.46 (br d, 1H), 5.33 (app quint, J=7.0 Hz, 1H), 3.98 (t, J=4.4 Hz, 4H), 2.97 (t, J=4.4 Hz, 4H), 1.63 (d, J=7.0 Hz, 3H); LCMS (M+) 529, RT=2.593 (column 3; run time: 4 min).

EXAMPLE 57

2-[2-(4-morpholinyl)phenyl]-4-(trifluoromethyl)-N-[1-[3-(trifluoromethoxy)phenyl]ethyl]-5-thiazolecarboxamide. $^1$H NMR (CDCl$_3$, 300 MHz): δ 8.40 (m, 1H), 7.49-7.18 (m, 7H), 6.44 (br s, 1H), 5.30 (app quint, J=7.0 Hz, 1H), 3.98 (t, J=4.4 Hz, 4H), 2.97 (t, J=4.4 Hz, 4H), 1.61 (d, J=7.0 Hz, 3H); LCMS (M+) 545, RT=2.667 (column 3; run time: 4 min).

EXAMPLE 58

2-[4-(4-morpholinyl)phenyl]-4-(trifluoromethyl)-N-[1-[3-(trifluoromethoxy)phenyl]ethyl]-5-thiazolecarboxamide. $^1$H NMR (CDCl$_3$, 300 MHz): δ 7.83 (m, 2H), 7.43-7.29 (m, 2H), 7.21-7.14 (m, 2H), 6.94-6.85 (m, 2H), 6.42 (br d, 1H), 5.27 (app quint, J=7.0 Hz, 1H), 3.87 (t, J=4.8 Hz, 4H), 3.28 (t, J=4.8 Hz, 4H), 1.60 (d, J=7.0 Hz, 3H); LCMS (M+) 545, RT=1.973 (column 3; run time: 3 min).

EXAMPLE 59

2-[3-[(4-pyridinyl)ethylaminomethyl]phenyl]-4-(trifluoromethyl)-N-(3-trifluoromethoxybenzyl)-5-thiazolecarboxamide. $^1$H NMR (CDCl$_3$, 500 MHz): δ 8.37 (s, 2H), 7.61-7.08 (m, 11H), 4.66 (d, J=5.5 Hz, 2H), 3.91 (s, 2H), 3.50 (s, 2H), 2.45 (q, J=7.0 Hz, 2H), 0.94 (t, J=7.0 Hz, 3H); LCMS (M+) 594, RT=1.937 (column 2; run time: 4 min).

EXAMPLE 60

(S)-2-[3-[(4-pyridinyl)ethylaminomethyl]phenyl]-4-(trifluoromethyl)-N-[1-(3-methoxyphenyl)ethyl]-5-thiazolecarboxamide. $^1$H NMR (CDCl$_3$, 500 MHz): δ 8.45-8.40 (m, 2H), 7.58-6.92 (m, 10H), 6.54 (br d, J=6.7 Hz, 1H), 5.25 (app quint, J=7.0 Hz, 1H), 3.82 (s, 3H), 3.52 (s, 2H), 3.48 (s, 2H), 2.46 (q, J=7.0 Hz, 2H), 1.61 (d, J=7.0 Hz, 3H), 0.96 (t, J=7.0 Hz, 3H); LCMS (M+) 554, RT=1.627 (column 2; run time: 4 min).

EXAMPLE 61

2-[3-(diethylaminomethyl)pyridin-2-yl]-4-(trifluoromethyl)-N-[1-[3-(trifluoromethoxy)phenyl]ethyl]-5-thiazolecarboxamide. $^1$H NMR (CDCl$_3$, 300 MHz): δ 8.46 (d, J=5.5 Hz, 1H), 8.20 (d, J=7.7 Hz, 1H), 7.44-7.10 (m, 5H), 6.32 (br d, J=5.9 Hz, 1H), 5.29 (app quint, J=7.2 Hz, 1H), 4.17 (s, 2H), 2.58 (q, J=7.2 Hz, 4H), 1.60 (d, J=7.0 Hz, 3H), 1.02 (t, J=7.2 Hz, 6H); LCMS (M+) 546, RT=1.670 (column 3; run time: 4 min).

EXAMPLE 62

(S)-2-[3-(pyridin-4-ylmethyl)ethylaminomethyl]pyridin-2-yl]-4-(trifluoromethyl)-N-[1-[3-(4-morpholinyl)phenyl]ethyl]-5-thiazolecarboxamide. $^1$H NMR (CDCl$_3$, 300 MHz): δ 8.56-8.41 (m, 3H), 8.19 (d, J=7.7 Hz, 1H), 7.43-7.33 (m, 1H), 7.33-7.18 (m, 3H), 6.97-6.79 (m, 3H), 6.34 (br d, J=8.1 Hz, 1H), 5.23 (app quint, J=7.2 Hz, 1H), 4.24 (s, 2H), 3.93-3.81 (m, 4H), 3.67 (s, 2H), 3.24-3.12 (m, 4H), 2.57 (q, J=6.9 Hz, 2H), 1.59 (d, J=6.9 Hz, 3H), 1.07 (t, J=6.9 Hz, 3H); LCMS (M+) 610, RT=1.397 (column 2; run time: 4 min).

EXAMPLE 63

2-[3-(pyridin-4-ylmethyl)ethylaminomethyl]pyridin-2-yl]-4-(trifluoromethyl)-N-[1-[3-(4-morpholinylmethyl)phenyl]ethyl]-5-thiazolecarboxaniide. $^1$H NMR (CDCl$_3$, 300 MHz): δ 8.52-8.42 (m, 3H), 8.19 (dd, J=1.5, 8.1 Hz, 1H), 7.41-7.19 (m, 7H), 6.35 (br d, J=7.3 Hz, 1H), 5.27 (app quint, J=7.2 Hz, 1H), 4.25 (s, 2H), 3.74-3.63 (m, 6H), 3.53-3.44 (m, 4H), 2.56 (q, J=7.2 Hz, 2H), 2.44 (m, 2H), 1.60 (d, J=6.6 Hz, 3H), 1.08 (t, J=7.2 Hz, 3H); LCMS (M+) 624, RT=1.113 (column 2; run time: 4 min).

EXAMPLE 64

(S)-2-[3-(4-morpholinylmethyl)pyridin-2-yl]-4-(trifluoromethyl)-N-[1-[3-(2,6-dimethyl-4-morpholinyl)phenyl]ethyl]-5-thiazolecarboxamide. $^1$H NMR (CDCl$_3$, 300 MHz): δ 8.50 (d, J=4.4 Hz, 1H), 7.97 (d, J=7.3 Hz, 1H), 7.41-7.20 (m, 2H), 6.94-6.78 (m, 3H), 6.30 (br d, J=6.2 Hz, 1H), 5.23 (app quint, J=7.2 Hz, 1H), 4.08 (s, 2H), 3.88-3.73 (m, 2H), 3.72-3.61 (m, 4H), 3.46 (d, J=12.1 Hz, 2H), 2.59-2.48 (m, 4H), 2.42 (t, J=11.2 Hz, 2H), 1.59 (d, J=7.0 Hz, 3H), 1.26 (d, J=6.6 Hz, 6H); LCMS (M+) 589, RT=1.650 (column 2; run time: 4 min).

EXAMPLE 65

(S)-2-[3-(4-pyridinylmethyl)ethylaminomethyl]pyridin-2-yl]-4-(trifluoromethyl)-N-[1-[3-(2,6-dimethyl-4-morpholinyl)phenyl]ethyl]-5-thiazolecarboxamide. $^1$H NMR (CDCl$_3$, 300 MHz): δ 8.44 (br s, 1H), 8.35 (br s, 1H), 7.37 (br s, 1H), 7.31-7.20 (m, 1H), 6.93-6.78 (m, 3H), 6.33 (br d, J=7.3 Hz, 1H), 5.23 (app quint, J=7.2 Hz, 1H), 4.26-4.09 (m, 2H), 3.87-3.72 (m, 2H), 3.50-3.40 (m, 2H), 2.99 (br s, 2H), 2.53 (br s, 2H), 2.42 (t, J=11.2 Hz, 2H), 1.59 (d, J=6.6 Hz, 3H), 1.26 (d, J=6.2 Hz, 6H), 1.02 (app br s, 9H); LCMS (M+) 589, RT=1.827 (column 2; run time: 4 min).

EXAMPLE 66

(S)-2-[3-(4-pyridinylmethyl)ethylaminomethyl]pyridin-2-yl]-4-(trifluoromethyl)-N-[1-[3-(2,6-dimethyl-4-morpholinyl)phenyl]ethyl]-5-thiazolecarboxamide. $^1$H NMR (CDCl$_3$, 300 MHz): δ 8.53-8.42 (m, 3H), 8.18 (d, J=9.1 Hz, 1H), 7.42-7.32 (m, 1H), 7.31-7.19 (m, 3H), 6.93-6.78 (m, 3H), 6.34 (br d, J=7.3 Hz, 1H), 5.23 (app quint, J=7.2 Hz, 1H), 4.24 (s, 2H), 3.88-3.71 (m, 2H), 3.67 (s, 2H), 3.52-3.41 (m, 2H), 2.56 (q, J=7.2 Hz, 2H), 2.42 (t, J=11.0 Hz, 2H), 1.59 (d, J=6.6 Hz, 3H), 1.26 (d, J=6.2 Hz, 6H), 1.07 (t, J=7.2 Hz, 3H); LCMS (M+) 638, RT=1.693 (column 2; run time: 4 min).

EXAMPLE 67

(S)-2-[3-(4-morpholinylmethyl)pyridin-2-yl]-4-(trifluoromethyl)-N-[1-[3-(3-pyridinyl)phenyl]ethyl]-5-thiazolecarboxamide. $^1$H NMR (CDCl$_3$, 300 MHz): δ 8.84-8.79 (m, 1H), 8.59 (dd, J=1.5, 4.8 Hz, 1H), 8.49 (dd, J=1.7, 4.6 Hz, 1H), 7.96 (d, J=7.0 Hz, 1H), 7.86 (dt, J=7.3, 1.8 Hz, 1H), 7.58-7.31 (m, 6H), 6.48 (br d, J=7.7 Hz, 1H), 5.36 (app quint, J=7.2 Hz, 1H), 4.08 (s, 2H), 3.71-3.58 (m, 4H), 2.57-2.45 (m, 4H), 1.65 (d, J=7.0 Hz, 3H); LCMS (M+) 553, RT=1.217 (column 2; run time: 4 min).

EXAMPLE 68

(S)-2-[3-[ethyl(2-propyl)aminomethyl]pyridin-2-yl]-4-(trifluoromethyl)-N-[1-[3-(3-pyridinyl)phenyl]ethyl]-5-thiazolecarboxamide. $^1$H NMR (CDCl$_3$, 300 MHz): δ 8.80 (d, J=1.8 Hz, 1H), 8.57 (dd, J=1.5, 4.8 Hz, 1H), 8.49-8.29 (m, 2H), 7.86 (dt, J=8.0, 1.8 Hz, 1H), 7.59-7.29 (m, 6H), 6.56 (app br s, 1H), 5.35 (app quint, J=7.2 Hz, 1H), 4.28-4.07 (m, 2H), 3.00 (app br s, 1H), 2.54 (br s, 2H), 1.65 (d, J=7.0 Hz, 3H), 1.03 (app br s, 9H); LCMS (M+) 553, RT=1.413 (column 2; run time: 4 min).

EXAMPLE 69

(S)-2-[3-[(4-pyridinylmethyl)ethylaminomethyl]pyridin-2-yl]-4-(trifluoromethyl)-N-[H-[3-(3-pyridinyl)phenyl]ethyl]-5-thiazolecarboxamide. $^1$H NMR (CDCl$_3$, 300 MHz): δ 8.82 (d, J=2.2 Hz, 1H), 8.65-8.56 (m, 1H), 8.55-8.42 (m, 3H), 8.18 (d, J=8.1 Hz, 1H), 7.93-7.83 (m, 1H), 7.64-7.19 (m, 8H), 6.53 (br d, J=7.3 Hz, 1H), 5.35 (app quint, J=7.2 Hz, 1H), 4.24 (s, 2H), 3.66 (s, 2H), 2.55 (q, J=7.2 Hz, 2H), 1.65 (d, J=6.6 Hz, 3H), 1.07 (t, J=7.0 Hz, 3H); LCMS (M+) 602, RT=1.273 (column 2; run time: 4 min).

EXAMPLE 70

2-[3-[ethyl(2-propyl)aminomethyl]pyridin-2-yl]-4-(trifluoromethyl)-N-[1-[3-(trifluoromethoxy)phenyl]ethyl]-5-thiazolecarboxamide. $^1$H NMR (CDCl$_3$, 300 MHz): δ 8.44 (d, J=3.7 Hz, 1H), 8.35 (d, J=8.1 Hz, 1H), 7.43-7.11 (m, 5H), 6.33 (br d, J=6.2 Hz, 1H), 5.29 (app quint, J=7.2 Hz, 1H), 4.15 (s, 2H), 3.05-2.91 (m, 1H), 2.52 (q, J=6.8 Hz, 2H), 1.60 (d, J=7.0 Hz, 3H), 1.07-0.93 (m, 9H); LCMS (M+) 560, RT=2.160 (column 2; run time: 4 min).

EXAMPLE 71

2-[3-[diethylaminomethyl]pyridin-2-yl]-4-(trifluoromethyl)-N-[1-[3-(trifluoromethyl)phenyl]ethyl]-5-thiazolecarboxamide. $^1$H NMR (CDCl$_3$, 300 MHz): δ 8.48 (d, J=3.7 Hz, 1H), 8.27 (br s, 1H), 7.64-7.43 (m, 4H), 7.38 (dd, J=4.4, 7.7 Hz, 1H), 6.42 (app br s, 1H), 5.32 (app quint, J=7.2 Hz, 1H), 4.24 (br s, 2H), 2.64 (br s, 4H), 1.61 (d, J=7.0 Hz, 3H), 1.06 (br s, 6H); LCMS (M+) 530, RT=2.023 (column 2; run time: 4 min).

EXAMPLE 72

2-[3-[ethyl(2-propyl)aminomethyl]pyridin-2-yl]-4-(trifluoromethyl)-N-[1-[3-(trifluoromethyl)phenyl]ethyl]-5-thiazolecarboxamide. $^1$H NMR (CDCl$_3$, 300 MHz): δ 8.44 (br s, 1H), 8.35 (br d, J=6.6 Hz, 1H), 7.64-7.44 (m, 1H), 7.42-7.31 (m, 4H), 6.46-6.29 (app br s, 1H), 5.32 (app quint, J=7.2 Hz, 1H), 4.15 (s, 2H), 3.07-2.89 (m, 1H), 2.61-2.44 (m, 2H), 1.62 (d, J=7.0 Hz, 3H), 1.10-0.91 (m, 9H); LCMS (M+) 544, RT=2.093 (column 2; run time: 4 min).

EXAMPLE 73

(S)-2-(3-methylpyridin-2-yl)-4-(trifluoromethyl)-N-[1-[3-(3-pyridinyl)phenyl]ethyl]-5-thiazolecarboxamide. $^1$H NMR (CDCl$_3$, 300 MHz): δ 8.74 (d, J=1.8 Hz, 1H), 8.52 (dd, J=1.2, 4.5 Hz, 1H), 8.39 (dd, J=1.2, 4.5 Hz, 1H), 7.83 (ddd, J=1.8,2.2,8.1 Hz, 1H), 7.60-7.22 (m, 7H), 6.87 (br d, J=7.5 Hz, 1H), 5.34 (app quint, J=7.2 Hz, 1H), 2.72 (s, 3H), 1.63 (d, J=6.9 Hz, 3H); LCMS (M+) 468, RT=1.593 (column 4; run time: 3 min).

EXAMPLE 74

2-[3-(dimethylaminomethyl)phenyl]-4-(trifluoromethyl)-N-[1-[3-(trifluoromethoxy)phenyl]ethyl]-5-thiazolecarboxamide. $^1$H NMR (CDCl$_3$, 300 MHz): δ 7.85-7.78 (m, 1H), 7.42-7.16 (m, 7H), 6.48 (br d, J=6.6 Hz, 1H), 5.28 (app quint, J=7.2 Hz, 1H), 3.59 (s, 2H), 2.18 (s, 6H), 1.60 (d, J=6.9 Hz, 3H); LCMS (M+) 517, RT=2.207 (column 3; run time: 4 min).

EXAMPLE 75

2-[3-(dimethylaminomethyl)phenyl]-4-(trifluoromethyl)-N-(3-trifluoromethylbenzyl)-5-thiazolecarboxamide. $^1$H NMR (CDCl$_3$, 300 MHz): δ 7.86-7.79 (m, 1H), 7.43-7.18 (m, 7H), 6.56 (app br s, 1H), 4.66 (d, J=5.7 Hz, 2H), 3.59 (s, 2H), 2.18 (s, 6H); LCMS (M+) 503, RT=2.143 (column 3; run time: 4 min).

EXAMPLE 76

(S)-2-[3-(dimethylaminomethyl)phenyl]-4-(trifluoromethyl)-N-[1-(3-methoxyphenyl)ethyl]-5-thiazolecarboxamide. $^1$H NMR (CDCl$_3$, 300 MHz): δ 7.80 (d, J=7.2 Hz, 1H), 7.42-7.25 (m, 4H), 6.96-6.82 (m, 3H), 6.45 (br d, J=6.6 Hz, 1H), 5.24 (app quint, J=7.2 Hz, 1H), 3.81 (s, 3H), 3.61 (s, 2H), 2.19 (s, 6H), 1.59 (d, J=6.9 Hz, 3H); LCMS (M+) 463, RT=1.877 (column 3; run time: 4 min).

EXAMPLE 77

2-[3-(diethylaminomethyl)phenyl]-4-(trifluoromethyl)-N-[1-[3-(trifluoromethoxy)phenyl]ethyl]-5-thiazolecarboxamide. $^1$H NMR (CDCl$_3$, 500 MHz): δ 7.68-7.21 (m, 8H), 6.42 (app br s, 1H), 5.28 (app quint, J=7.2 Hz, 1H), 3.77 (s, 2H), 2.47 (q, J=7.0 Hz, 4H), 1.61 (d, J=7.0 Hz, 3H), 0.90 (t, J=7.0 Hz, 6H); LCMS (M+) 547, RT=1.383 (column 2; run time: 4 min).

EXAMPLE 78

2-[3-(diethylaminomethyl)phenyl]-4-(trifluoromethyl)-N-[1-[3-(trifluoromethyl)phenyl]ethyl]-5-thiazolecarboxamide. $^1$H NMR (CDCl$_3$, 500 MHz): δ 7.68-7.25 (m, 8H), 6.46 (app br s, 1H), 5.32 (app quint, J=7.0 Hz, 1H), 3.77 (s, 2H), 2.47 (q, J=7.0 Hz, 4H), 1.62 (d, J=7.0 Hz, 3H), 0.90 (t, J=7.0 Hz, 6H); LCMS (M+) 529, RT=2.053 (column 2; run time: 4 min).

EXAMPLE 79

2-[3-(diethylaminomethyl)phenyl]-4-(trifluoromethyl)-N-(3-fluorobenzyl)-5-thiazolecarboxamide. $^1$H NMR (CDCl$_3$, 500 MHz): δ 7.69-7.00 (m, 8H), 6.52 (app br s, 1H), 4.63 (d, J=5.5 Hz, 2H), 3.92-3.70 (m, 2H), 2.63-2.38 (m, 4H), 1.05-0.83 (m, 6H); LCMS (M+) 465, RT=1.743 (column 2; run time: 4 min).

EXAMPLE 80

2-[3-(diethylaminomethyl)phenyl]-4-(trifluoromethyl)-N-(3-trifluoromethoxybenzyl)-5-thiazolecarboxamide. $^1$H NMR (CDCl$_3$, 500 MHz): δ 7.69-7.21 (m, 8H), 6.51 (s, 1H), 4.66 (d, J=6.0 Hz, 2H), 3.77 (s, 2H), 2.47 (q, J=7.0 Hz, 4H), 0.91 (t, J=7.0 Hz, 6H); LCMS (M+) 531, RT=2.030 (column 2; run time: 4 min).

EXAMPLE 81

(S)-2-[3-(diethylaminomethyl)phenyl]-4-(trifluoromethyl)-N-[1-[3-(4-morpholinyl)phenyl]ethyl]-5-thiazolecarboxamide. $^1$H NMR (CDCl$_3$, 500 MHz): δ 7.67-7.26 (m, 6H), 6.91-6.83 (m, 3H), 5.22 (app quint, J=7.2 Hz, 1H), 3.85 (t, J=4.5 Hz, 4H), 3.47 (s, 2H), 3.17 (t, J=4.5 Hz, 4H), 2.63-2.37 (m, 4H), 1.61 (t, J=6.7 Hz, 3H), 0.95 (m, 6H); LCMS (M+) 546, RT=1.533 (column 2; run time: 4 min).

EXAMPLE 82

(S)-2-[3-(diethylaminomethyl)phenyl]-4-(trifluoromethyl)-N-[1-(3-methoxyphenyl)ethyl]-5-thiazolecarboxamide. $^1$H NMR (CDCl$_3$, 500 MHz): δ 7.67-7.27 (m, 6H), 6.96-6.82 (m, 3H), 5.24 (app quint, J=7.0 Hz, 1H), 3.83-3.80 (m, 5H), 2.57-2.39 (m, 4H), 1.60 (d, J=7.0 Hz, 3H), 1.07-0.80 (m, 6H); LCMS (M+) 491, RT=1.797 (column 2; run time: 4 min).

TABLE 4

The following examples were also made by the above methods.

| Example | Structure | Method/Run Time (min) | Retention Time (min) | MS (M+) |
| --- | --- | --- | --- | --- |
| 83 | 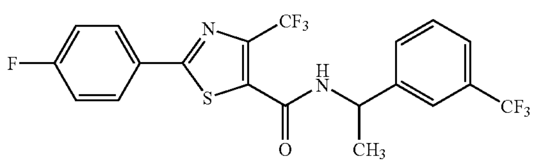 | 1/3 | 1.803 | 462 |
| 84 | 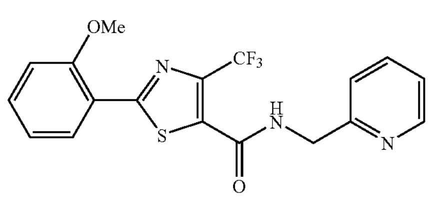 | 5/3 | 1.270 | 393 |

TABLE 4-continued

The following examples were also made by the above methods.

| Example | Structure | Method/Run Time (min) | Retention Time (min) | MS (M+) |
|---|---|---|---|---|
| 85 | 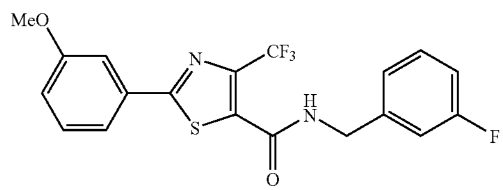 | 1/3 | 1.683 | 410 |
| 86 | 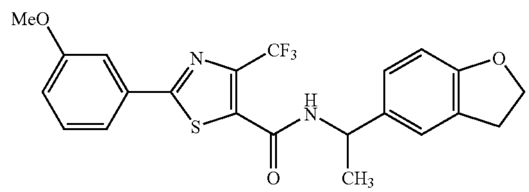 | 1/3 | 1.703 | 448 |
| 87 | 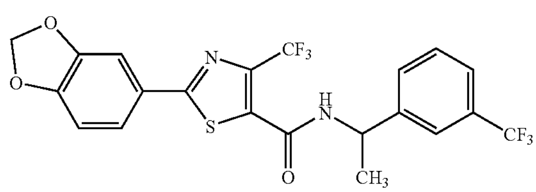 | 1/3 | 1.787 | 488 |
| 88 | 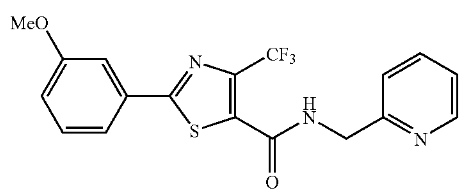 | 1/3 | 1.307 | 393 |
| 89 | 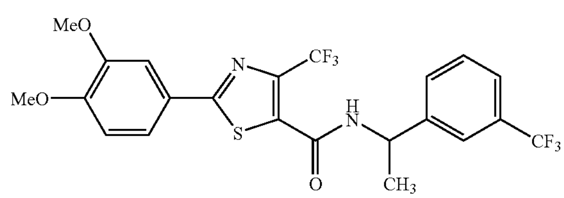 | 1/3 | 1.743 | 504 |
| 90 | 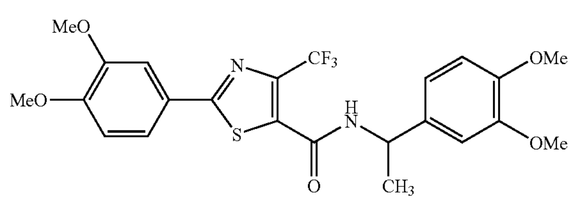 | 1/3 | 1.810 | 486 |
| 91 | 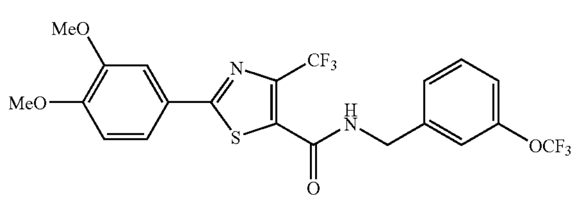 | 1/3 | 1.773 | 506 |

TABLE 4-continued

The following examples were also made by the above methods.

| Example | Structure | Method/Run Time (min) | Retention Time (min) | MS (M+) |
|---|---|---|---|---|
| 92 | 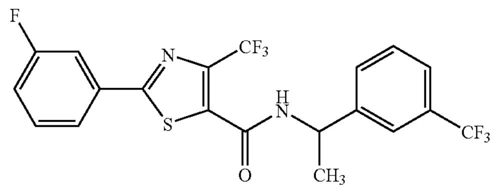 | 1/3 | 1.847 | 462 |
| 93 | 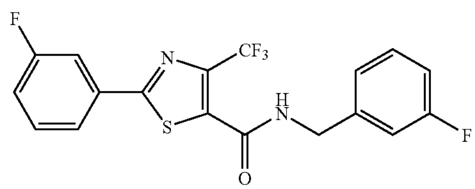 | 1/3 | 1.720 | 358 |
| 94 | 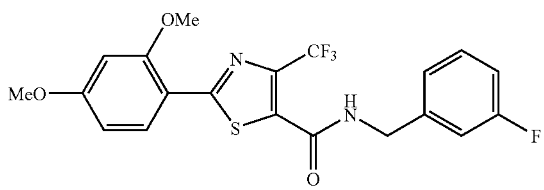 | 1/3 | 1.737 | 440 |
| 95 | 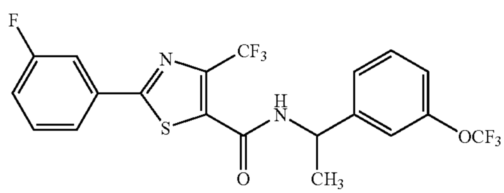 | 1/3 | 1.877 | 478 |
| 96 | 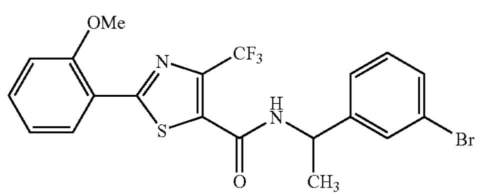 | 1/3 | 1.830 | 485 |
| 97 | 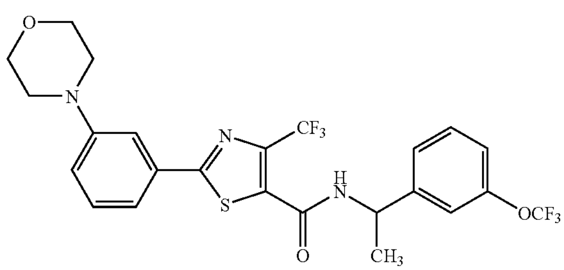 | 5/3 | 1.897 | 545 |
| 98 | 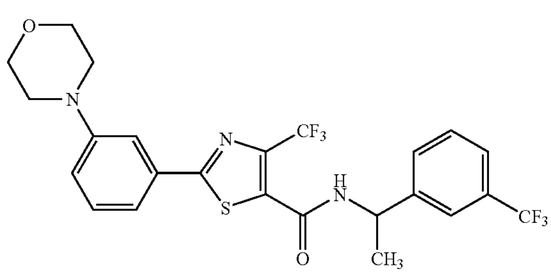 | 3/3 | 1.803 | 529 |

TABLE 4-continued

The following examples were also made by the above methods.

| Example | Structure | Method/Run Time (min) | Retention Time (min) | MS (M+) |
|---|---|---|---|---|
| 99 | 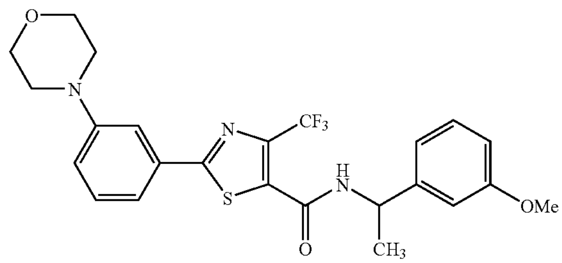 | 3/3 | 1.753 | 491 |
| 100 | 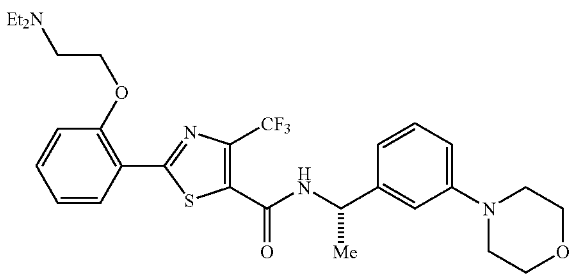 | 3/3 | 1.353 | 576 |
| 101 | 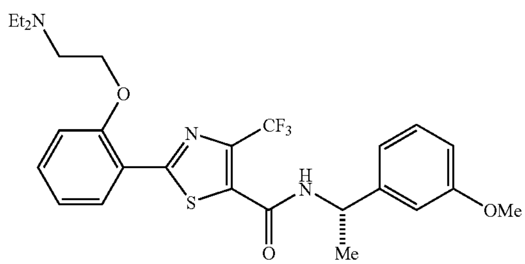 | 3/3 | 1.443 | 521 |
| 102 | 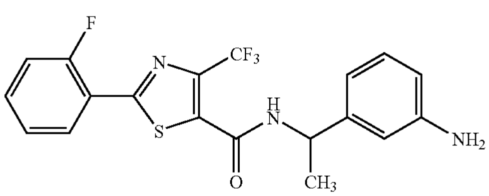 | 1/3 | 1.207 | 409 |
| 103 | 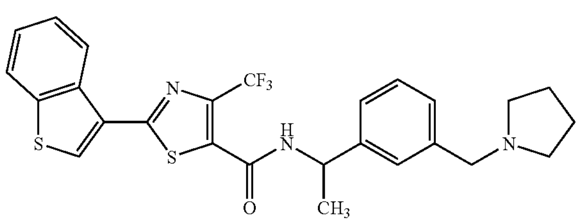 | 1/3 | 1.617 | 514 |
| 104 | 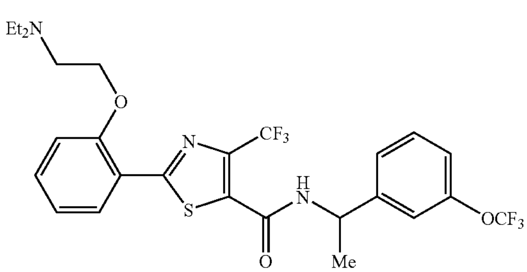 | 3/4 | 2.580 | 593 |

TABLE 4-continued

The following examples were also made by the above methods.

| Example | Structure | Method/Run Time (min) | Retention Time (min) | MS (M+) |
| --- | --- | --- | --- | --- |
| 105 | 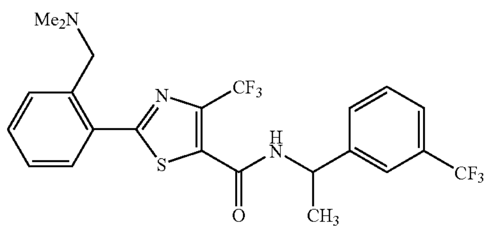 | 3/4 | 2.147 | 501 |
| 106 | 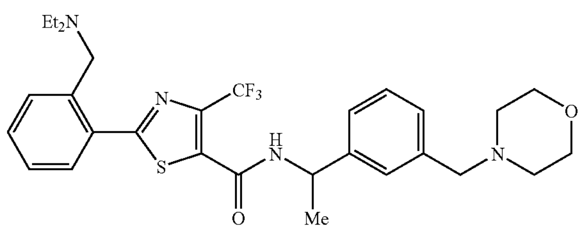 | 2/4 | 1.197 | 560 |
| 107 | 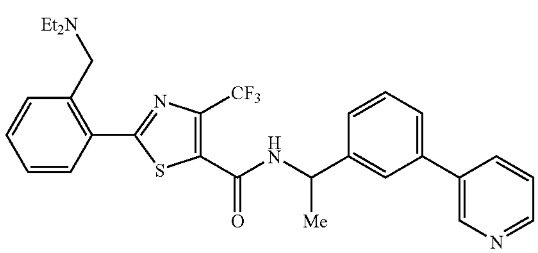 | 2/4 | 1.350 | 538 |
| 108 | 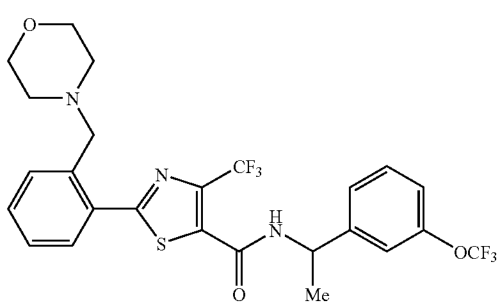 | 2/4 | 2.030 | 559 |
| 109 | 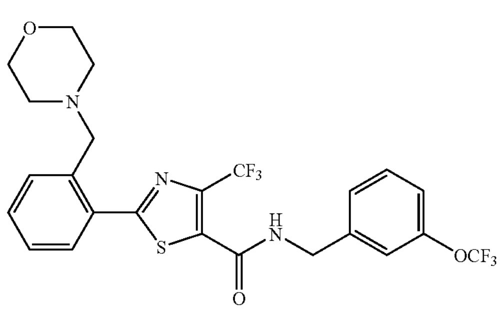 | 2/4 | 1.957 | 545 |

TABLE 4-continued

The following examples were also made by the above methods.

| Example | Structure | Method/Run Time (min) | Retention Time (min) | MS (M+) |
|---------|-----------|-----------------------|----------------------|---------|
| 110 | 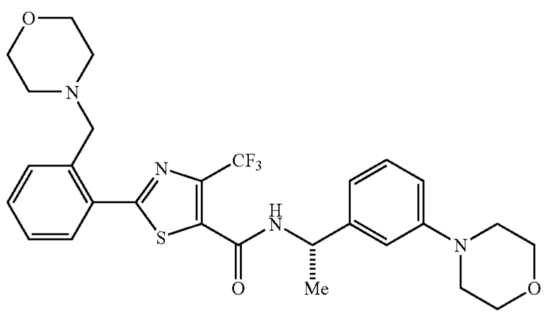 | 2/4 | 1.390 | 560 |
| 111 | 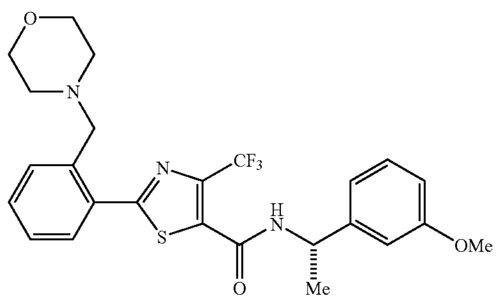 | 2/4 | 1.663 | 505 |
| 112 | 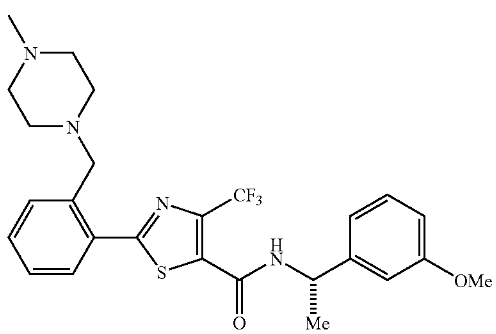 | 2/4 | 1.573 | 518 |
| 113 | 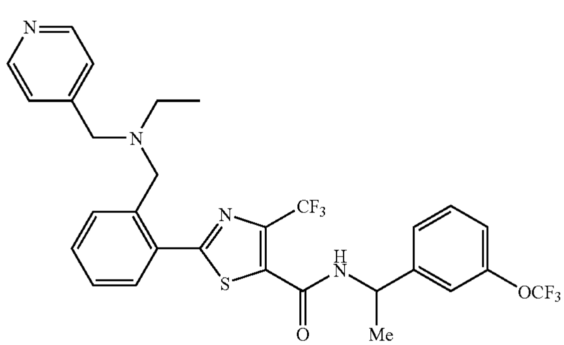 | 2/4 | 1.990 | 608 |

TABLE 4-continued

The following examples were also made by the above methods.

| Example | Structure | Method/Run Time (min) | Retention Time (min) | MS (M+) |
|---|---|---|---|---|
| 114 | 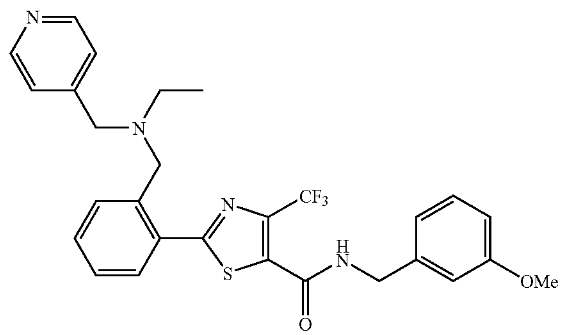 | 2/4 | 1.547 | 540 |
| 115 | 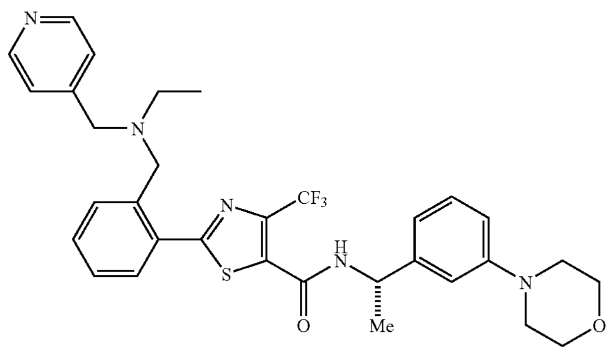 | 2/4 | 1.350 | 609 |
| 116 | 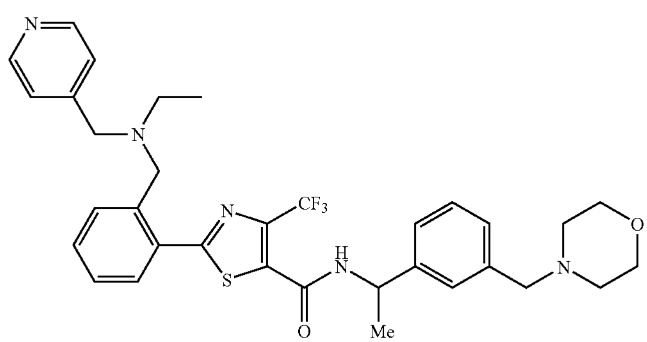 | 2/4 | 1.067 | 623 |
| 117 | 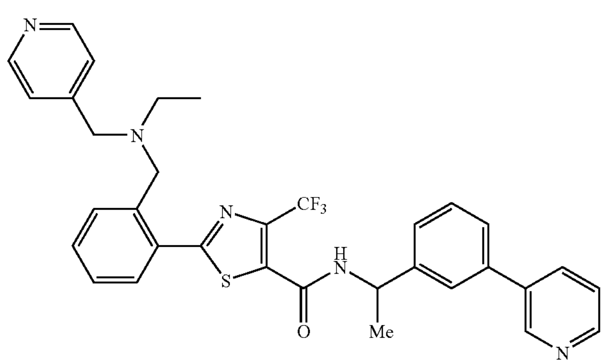 | 2/4 | 1.220 | 601 |

TABLE 4-continued
The following examples were also made by the above methods.
| Example | Structure | Method/Run Time (min) | Retention Time (min) | MS (M+) |
|---|---|---|---|---|
| 118 | 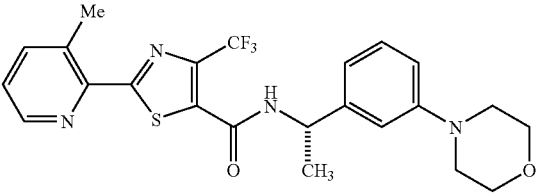 | 2/4 | 2.180 | 476 |
| 119 | 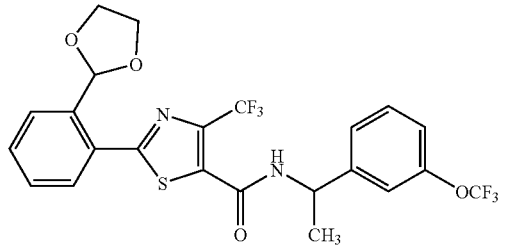 | | | |
| 120 | 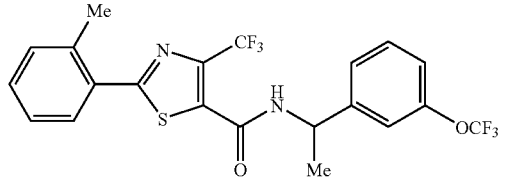 | 2/3 | 1.900 | 502 |
| 121 | 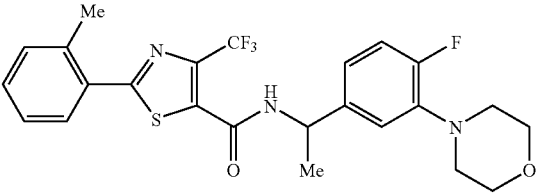 | 2/3 | 1.963 | 521 |
| 122 | 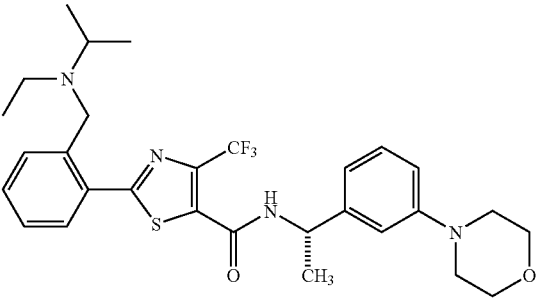 | 2/4 | 1.560 | 561 |
| 123 | 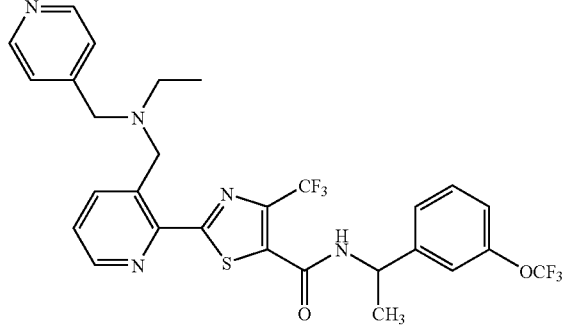 | 1/4 | 2.067 | 609 |

TABLE 4-continued

The following examples were also made by the above methods.

| Example | Structure | Method/Run Time (min) | Retention Time (min) | MS (M+) |
|---|---|---|---|---|
| 124 | 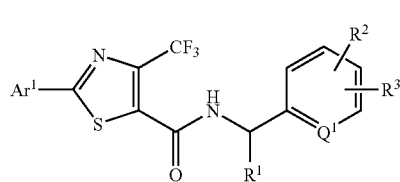 | 1/4 | 1.980 | 544 |

Methods. solvent A: 10% MeOH/90% H₂O/0.1% TFA; solvent B: 90% MeOH/10% H₂O/0.1% TFA; run time (in minutes) is a gradient from 100% A to 100% B followed by 1 minute at 100% B. Column 1: YMC ODS-A 3.0 × 50 mm S7 C18; column 2: XTERRA 3.0 × 50 mm S7; column 3: YMC ODS-A C18 S5 4.6 × 33 mm; column 4: XTERRA C18 S5 4.6 × 50 mm; column 5 YMC C18 S5 4.6 × 50 mm.

We claim:

1. A compound of Formula I

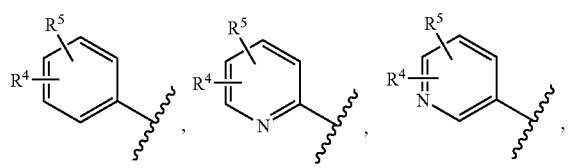

where:

$Q^1$ is CH;

$Ar^1$ is selected from the group consisting of

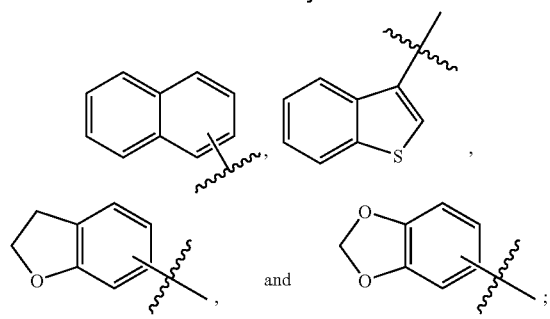

and $R^1$ is hydrogen, $C_{1-6}$alkyl, hydroxymethyl, or trifluoromethyl;

$R^2$ is halogen, $C_{1-6}$alkyl, $C_{1-2}$perfluoroalkyl, $C_{1-6}$alkoxy, $C_{1-2}$perfluoroalkoxy, —NR⁶R⁷, —(CH₂)₁₋₄NR⁶R⁷, —O(CH₂)₂₋₃NR⁶R⁷, or pyridyl;

$R^3$ is hydrogen, halogen, or $C_{1-6}$alkoxy;

$R^4$ is halogen, $C_{1-6}$alkyl, $C_{1-6}$alkoxy, —NR⁶R⁷, —(CH₂)₁₋₄NR⁶R⁷, —O(CH₂)₂₋₃NR⁶R⁷, or

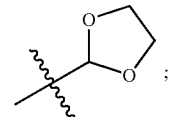

$R^5$ is hydrogen, halogen, or $C_{1-6}$alkoxy;

$R^6$ is hydrogen, $C_{1-6}$alkyl, —C(=NH)NH₂,

or

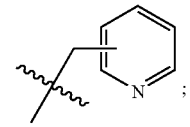

$R^7$ is hydrogen or $C_{1-6}$alkyl;

or $R^6$ and $R^7$ taken together are —CH₂CH(CH₃)OCH(CH₃)CH₂— or —CH₂CH₂XCH₂CH₂—, where X is a chemical bond, CH₂, CHOH, NH, NCH₃, NCOCH₃, O, or S;

or a pharmaceutically acceptable salt thereof.

2. A compound of claim 1 where $Ar^1$ is

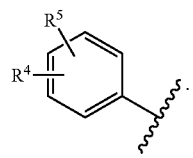

3. A compound of claim 2 selected from the group consisting of 2-(4-fluorophenyl)-N-[1-[3-(trifluoromethoxy)phenyl]ethyl]-4-(trifluoromethyl)-5-thiazolecarboxamide;

2-(2-methoxyphenyl)-N-[1-[3-(trifluoromethoxy)phenyl]ethyl]-4-(trifluoromethyl)-5-thiazolecarboxamide;

2-(2-methoxyphenyl)-4-(trifluoromethyl)-N-[1-[3-(trifluoromethyl)phenyl]ethyl]-5-thiazolecarboxamide;

2-(2-fluorophenyl)-N-[1-[3-(trifluoromethoxy)phenyl]ethyl]-4-(trifluoromethyl)-5-thiazolecarboxamide;

2-(2-fluorophenyl)-4-(trifluoromethyl)-N-[1-[3-(trifluoromethyl)phenyl]ethyl]-5-thiazolecarboxamide;

2-(2-methoxyphenyl)-N-[(1S)-1-[3-(4-morpholinyl)phenyl]ethyl]-4-(trifluoromethyl)-5-thiazolecarboxamide;

2-(3-methoxyphenyl)-N-[1-[3-(trifluoromethoxy)phenyl]ethyl]-4-(trifluoromethyl)-5-thiazolecarboxamide;

N-[1-[3-(dimethylamino)phenyl]ethyl]-2-(2-methoxyphenyl)-4-(trifluoromethyl)-5-thiazolecarboxamide;

N-[1-[3-(dimethylamino)phenyl]ethyl]-2-(2-fluorophenyl)-4-(trifluoromethyl)-5-thiazolecarboxamide;

N-[(3-fluorophenyl)methyl]-2-(2-methoxyphenyl)-4-(trifluoromethyl)-5-thiazolecarboxamide;

2-(4-methoxyphenyl)-N-[1-[3-(trifluoromethoxy)phenyl]ethyl]-4-(trifluoromethyl)-5-thiazolecarboxamide;

2-(3,4-dimethoxyphenyl)-N-[1-[3-(trifluoromethoxy)phenyl]ethyl]-4-(trifluoromethyl)-5-thiazolecarboxamide;

2-(2,4-dimethoxyphenyl)-N-[1-[3-(trifluoromethoxy)phenyl]ethyl]-4-(trifluoromethyl)-5-thiazolecarboxamide;

2-(2,4-dimethoxyphenyl)-N-[(1S)-1-[3-(4-morpholinyl)phenyl]ethyl]-4-(trifluoromethyl)-5-thiazolecarboxamide;

2-(2-methoxyphenyl)-N-[1-[3-(1-piperidinyl)phenyl]ethyl]-4-(trifluoromethyl)-5-thiazolecarboxamide;

2-(2-methoxyphenyl)-N-[1-[3-(1-pyrrolidinyl)phenyl]ethyl]-4-(trifluoromethyl)-5-thiazolecarboxamide;

N-[1-[3-[(2-furanylmethyl)methylamino]phenyl]ethyl]-2-(2-methoxyphenyl)-4-(trifluoromethyl)-5-thiazolecarboxamide;

2-(2-fluorophenyl)-N-[1-[3-[(2-furanylmethyl)methylamino]phenyl]ethyl]-4-(trifluoromethyl)-5-thiazolecarboxamide;

2-(3,4-dimethoxyphenyl)-N-[1-[3-(1-pyrrolidinylmethyl)phenyl]ethyl]-4-(trifluoromethyl)-5-thiazolecarboxamide;

2-(2-fluorophenyl)-N-[1-[3-(4-morpholinylmethyl)phenyl]ethyl]-4-(trifluoromethyl)-5-thiazolecarboxamide;

N-[1-(3-aminophenyl)ethyl]-2-(2-methoxyphenyl)-4-(trifluoromethyl)-5-thiazolecarboxamide;

N-[1-[3-[(aminoiminomethyl)amino]phenyl]ethyl]-2-(2-methoxyphenyl)-4-(trifluoromethyl)-5-thiazolecarboxamide;

2-(5-fluoro-2-methoxyphenyl)-N-[1-[3-(trifluoromethoxy)phenyl]ethyl]-4-(trifluoromethyl)-5-thiazolecarboxamide;

N-[1-[3-(dimethylamino)phenyl]ethyl]-2-(5-fluoro-2-methoxyphenyl)-4-(trifluoromethyl)-5-thiazolecarboxamide;

2-(5-fluoro-2-methoxyphenyl)-4-(trifluoromethyl)-N-[1-[3-(trifluoromethyl)phenyl]ethyl]-5-thiazolecarboxamide;

2-(5-fluoro-2-methoxyphenyl)-N-[(3-fluorophenyl)methyl]-4-(trifluoromethyl)-5-thiazolecarboxamide;

2-(5-fluoro-2-methoxyphenyl)-N-[(3-methoxyphenyl)methyl]-4-(trifluoromethyl)-5-thiazolecarboxamide;

2-(5-fluoro-2-methoxyphenyl)-N-[[3-(trifluoromethoxy)phenyl]methyl]-4-(trifluoromethyl)-5-thiazolecarboxamide;

2-(5-fluoro-2-methoxyphenyl)-N-[(1S)-1-[3-(4-morpholinyl)phenyl]ethyl]-4-(trifluoromethyl)-5-thiazolecarboxamide;

2-(5-fluoro-2-methoxyphenyl)-N-[(1S)-1-(3-methoxyphenyl)ethyl]-4-(trifluoromethyl)-5-thiazolecarboxamide;

2-(2-chlorophenyl)-N-[1-[3-(trifluoromethoxy)phenyl]ethyl]-4-(trifluoromethyl)-5-thiazolecarboxamide;

2-(2-chlorophenyl)-N-[1-[3-(dimethylamino)phenyl]ethyl]-4-(trifluoromethyl)-5-thiazolecarboxamide;

2-(2-chlorophenyl)-4-(trifluoromethyl)-N-[1-[3-(trifluoromethyl)phenyl]ethyl]-5-thiazolecarboxamide;

2-(2-chlorophenyl)-N-[(1S)-1-[3-(4-morpholinyl)phenyl]ethyl]-4-(trifluoromethyl)-5-thiazolecarboxamide;

2-(2-chlorophenyl)-N-[1-[3-(4-morpholinylmethyl)phenyl]ethyl]-4-(trifluoromethyl)-5-thiazolecarboxamide;

2-[2-[2-(diethylamino)ethoxy]phenyl]-N-[(3-fluorophenyl)methyl]-4-(trifluoromethyl)-5-thiazolecarboxamide;

N-[(1S)-1-(3-methoxyphenyl)ethyl]-2-[2-(4-morpholinyl)phenyl]-4-(trifluoromethyl)-5-thiazolecarboxamide;

2-[2-(4-morpholinyl)phenyl]-4-(trifluoromethyl)-N-[1-[3-(trifluoromethyl)phenyl]ethyl]-5-thiazolecarboxamide;

2-[2-(4-morpholinyl)phenyl]-N-[1-[3-(trifluoromethoxy)phenyl]ethyl]-4-(trifluoromethyl)-5-thiazolecarboxamide;

2-[4-(4-morpholinyl)phenyl]-N-[1-[3-(trifluoromethoxy)phenyl]ethyl]-4-(trifluoromethyl)-5-thiazolecarboxamide;

2-[2-[[ethyl(4-pyridinylmethyl)amino]methyl]phenyl]-N-[[3-(trifluoromethoxy)phenyl]methyl]-4-(trifluoromethyl)-5-thiazolecarboxamide;

2-[2-[[ethyl(4-pyridinylmethyl)amino]methyl]phenyl]-N-[(1S)-1-(3-methoxyphenyl)ethyl]-4-(trifluoromethyl)-5-thiazolecarboxamide;

2-[2-[(dimethylamino)methyl]phenyl]-N-[1-[3-(trifluoromethoxy)phenyl]ethyl]-4-(trifluoromethyl)-5-thiazolecarboxamide;

2-[2-[(dimethylamino)methyl]phenyl]-N-[[3-(trifluoromethoxy)phenyl]methyl]-4-(trifluoromethyl)-5-thiazolecarboxamide;

2-[2-[(dimethylamino)methyl]phenyl]-N-[(1S)-1-(3-methoxyphenyl)ethyl]-4-(trifluoromethyl)-5-thiazolecarboxamide;

2-[2-[(diethylamino)methyl]phenyl]-N-[1-[3-(trifluoromethoxy)phenyl]ethyl]-4-(trifluoromethyl)-5-thiazolecarboxamide;

2-[2-[(diethylamino)methyl]phenyl]-4-(trifluoromethyl)-N-[1-[3-(trifluoromethyl)phenyl]ethyl]-5-thiazolecarboxamide;

2-[2-[(diethylamino)methyl]phenyl]-N-[(3-fluorophenyl)methyl]-4-(trifluoromethyl)-5-thiazolecarboxamide;

2-[2-[(diethylamino)methyl]phenyl]-N-[[3-(trifluoromethoxy)phenyl]methyl]-4-(trifluoromethyl)-5-thiazolecarboxamide;

2-[2-[(diethylamino)methyl]phenyl]-N-[(1S)-1-[3-(4-morpholinyl)phenyl]ethyl]-4-(trifluoromethyl)-5-thiazolecarboxamide;

2-[2-[(diethylamino)methyl]phenyl]-N-[(1S)-1-(3-methoxyphenyl)ethyl]-4-(trifluoromethyl)-5-thiazolecarboxamide;

2-(4-fluorophenyl)-4-(trifluoromethyl)-N-[1-[3-(trifluoromethyl)phenyl]ethyl]-5-thiazolecarboxamide;
N-[(3-fluorophenyl)methyl]-2-(3-methoxyphenyl)-4-(trifluoromethyl)-5-thiazolecarboxamide;
N-[1-(2,3-dihydro-5-benzofuranyl)ethyl]-2-(3-methoxyphenyl)-4-(trifluoromethyl)-5-thiazolecarboxamide;
2-(3,4-dimethoxyphenyl)-4-(trifluoromethyl)-N-[1-[3-(trifluoromethyl)phenyl]ethyl]-5-thiazolecarboxamide;
2-(3,4-dimethoxyphenyl)-N-[1-(3,4-dimethoxyphenyl)ethyl]-4-(trifluoromethyl)-5-thiazolecarboxamide;
2-(3,4-dimethoxyphenyl)-N-[[3-(trifluoromethoxy)phenyl]methyl]-4-(trifluoromethyl)-5-thiazolecarboxamide;
2-(3-fluorophenyl)-4-(trifluoromethyl)-N-[1-[3-(trifluoromethyl)phenyl]ethyl]-5-thiazolecarboxamide;
2-(2,4-dimethoxyphenyl)-N-[(3-fluorophenyl)methyl]-4-(trifluoromethyl)-5-thiazolecarboxamide;
2-(3-fluorophenyl)-N-[1-[3-(trifluoromethoxy)phenyl]ethyl]-4-(trifluoromethyl)-5-thiazolecarboxamide;
N-[1-(3-bromophenyl)ethyl]-2-(2-methoxyphenyl)-4-(trifluoromethyl)-5-thiazolecarboxamide;
2-[3-(4-morpholinyl)phenyl]-N-[1-[3-(trifluoromethoxy)phenyl]ethyl]-4-(trifluoromethyl)-5-thiazolecarboxamide;
2-[3-(4-morpholinyl)phenyl]-4-(trifluoromethyl)-N-[1-[3-(trifluoromethyl)phenyl]ethyl]-5-thiazolecarboxamide;
N-[(1S)-1-(3-methoxyphenyl)ethyl]-2-[3-(4-morpholinyl)phenyl]-4-(trifluoromethyl)-5-thiazolecarboxamide;
2-[2-[2-(diethylamino)ethoxy]phenyl]-N-[(1S)-1-[3-(4-morpholinyl)phenyl]ethyl]-4-(trifluoromethyl)-5-thiazolecarboxamide;
2-[2-[2-(diethylamino)ethoxy]phenyl]-N-[(1S)-1-(3-methoxyphenyl)ethyl]-4-(trifluoromethyl)-5-thiazolecarboxamide;
N-[1-(3-aminophenyl)ethyl]-2-(2-fluorophenyl)-4-(trifluoromethyl)-5-thiazolecarboxamide;
2-[2-[2-(diethylamino)ethoxy]-5-fluorophenyl]-N-[1-[3-(trifluoromethoxy)phenyl]ethyl]-4-(trifluoromethyl)-5-thiazolecarboxamide;
2-[2-[(dimethylamino)methyl]phenyl]-4-(trifluoromethyl)-N-[1-[3-(trifluoromethyl)phenyl]ethyl]-5-thiazolecarboxamide;
2-[2-[(diethylamino)methyl]phenyl]-N-[1-[3-(4-morpholinylmethyl)phenyl]ethyl]-4-(trifluoromethyl)-5-thiazolecarboxamide;
2-[2-[(diethylamino)methyl]phenyl]-N-[1-[3-(3-pyridinyl)phenyl]ethyl]-4-(trifluoromethyl)-5-thiazolecarboxamide;
2-[2-(4-morpholinylmethyl)phenyl]-N-[1-[3-(trifluoromethoxy)phenyl]ethyl]-4-(trifluoromethyl)-5-thiazolecarboxamide;
2-[2-(4-morpholinylmethyl)phenyl]-N-[[3-(trifluoromethoxy)phenyl]methyl]-4-(trifluoromethyl)-5-thiazolecarboxamide;
2-[2-(4-morpholinylmethyl)phenyl]-N-[(1S)-1-[3-(4-morpholinyl)phenyl]ethyl]-4-(trifluoromethyl)-5-thiazolecarboxamide;
2-(3-fluorophenyl)-N-[(3-fluorophenyl)methyl]-4-(trifluoromethyl)-5-thiazolecarboxamide;
N-[(1S)-1-(3-methoxyphenyl)ethyl]-2-[2-(4-morpholinylmethyl)phenyl]-4-(trifluoromethyl)-5-thiazolecarboxamide;
N-[(1S)-1-(3-methoxyphenyl)ethyl]-2-[2-[(4-methyl-1-piperazinyl)methyl]phenyl]-4-(trifluoromethyl)-5-thiazolecarboxamide;
2-[2-[[ethyl(4-pyridinylmethyl)amino]methyl]phenyl]-N-[1-[3-(trifluoromethoxy)phenyl]ethyl]-4-(trifluoromethyl)-5-thiazolecarboxamide;
2-[2-[[ethyl(4-pyridinylmethyl)amino]methyl]phenyl]-N-[(3-methoxyphenyl)methyl]-4-(trifluoromethyl)-5-thiazolecarboxamide;
2-[2-[[ethyl(4-pyridinylmethyl)amino]methyl]phenyl]-N-[(1S)-1-[3-(4-morpholinyl)phenyl]ethyl]-4-(trifluoromethyl)-5-thiazolecarboxamide;
2-[2-[[ethyl(4-pyridinylmethyl)amino]methyl]phenyl]-N-[1-[3-(4-morpholinylmethyl)phenyl]ethyl]-4-(trifluoromethyl)-5-thiazolecarboxamide;
2-[2-[[ethyl(4-pyridinylmethyl)amino]methyl]phenyl]-N-[1-[3-(3-pyridinyl)phenyl]ethyl]-4-(trifluoromethyl)-5-thiazolecarboxamide;
2-(2-methylbenzoyl)-N-[1-[3-(trifluoromethoxy)phenyl]ethyl]-4-(trifluoromethyl)-5-thiazolecarboxamide; and
N-[1-[4-fluoro-3-(4-morpholinyl)phenyl]ethyl]-2-(2-methylbenzoyl)-4-(trifluoromethyl)-5-thiazolecarboxamide.

4. A compound of claim 1 where $Ar^1$ is

5. A compound of claim 4 selected from the group consisting of

2-[3-[(diethylamino)methyl]-2-pyridinyl]-N-[1-[3-(trifluoromethoxy)phenyl]ethyl]-4-(trifluoromethyl)-5-thiazolecarboxamide;
2-[3-[[ethyl(4-pyridinylmethyl)amino]methyl]-2-pyridinyl]-N-[(1S)-1-[3-(4-morpholinyl)phenyl]ethyl]-4-(trifluoromethyl)-5-thiazolecarboxamide;
2-[3-[[ethyl(4-pyridinylmethyl)amino]methyl]-2-pyridinyl]-N-[1-[3-(4-morpholinylmethyl)phenyl]ethyl]-4-(trifluoromethyl)-5-thiazolecarboxamide;
N-[(1S)-1-[3-[(2R,6S)-2,6-dimethyl-4-morpholinyl]phenyl]ethyl]-2-[4-(4-morpholinylmethyl)-2-pyridinyl]-4-(trifluoromethyl)-5-thiazolecarboxamide;
N-[(1S)-1-[3-[(2R,6S)-2,6-dimethyl-4-morpholinyl]phenyl]ethyl]-2-[3-[[ethyl(1-methylethyl)amino]methyl]-2-pyridinyl]-4-(trifluoromethyl)-5-thiazolecarboxamide;
N-[(1S)-1-[3-[(2R,6S)-2,6-dimethyl-4-morpholinyl]phenyl]ethyl]-2-[3-[[ethyl(4-pyridinylmethyl)amino]methyl]-2-pyridinyl]-4-(trifluoromethyl)-5-thiazolecarboxamide;
2-[3-(4-morpholinylmethyl)-2-pyridinyl]-N-[(1S)-1-[3-(3-pyridinyl)phenyl]ethyl]-4-(trifluoromethyl)-5-thiazolecarboxamide;
2-[3-[[ethyl(1-methylethyl)amino]methyl]-2-pyridinyl]-N-[(1S)-1-[3-(3-pyridinyl)phenyl]ethyl]-4-(trifluoromethyl)-5-thiazolecarboxamide;
2-[3-[[ethyl(4-pyridinylmethyl)amino]methyl]-2-pyridinyl]-N-[(1S)-1-[3-(3-pyridinyl)phenyl]ethyl]-4-(trifluoromethyl)-5-thiazolecarboxamide;
2-[3-[[ethyl(1-methylethyl)amino]methyl]-2-pyridinyl]-N-[1-[3-(trifluoromethoxy)phenyl]ethyl]-4-(trifluoromethyl)-5-thiazolecarboxamide;

2-[3-[(diethylamino)methyl]-2-pyridinyl]-4-(trifluoromethyl)-N-[1-[3-(trifluoromethyl)phenyl]ethyl]-5-thiazolecarboxamide;
2-[3-[[ethyl(1-methylethyl)amino]methyl]-2-pyridinyl]-4-(trifluoromethyl)-N-[1-[3-(trifluoromethyl)phenyl]ethyl]-5-thiazolecarboxamide;
2-(3-methyl-2-pyridinyl)-N-[(1S)-1-[3-(3-pyridinyl)phenyl]ethyl]-4-(trifluoromethyl)-5-thiazolecarboxamide;
2-(3-methyl-2-pyridinyl)-N-[(1S)-1-[3-(4-morpholinyl)phenyl]ethyl]-4-(trifluoromethyl)-5-thiazolecarboxamide;
2-[3-(1,3-dioxolan-2-yl)-2-pyridinyl]-N-[1-[3-(trifluoromethoxy)phenyl]ethyl]-4-(trifluoromethyl)-5-thiazolecarboxamide;
2-[3-[[ethyl(1-methylethyl)amino]methyl]-2-pyridinyl]-N-[(1S)-1-[3-(4-morpholinyl)phenyl]ethyl]-4-(trifluoromethyl)-5-thiazolecarboxamide;
2-[3-[[ethyl(4-pyridinylmethyl)amino]methyl]-2-pyridinyl]-N-[1-[3-(trifluoromethoxy)phenyl]ethyl]-4-(trifluoromethyl)-5-thiazolecarboxamide;
2-[3-(4-morpholinylmethyl)-2-pyridinyl]-4-(trifluoromethyl)-N-[1-[3-(trifluoromethyl)phenyl]ethyl]-5-thiazolecarboxamide.

6. A compound of claim 1 where $R^1$ is methyl.

7. A compound of claim 1 where $R^1$ is hydrogen.

8. A compound of claim 1 where the structure is tat of Formula Ig.

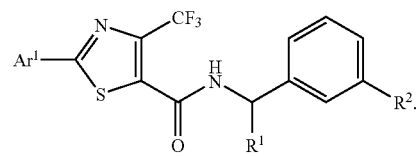

9. A compound of claim 1 where $R^1$ is $C_{1-6}$alkyl and the stereochemical configuration is that of Formula Ia.

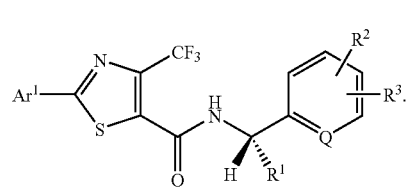

10. A pharmaceutical composition comprising a compound of claim 1 and a pharmaceutically acceptable carrier.

* * * * *